United States Patent
Wang et al.

(10) Patent No.: US 12,209,074 B2
(45) Date of Patent: Jan. 28, 2025

(54) SHP2 PHOSPHATASE ALLOSTERIC INHIBITOR

(71) Applicant: BEIJING SHENOGEN PHARMA GROUP LTD., Beijing (CN)

(72) Inventors: Huting Wang, Beijing (CN); Lei Zhang, Beijing (CN); Yonggang Wang, Beijing (CN); Lixin Fan, Beijing (CN); Lei Liu, Beijing (CN); Dong Wei, Beijing (CN); Jing Wang, Winchester, MA (US); Jiaojiao Wang, Beijing (CN); Dongliang Mo, Beijing (CN); Mingji Jin, Beijing (CN); Yong Peng, Beijing (CN); Kun Meng, Beijing (CN)

(73) Assignee: BEIJING SHENOGEN PHARMA GROUP LTD., Beijing (CN)

( * ) Notice: Subject to any disclaimer, the term of this patent is extended or adjusted under 35 U.S.C. 154(b) by 692 days.

(21) Appl. No.: 17/618,835

(22) PCT Filed: Jun. 12, 2020

(86) PCT No.: PCT/CN2020/095795
§ 371 (c)(1),
(2) Date: Dec. 13, 2021

(87) PCT Pub. No.: WO2020/249079
PCT Pub. Date: Dec. 17, 2020

(65) Prior Publication Data
US 2022/0388977 A1    Dec. 8, 2022

(30) Foreign Application Priority Data

| Jun. 14, 2019 | (CN) | 201910515196.0 |
| Nov. 4, 2019 | (CN) | 201911068821.8 |
| Jan. 17, 2020 | (CN) | 202010056703.1 |
| Jun. 9, 2020 | (CN) | 202010517372.7 |

(51) Int. Cl.
*C07D 401/04* (2006.01)
*A61P 35/00* (2006.01)
*C07D 401/14* (2006.01)
*C07D 471/10* (2006.01)

(52) U.S. Cl.
CPC .......... *C07D 401/04* (2013.01); *A61P 35/00* (2018.01); *C07D 401/14* (2013.01); *C07D 471/10* (2013.01)

(58) Field of Classification Search
CPC .................................................... C07D 401/04
See application file for complete search history.

(56) References Cited

U.S. PATENT DOCUMENTS

| 10,934,302 B1 * | 3/2021 | Taylor | C07D 491/107 |
| 12,084,447 B2 * | 9/2024 | Taylor | C07D 417/06 |

FOREIGN PATENT DOCUMENTS

| CA | 3094690 A1 | 9/2019 |
| CA | 3114160 A1 | 4/2020 |
| KR | 20210015758 A | 2/2021 |
| KR | 20210075110 A | 6/2021 |
| WO | 2008096746 A1 | 8/2008 |
| WO | 2017216706 A1 | 12/2017 |
| WO | 2018172984 A1 | 9/2018 |
| WO | 2019051084 A1 | 3/2019 |
| WO | 2019183367 A1 | 9/2019 |
| WO | 2020063760 A1 | 4/2020 |
| WO | 2020073949 A1 | 4/2020 |

* cited by examiner

*Primary Examiner* — Golam M Shameem
(74) *Attorney, Agent, or Firm* — Lando & Anastasi, LLP

(57) ABSTRACT

A SHP2 phosphatase allosteric inhibitor and a drug containing said inhibitor, the SHP2 phosphatase allosteric inhibitor having the structure shown in formula (I), and the use of an optical isomer compound of the SHP2 phosphatase allosteric inhibitor or a pharmaceutically acceptable salt thereof in the preparation of drugs for the treatment of tumor diseases.

8 Claims, No Drawings

SHP2 PHOSPHATASE ALLOSTERIC INHIBITOR

CROSS-REFERENCE TO RELATED APPLICATIONS

This application is a U.S. national phase application under 35 U.S.C. § 371 of International Application No. PCT/CN2020/095795, filed Jun. 12, 2020, which claims the benefit of Chinese Application Nos. 201910515196.0 filed Jun. 14, 2019, 201911068821.8 filed Nov. 4, 2019, 202010056703.1 filed Jan. 17, 2020, and 202010517372.7 filed Jun. 9, 2020.

TECHNICAL FIELD

The present invention relates to a SHP2 phosphatase allosteric inhibitor and a medicament comprising the inhibitor, which belongs to the pharmaceutical field.

BACKGROUND

SHP2 is a non-receptor protein tyrosine phosphatase encoded by the PTPN11 gene, and SHP2 is involved in signaling pathways, such as Ras-Erk, PI3k-Akt, Jak-Stat, NF-κB and mTOR (Bing Yu, Wei Liu, Wen-Mei Yu, Mignon L. Loh et al. Molecular Cancer Therapeutics 2013, 12, 1738-1748).

SHP2 comprises two SH2 domains in series and one PTP domain with the function of catalyzation. SHP2 is in an inactive conformation, and the SH2 domain blocks the substrate from approaching the catalytic site until SH2 is interacted with cytokines or growth factors, causing SHP2 to become allosteric and expose its catalytic site.

Hyperactivation of SHP2 causes a variety of diseases, therefore, SHP2 becomes an attractive target. A SHP2 inhibitor with the following formula

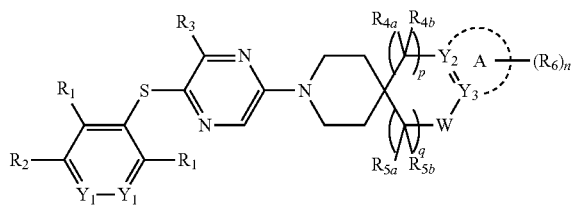

has been disclosed in the patert application WO2018172984. A variety of compounds are listed in the examples of this patent application and the compounds illustrated are proved to have an inhibitory effect on MV-4-11 leukemia cells.

The SHP2 inhibitor with the formula of has

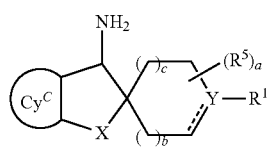

been disclosed in patent application WO2019183367, and a plenty of compounds with the above formula are listed in the specification of the application and are proved to have inhibitory effect on SHP2 kinase. The present invention provides a novel allosteric inhibitor of SHP2 phosphatase and the inhibitory activity of the inhibitor.

SUMMARY

The present invention aims to provide an optical isomer compound of SHP2 phosphatase allosteric inhibitor or a pharmaceutically acceptable salt thereof.

One aspect of the invention provides an optical isomer compound of SHP2 phosphatase allosteric inhibitor or a pharmaceutically acceptable salt thereof. The inhibitor compound has the following formula (I):

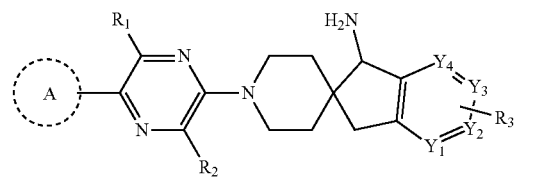

wherein,

is a substituted or unsubstituted phenyl, indazolyl or pyridyl; $R_1$ and $R_2$ are each independently selected from —$CH_3$, —$NH_2$, —$CH_2OH$, —$C(O)O(CH_2)_1CH_3$, —CN, —H, —OH, —$C(O)NH_2$ or —$CH(OH)CH_3$; $R_3$ is selected from H, $C_{1-6}$ alkyl, —$CF_3$, halogen, —$SO_2CH_3$, —$OCH_3$, —CN, —$C(O)NH_2$, —$NH_nSO_{3-m}(CH_3)_m$, —$CH_n(CH_3)_mOH$, —$OCF_3$ or —$C(O)CH_3$; $Y_1$, $Y_2$, $Y_3$ and $Y_4$ are each independently selected from —C— or —N—; n=0 or 1; and m=1 or 2.

Preferably, the compound or the pharmaceutically acceptable salt thereof has the following formula (II):

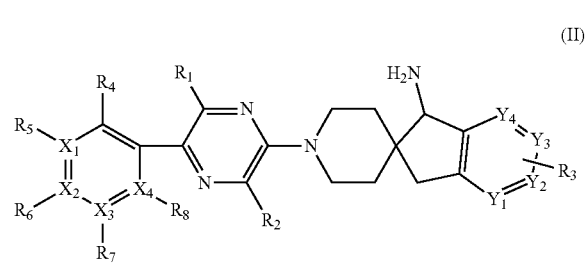

wherein, $X_1$, $X_2$, $X_3$ or $X_4$ is each independently selected from C or N; $R_1$ and $R_2$ are each independently selected from —H, —$CH_3$, —$NH_2$, —$C(O)O(CH_2)_nCH_3$, —CN, —OH, —$CH_2OH$, —$C(O)NH_2$ or —$CH(OH)CH_3$; $R_3$ is selected from H, $C_{1-6}$ alkyl, —$CF_3$, halogen, —$SO_2CH_3$, —$OCH_3$, —CN, —$C(O)NH_2$, —$NHSO_2CH_3$, —$NSO(CH_3)_2$, —$CH_n(CH_3)_{2-n}$, —$C(O)CH_3$ or —$OCF_3$; $R_4$, $R_5$, $R_6$, $R_7$ and $R_8$ are each independently selected from —H, —Cl, —$CH_3$, —Br, —$CF_3$, $CH_3O$—, $CH_3SO_2$—, =O, $CH_3NH$— and —$NH_2$; $Y_1$, $Y_2$, $Y_3$ and $Y_4$ are each independently selected from C or N; and n=0 or 1.

Preferably, $R_1$ is selected from —$CH_3$ or —$NH_2$; $R_2$ is selected from —$CH_2OH$, —$C(OH)CH_3$, —$C(O)O(CH_2)_nCH_3$, —$CN$, —$H$ or —$C(O)NH_2$.

Preferably, the compound has the following formula (III):

(III)

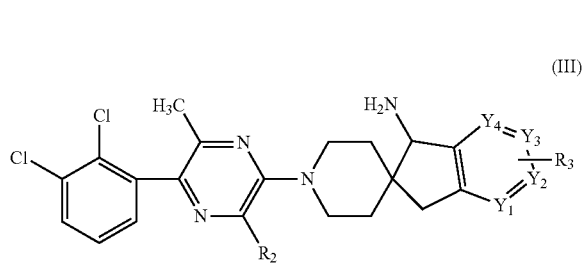

$R_2$ is selected from —$C(O)O(CH_2)_nCH_3$, —$CH_2OH$ or —$CH(OH)CH_3$; $Y_1$, $Y_2$, $Y_3$ and $Y_4$ are each independently selected from N or C; $R_3$ is selected from H, halogen, —CN, —$CONH_2$, —$NSO(CH_3)_2$, —$CF_3$, —$CH_3$, —$OCF_3$, —$SO_2CH_3$ or —$OCH_3$.

Preferably, the compound has the following formula (IV):

(IV)

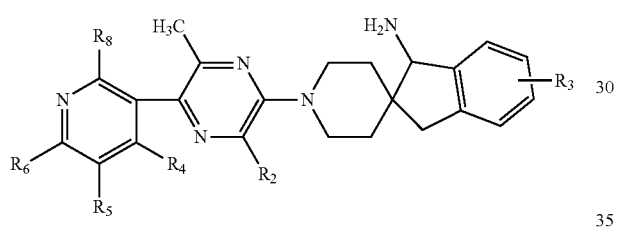

wherein, $R_4$, $R_5$, $R_6$ or $R_8$ is each independently selected from —H, —$CH_3$, $CH_3NH$—, —$NH_2$, —Cl, $CH_3O$— and —$CF_3$; $R_3$ is selected from H, —$CH_3$, —$OCH_3$, —CN or halogen; $R_2$ is selected from —$CH_2OH$ or —$C(O)O(CH_2)_nCH_3$; and n=1.

Preferably, the compound has the following formula (V):

(V)

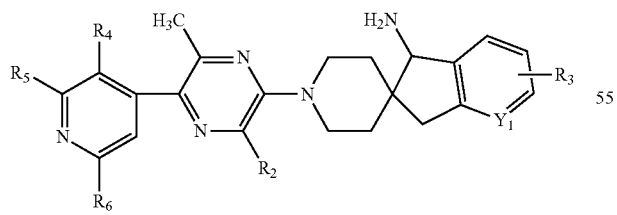

wherein, $R_2$ is selected from —$CH_2OH$, —$CHOHCH_3$ or —$C(O)O(CH_2)_nCH_3$; $Y_1$ is selected from C or N; $R_3$ is selected from H, —$CH_3$, —$OCH_3$, —CN or halogen, $R_4$, $R_5$ and $R_6$ are each independently selected from —H, halogen, —$CH_3$, —$CF_3$, —$OCH_3$, —CN, —NHR, —$N(CH_3)_2$ or —$NH_2$; R is $C_{1-3}$alkyl or cycloalkyl; and n=0 or 1.

Preferably, the compound has the following formula (VI):

(VI)

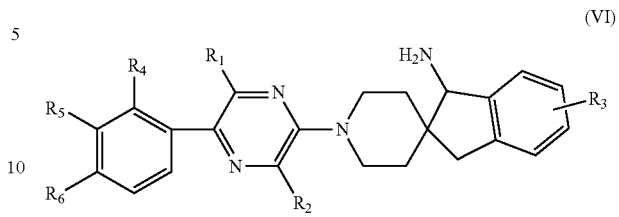

wherein, $R_1$ is selected from —$CH_3$ or H; $R_2$ is selected from —$CH_2OH$ or —$C(O)OCH_3$; $R_3$ is selected from H, halogen, —$CF_3$, —$OCH_3$, —$OCF_3$, —CN, —$C(O)NH_2$, —$NH_nSO_{3-m}(CH_3)_m$, $C_{1-6}$ alkyl or $CH_3SO_2$—; $R_4$, $R_5$ and $R_6$ are each independently selected from H, halogen, —$CF_3$, alkoxy, $CH_3NH$—, $CH_3SO_2$— or $C_{1-3}$ substituted or unsubstituted alkyl; n=0 or 1; and m=1 or 2.

Preferably, the compound comprises:

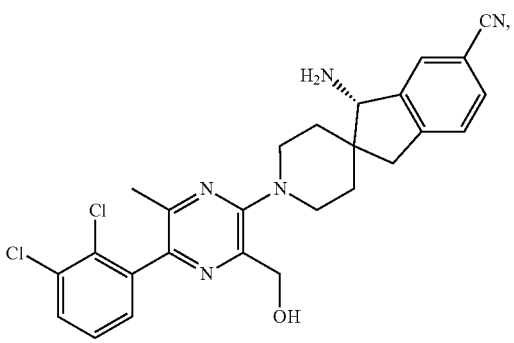

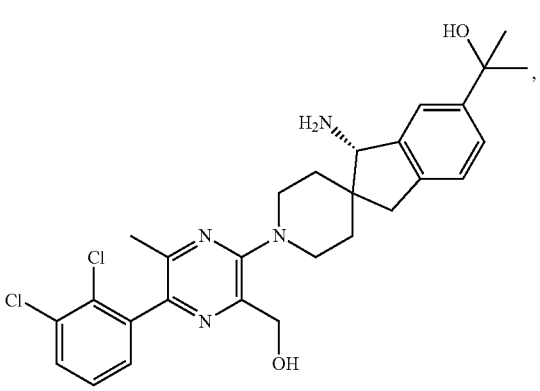

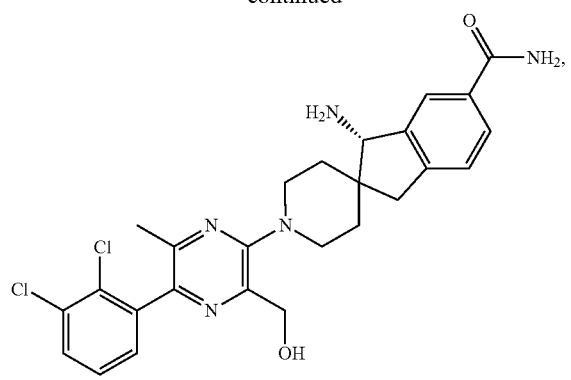
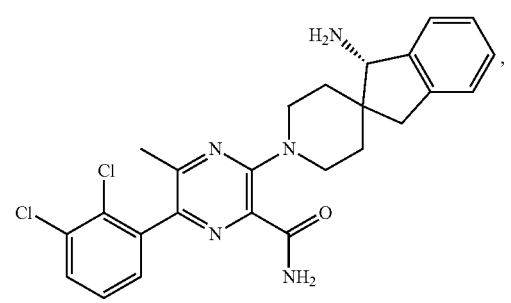
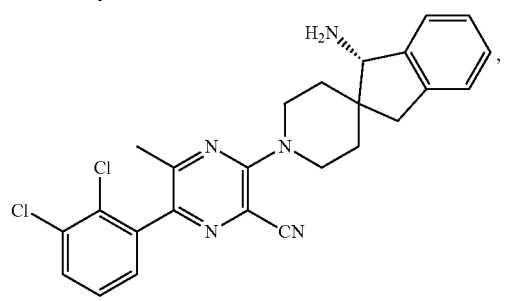
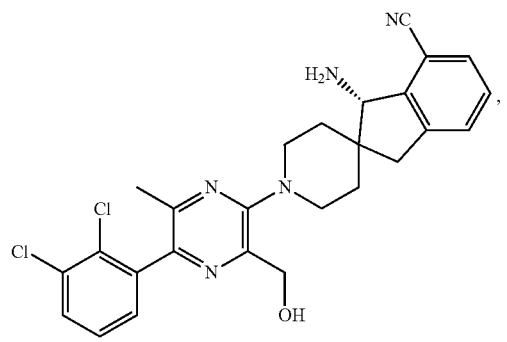
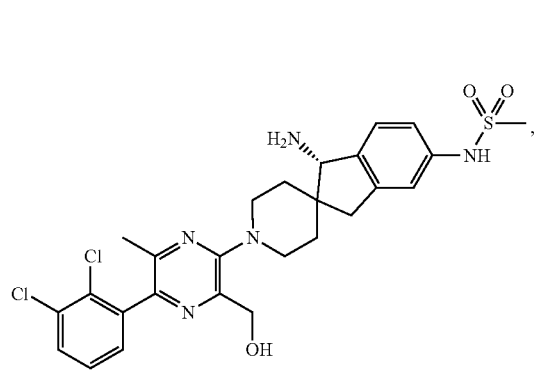
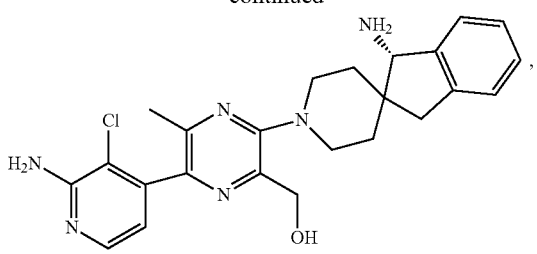
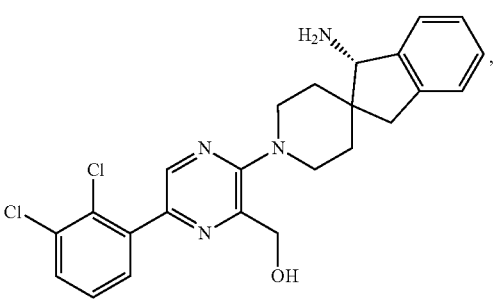
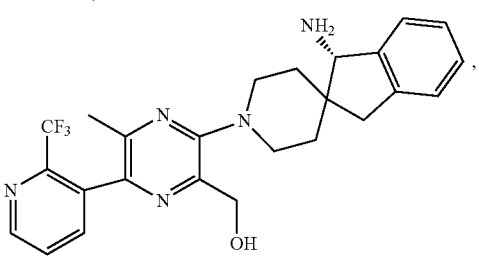
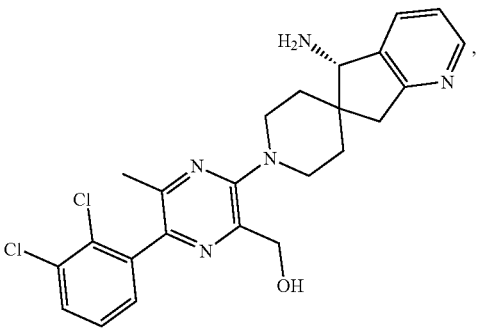
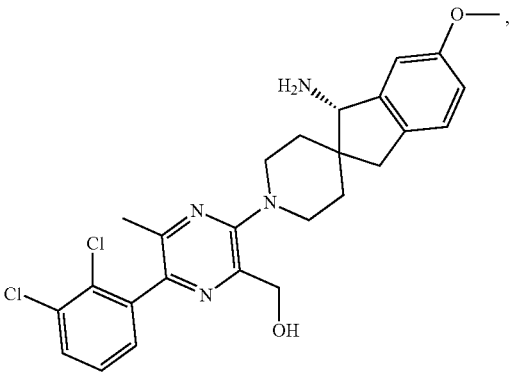

-continued
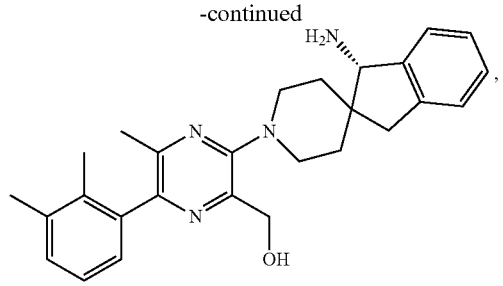
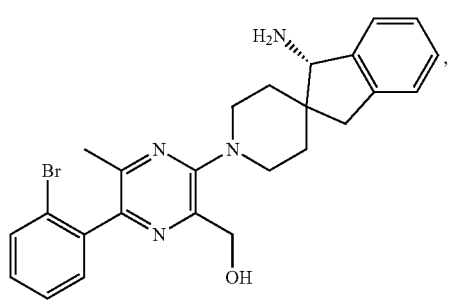
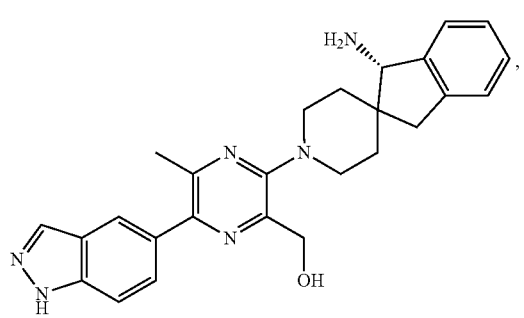
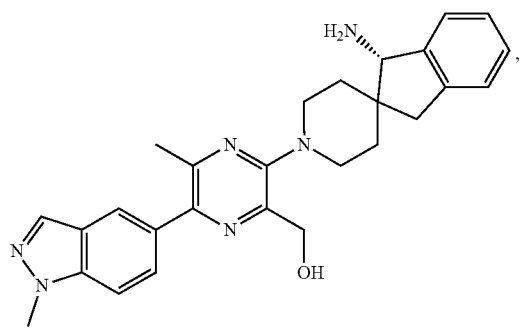
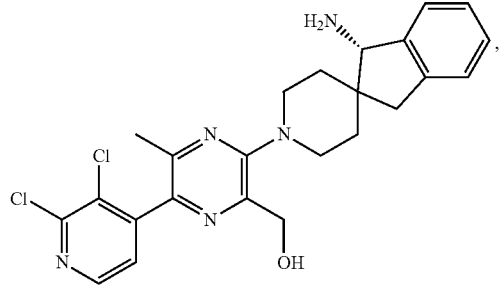
-continued
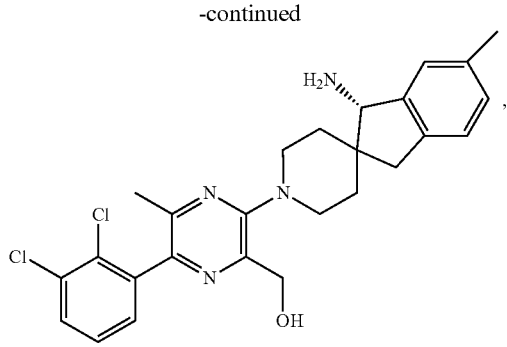
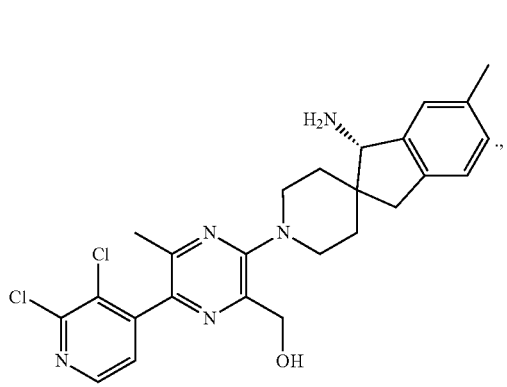
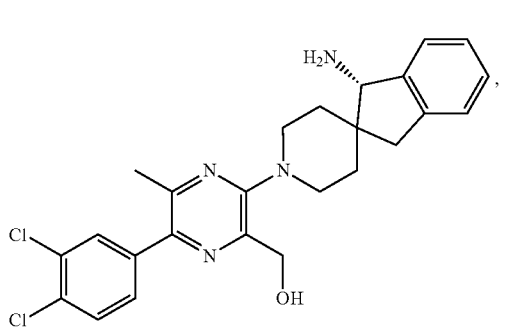
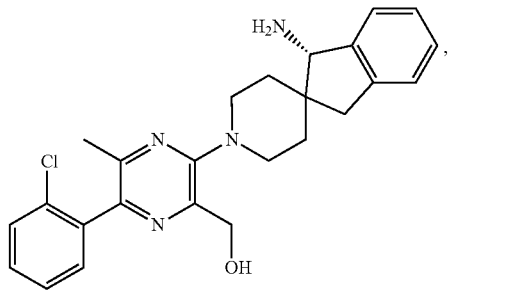
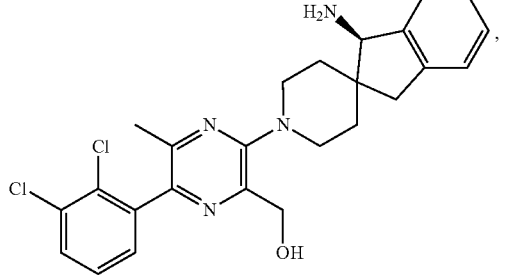

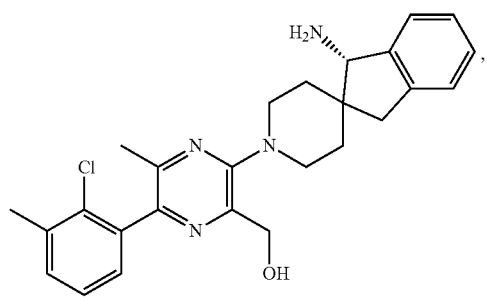
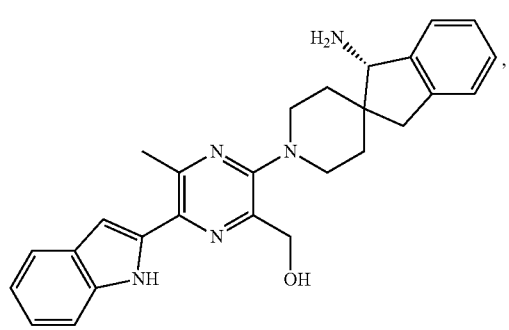
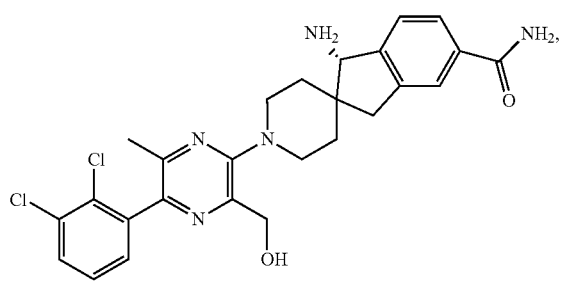
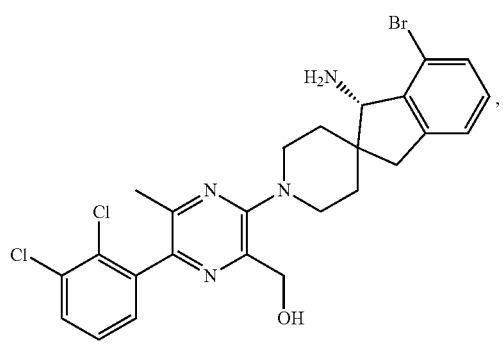
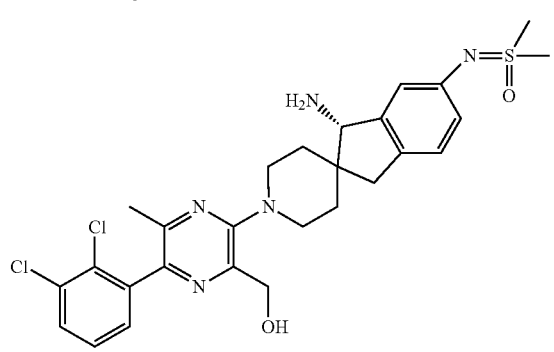
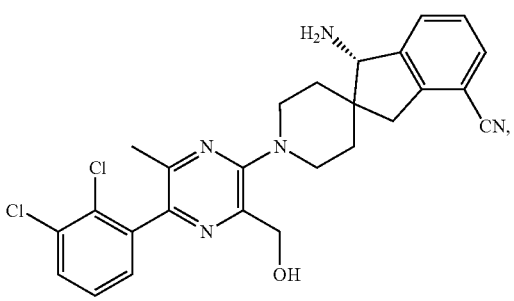
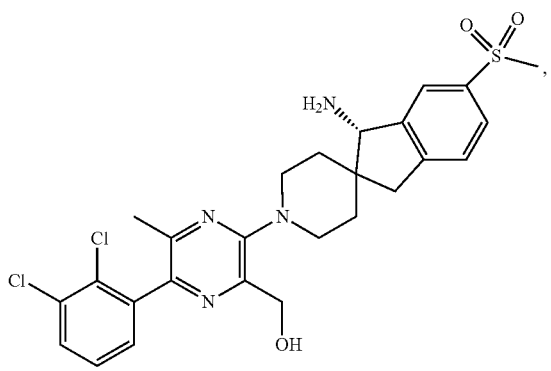
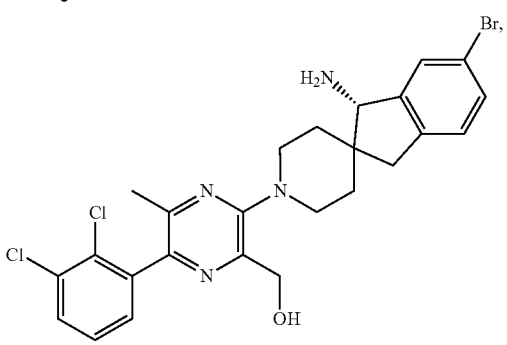
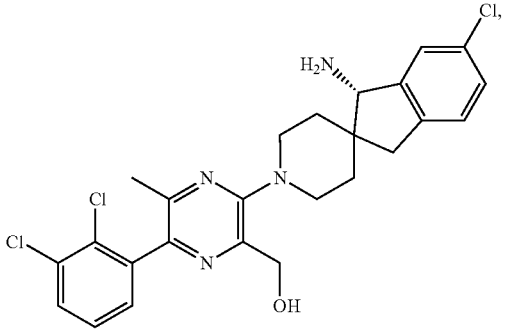
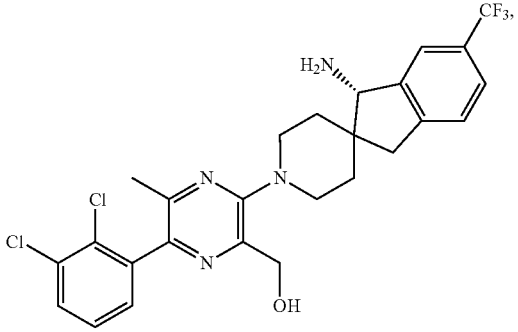

-continued
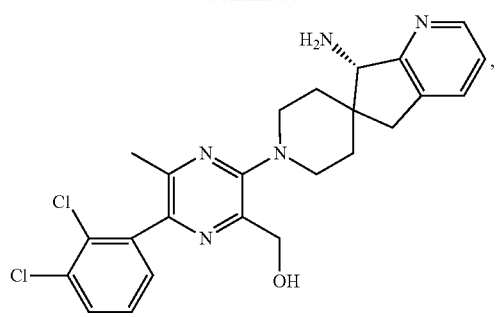
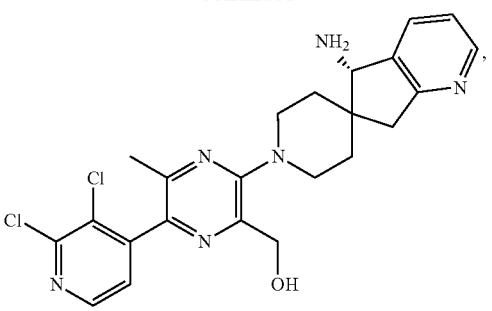
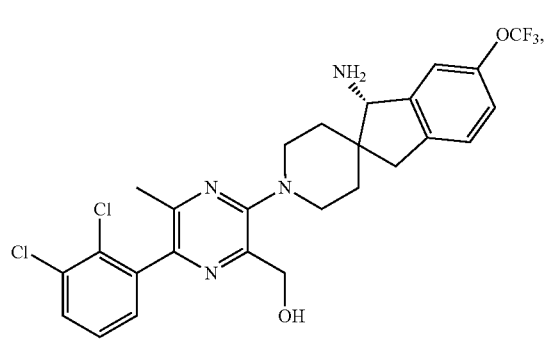
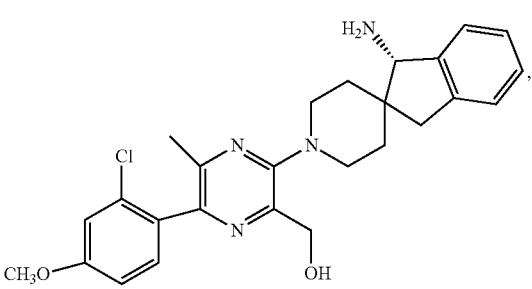
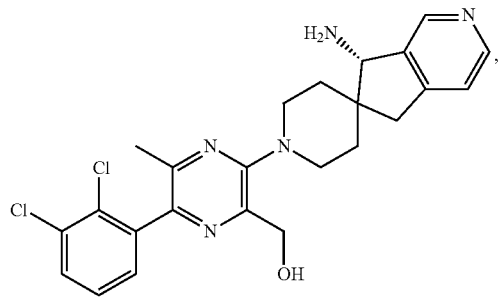
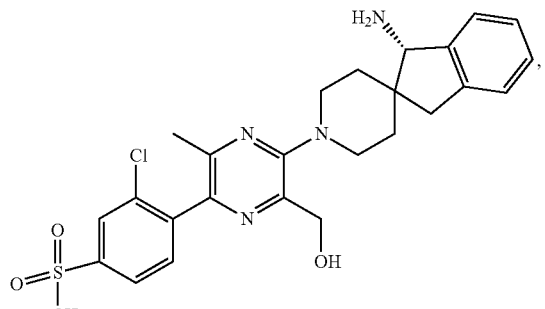
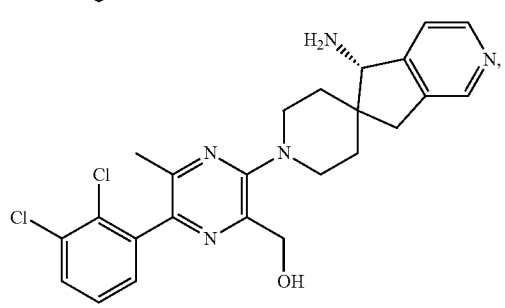
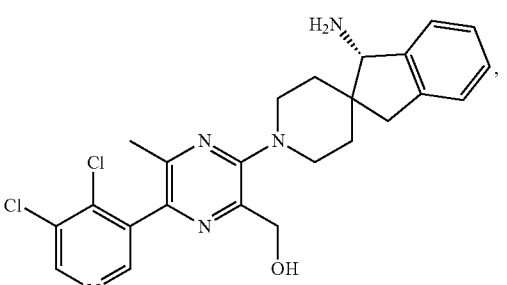
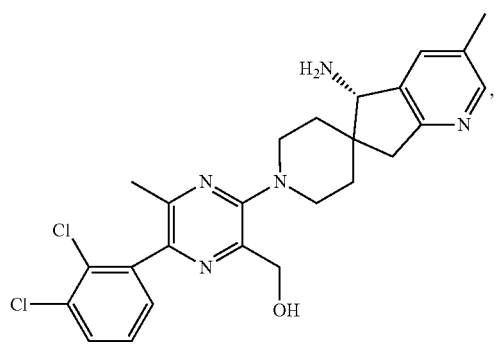
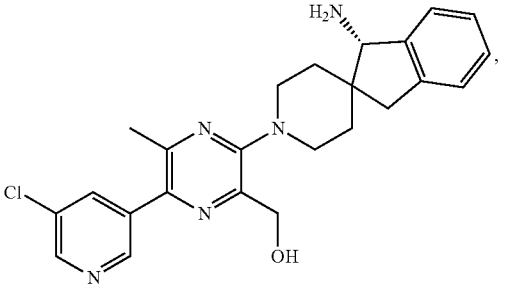

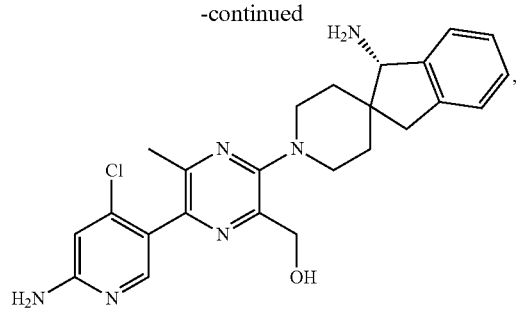
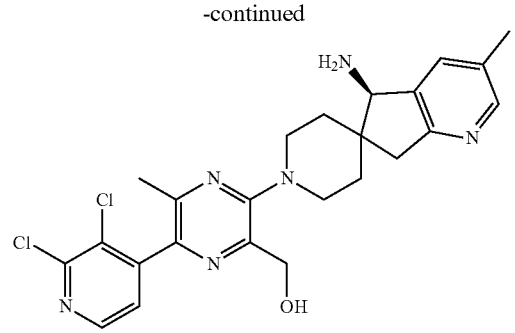
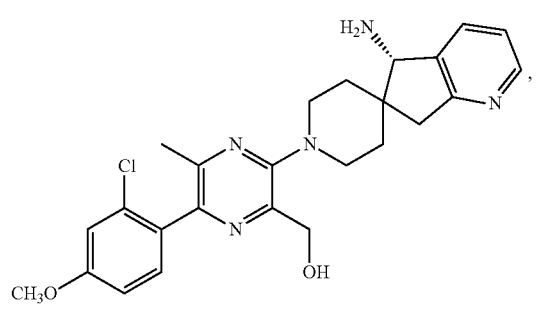
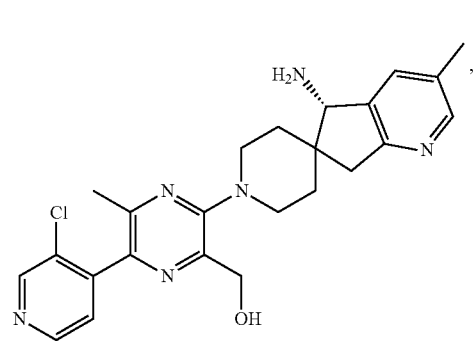
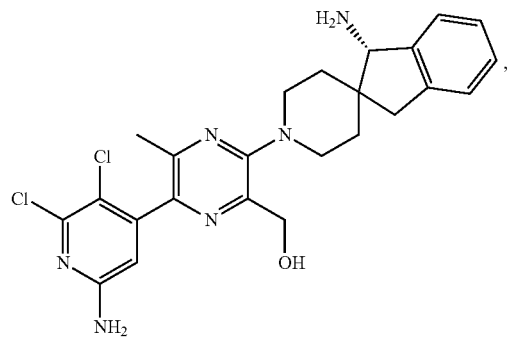
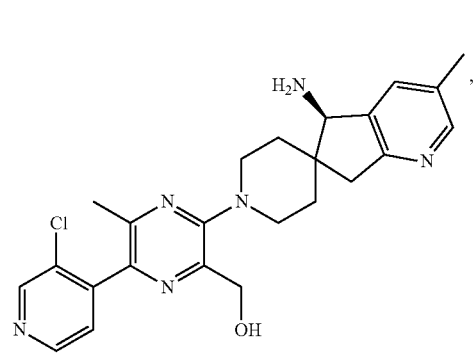
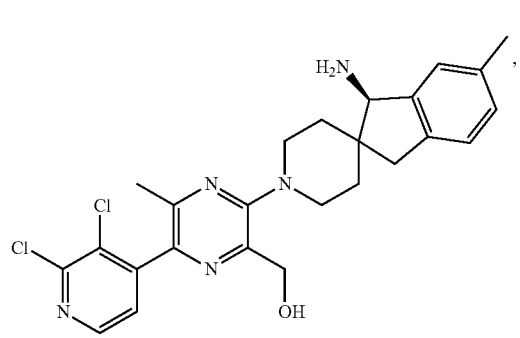
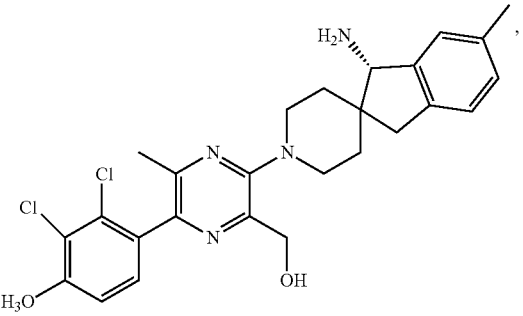
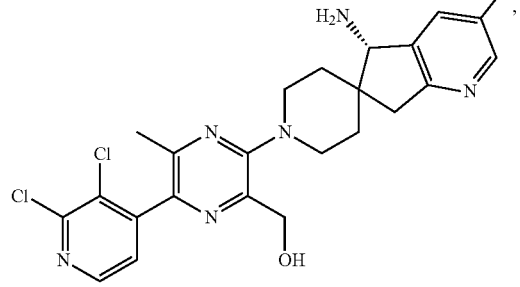
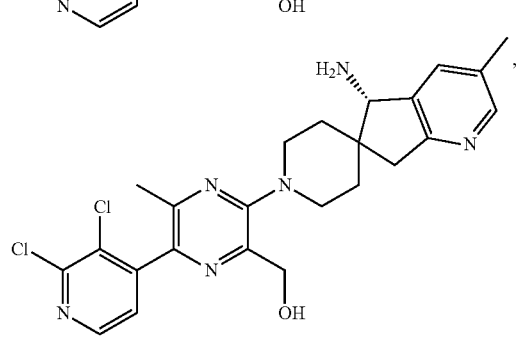
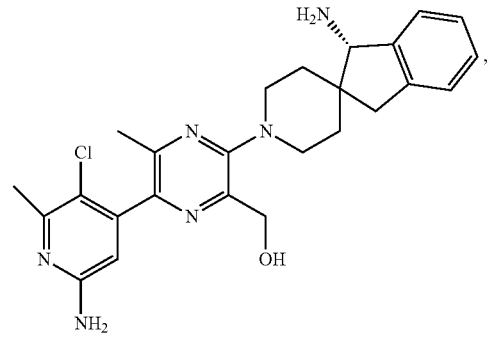

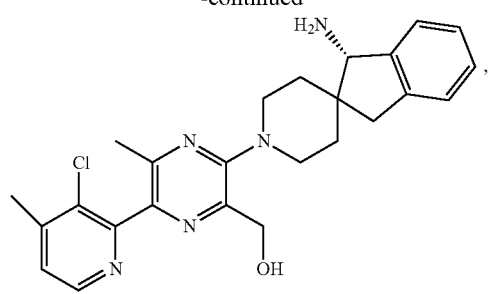
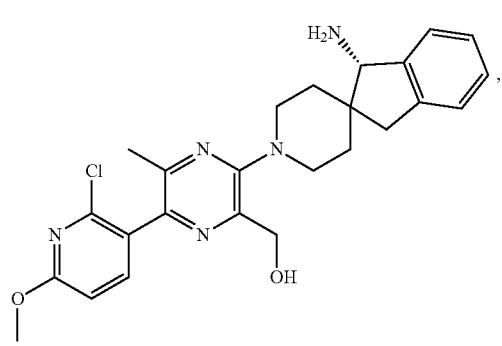
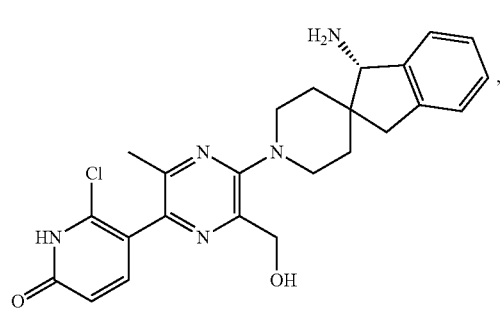
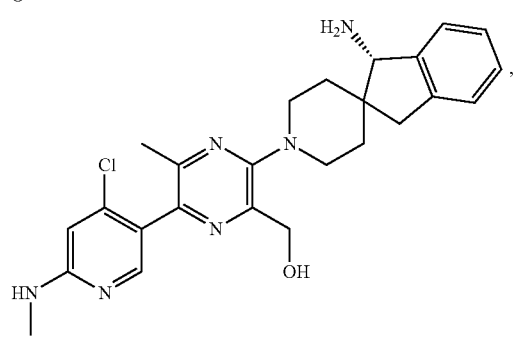
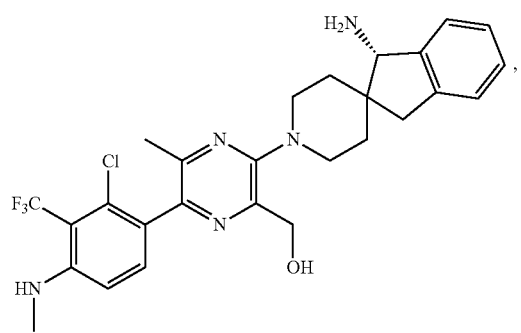
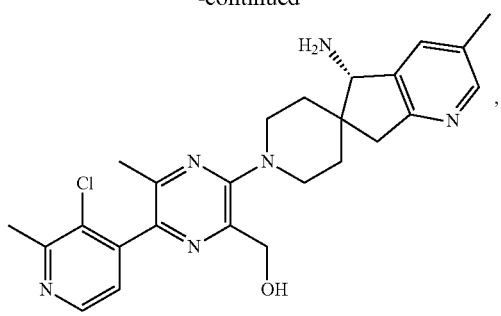
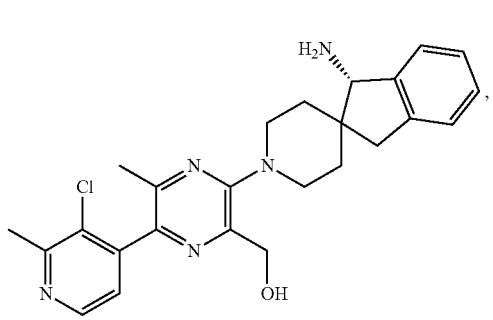
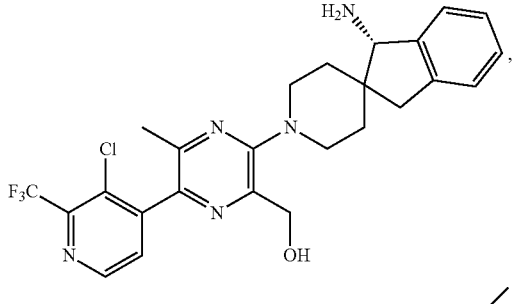
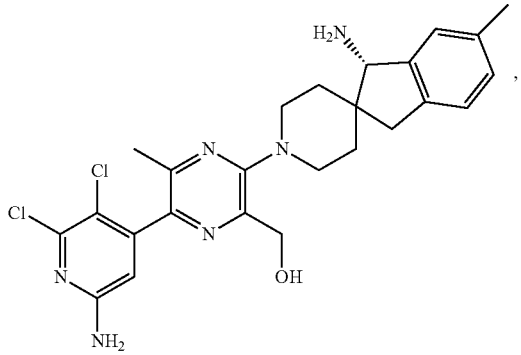
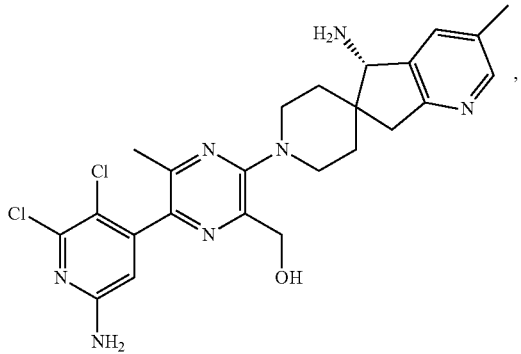

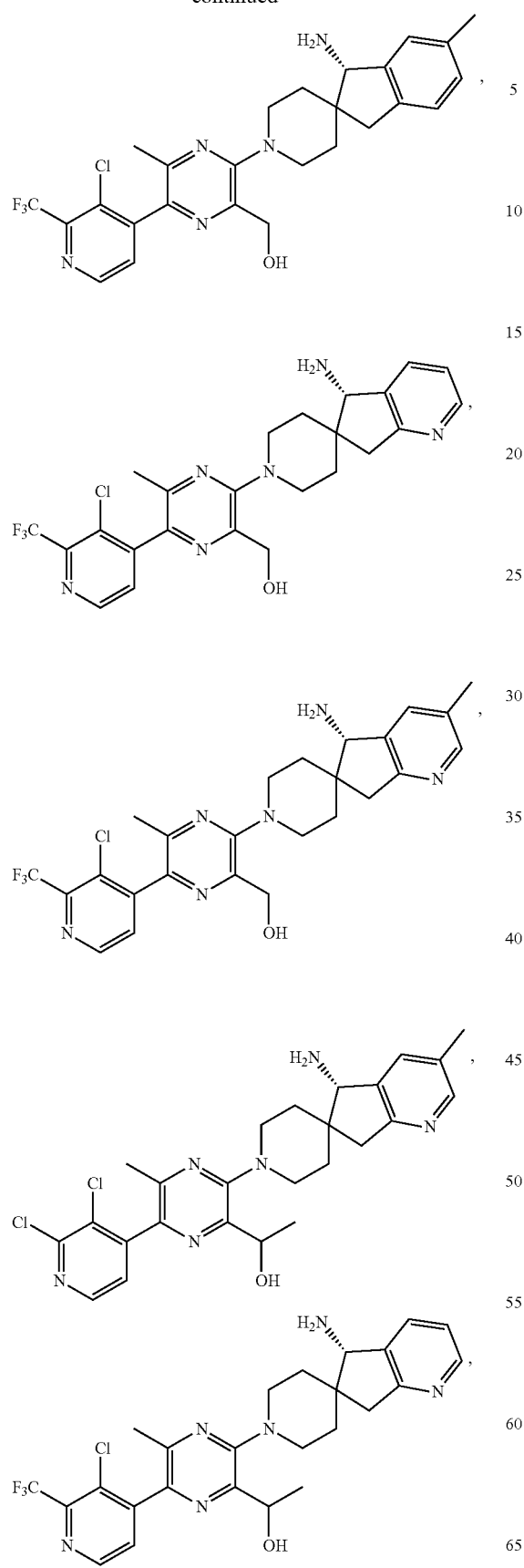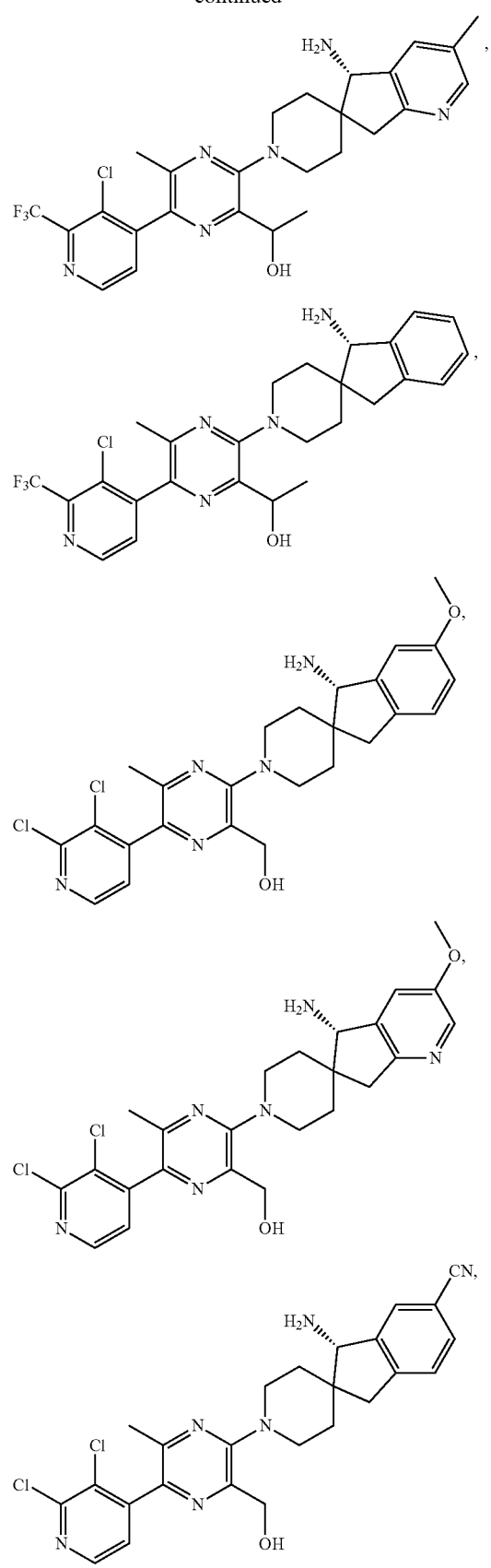

-continued

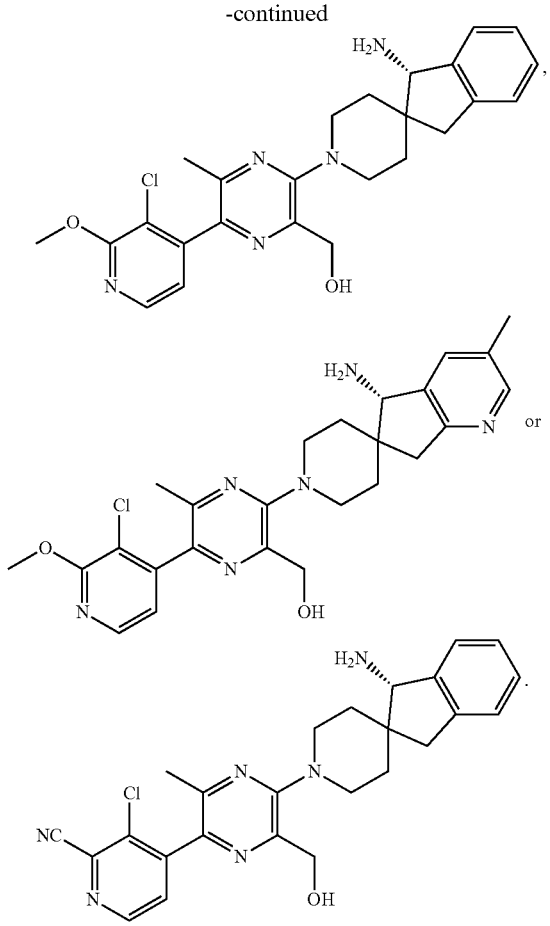

In another aspect, the present invention provides use of the optical isomer of SHP2 phosphatase allosteric inhibitor or the pharmaceutically acceptable salt thereof for preparation of a medicament for treating tumor diseases.

The advantage of the present invention lies in the SHP2 phosphatase allosteric inhibitor provided by the present invention has better inhibitory effect on tumor and lower hERG toxicity compared with existing SHP2 phosphatase allosteric inhibitors.

DETAILED DESCRIPTION OF THE INVENTION

The following non-limiting examples are illustrative and not to limit the invention in any way. Any variant, change and modification that do not deviate from the spirit of the present invention is within the scope of the invention.

In some embodiments, one or more compounds of the invention can be used in combination. The present compound of the invention can also be used in combination with other active agents for preparation of the SHP2 phosphatase allosteric inhibitor. If a combination of compounds are used, these compounds can be administered to the subject simultaneously, separately or sequentially.

In some embodiments, the inventive compound can be used in combination with one or more anticancer agent(s). Combined anticancer agents include but are not limited to those in specific embodiments.

The compounds of the present invention and their preparation and application are illustrated with the following examples, and the synthesis method is as described in scheme 1:

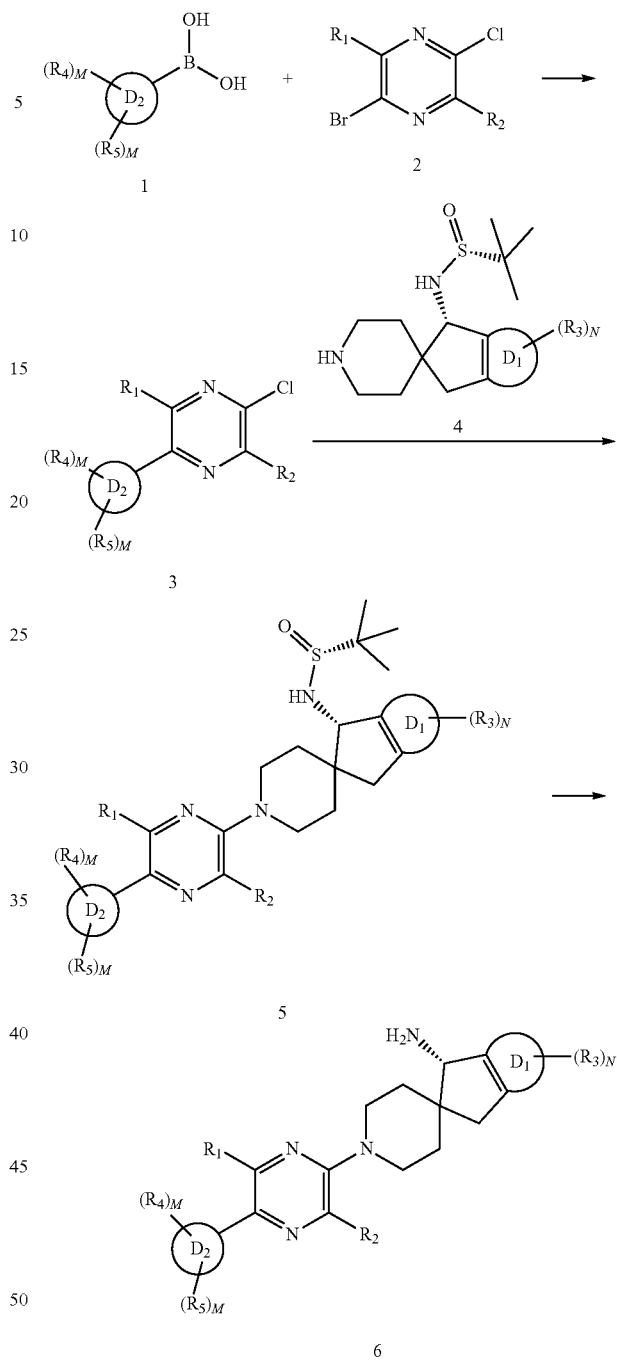

The present compounds can be prepared through the method of scheme 1. Each product obtained in scheme 1 can be prepared by conventional separation technology, which includes but is not limited to filtration, distillation, crystallization, chromatographic separation, etc. Starting materials can be synthesized by the person in the art or purchased from commercial suppliers (for example, but not limited to, Adrich or Sigma). These materials can be characterized by conventional means, such as physical constants and spectral data. For the compounds described in the present invention, a single isomer or a mixture thereof can be obtained by a synthetic method.

In scheme 1, intermediate 3 is obtained by a coupling reaction between materials 1 and 2 in the presence of proper catalyst, ligand and base. Intermediate 5 is obtained through substitution reaction by intermediate 3 and material 4 under alkaline condition, and the target compound 6 is obtained by removing protective group from intermediate 5 under acidic condition.

Unless otherwise specified, the temperature is centigrade. The reagents are from Sinopharm Chemical Reagent Beijing Co. Ltd., Alfa Aesar Co. Ltd, J&K Scientific Co. Ltd. and other commercial suppliers. Unless otherwise specified, these reagents can be used directly without further purification. Unless otherwise specified, the following reaction will be carried out at room temperature, in anhydrous solvent, under positive pressure of nitrogen or argon, or in a drying tube. A rubber stopper may be fixed at the top of reaction bottle, so that the substrates and reagents can be added through syringes; the glasswares have been dried and/or heated.

Unless otherwise specified, the chromatography silica gel with 200-300 meshes is purchased from Qingdao Haiyang Chemical Co. Ltd. Thin layer chromatographic silica gel prefabricated plate with commodity No. HSGF254 purchased from Yantai Chemical Industrial Research Institute is used as the thin layer chromatographic plate. MS is determined by LCQ Fleet™ (ESI) liquid chromatography-mass spectrometry (Thermo). SGW-3 automatic polarimeter (Shanghai Shenguang Instrument Co., Ltd.) is used for optical rotation measurement.

Unless otherwise specified, NCS (CAS No. 128-09-6) is purchased from Taicang Xinhu Chemical Co. Ltd.

Unless otherwise specified, [1,1'-bis(diphenylphosphino) ferrocene]dichloropalladium is purchased from Shenzhen Simeiquan Biotechnology Co. Ltd. (CAS No. 95464-05-4).

Unless otherwise specified, 2,3-dihydro-1H-inden-1-one, also called 1-indanone, is purchased from Shanghai Bide Pharmatech Ltd. (commodity No. BD31287).

Nuclear magnetic data (1H NMR) is processed by Varian instrument at 400 MHz. The solvents of $CDCl_3$, $CD_3OD$, $D_2O$, DMSO-$d_6$ and etc. are used for nuclear magnetic data, based on tetramethylsilane (0.00 ppm) or residual solvent ($CDCl_3$: 7.26 ppm; $CD_3OD$: 3.31 ppm; $D_2O$: 4.79 ppm; d6-DMSO: 2.50 ppm). When indicating the diversity of peak shapes, the following abbreviations denote different peak shapes: s (singlet), d (doublet), t (triplet), q (quartet), m (multiplet), br (broad signal), dd (doublet of doublets), dt (doublet of triplets). If the coupling constant is given, the unit will be Hertz (Hz).

| Abbreviation | |
| --- | --- |
| (Boc)₂O | di-tert-butyl dicarbonate |
| Cy₃PHBF₄ | tricyclohexylphosphonium tetrafluoroborate |
| DBU | 1,8-diazabicyclo[5.4.0]undec-7-ene |
| DMAP | 4-(Dimethylamino)pyridine |
| DMF | N,N-dimethylformamide |
| DMSO | Dimethyl Sulfoxide |
| DiFMUP | 6,8-difluoro-4-methylumbelliferyl phosphate |
| LDA | Lithium diisopropylamide |
| NBS | N-Bromosuccinimide |
| NCS | N-chlorosuccinimide |
| Pd(dppf)Cl₂ | [1,1'-bis(diphenylphosphino)ferrocene] dichloro palladium (II) |
| TEA | triethylamine |
| TFA | trifluoroacetic acid |
| THF | tetrahydrofuran |

Example 1

(S)-(3-(1-amino-1,3-dihydrospiro[indene-2,4'-piperidin]-1'-yl)-6-(2,3-dichlorophenyl)-5-methylpyrazin-2-yl)methanol (compound 1)

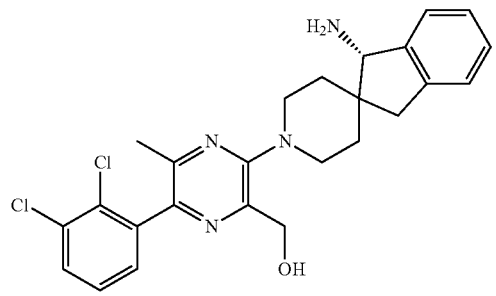 [SMILES: Cc1nc(N2CCC3(CC2)Cc2ccccc2[C@H]3N)c(CO)nc1-c1cccc(Cl)c1Cl]

Step 1: ethyl 3-hydroxy-5-methylpyrazine-2-carboxylate

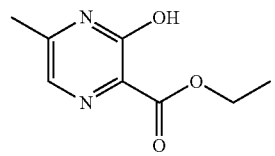

1,2-diaminopropane (11.0 g) was dissolved into anhydrous ethanol (200 mL), and cooled to 0° C. Diethyl ketomalonate (25.0 g) was added, the reaction temperature was raised to the room temperature and the solution was stirred for 2 hours, then the solution was refluxed overnight. Ice water (50 mL) was added into reaction solution, and extracted by dichloromethane (100 mL) for 3 times. Organic phase was dried by anhydrous sodium sulfate and crude product was obtained after removal of solvent. And final product (8.0 g) was obtained after purification through column chromatography (dichloromethane/methanol=30/1).

LC-MS, (ES, m/z): [M+H]⁺=183.

Step 2: ethyl 6-bromo-3-hydroxy-5-methylpyrazine-2-carboxylate

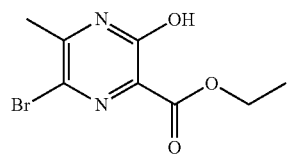

Ethyl 3-hydroxy-5-methylpyrazine-2-carboxylate (8.0 g) was dissolved into N,N-dimethylformamide (60 mL), and cooled to 0° C. NBS (7.86 g) was added into the solution, and the reaction was at room temperature overnight. Ice water (50 mL) was added into the reaction solution and extracted by dichloromethane (50 mL) for 3 times. Organic phase was washed with water (100 mL), and dried by anhydrous sodium sulfate. Crude product was obtained after removal of solvent. The final product was obtained (7.2 g) after purification with column chromatography (dichloromethane/methanol=100/1).

LC-MS, (ES, m/z): [M+H]⁺=261.

Step 3: ethyl 6-bromo-3-chloro-5-methylpyrazine-2-carboxylate

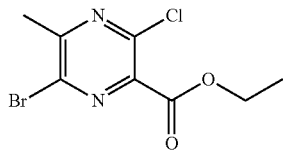

Triphenylphosphine (21.1 g) and NCS (10.8 g) were added into 1,4-dioxane (100 mL), and reacted at room temperature for 0.5 hour. Then ethyl 6-bromo-3-hydroxy-5-methylpyrazine-2-carboxylate (7.0 g) was added into the solution and reacted at 100° C. for 1 hour under N₂ protection. The reaction mixture was poured into water (300 mL) and extracted by dichloromethane (100 mL) for 3 times. The organic phase was dried by anhydrous sodium sulfate, and crude product was obtained after removal of solvent. Final product (5.1 g) was obtained after purification by column chromatography.

LC-MS, (ES, m/z): [M+H]⁺=279.

Step 4: ethyl 3-chloro-6-(2,3-dichlorophenyl)-5-methyl-pyrazine-2-carboxylate

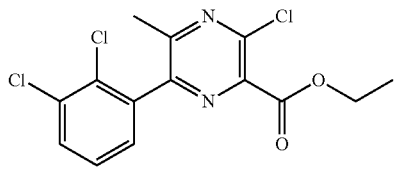 [SMILES: CCOC(=O)c1nc(-c2cccc(Cl)c2Cl)c(C)nc1Cl]

At room temperature, ethyl 6-bromo-3-chloro-5-methylpyrazine-2-carboxylate (2.0 g), 2,3-dichlorophenyl boronic acid (1.4 g), Pd(dppf)Cl₂ (525 mg), and potassium carbonate (2.0 g) were added into acetonitrile (100 mL). The mixture was raised to 90° C., and kept overnight under N₂ protection at this temperature. Then, the mixture was poured to water (200 mL), was extracted by dichloromethane (100 mL) for 3 times, dried by anhydrous sodium sulfate. Crude product was obtained after removal of solvent, and final product (0.98 g) was obtained after purification by column chromatography.

LC-MS, (ES, m/z): [M+H]⁺=345.

Step 5: tert-butyl 1-oxo-1,3-dihydrospiro[indene-2,4'-piperidine]-4'-carboxylate

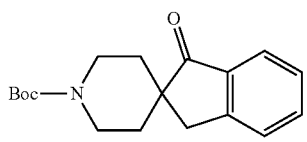 [SMILES: CC(C)(C)OC(=O)N1CCC2(CC1)Cc1ccccc1C2=O]

2,3-dihydro-1H-indene-1-one (13.0 g) was dissolved into N,N-dimethylformamide (200 mL), and cooled to 0° C. 60% sodium hydride (11.8 g) was added into the mixture. The mixture was raised to room temperature and stirred for 0.5 hour. Tertbutyl bis(2-chloroethyl)carbamate (23.8 g) was added and the mixture was raised to 60° C., and reacted overnight. Then, the mixture was poured into water (500 mL), and extracted by dichloromethane for 3 times. Organic phase was washed by water (300 mL), and dried by anhydrous sodium sulfate, and crude product was obtained by removal of solvent. After purification with column chromatography, (petroleum ether/ethyl acetate=5/1), final product (7.3 g) was obtained.

LC-MS, (ES, m/z): [M+H]⁺=302.

Step 6: (R)-1-tert-butyl 1-((tert-butylsufinyl)imino)-1,3-dihydrospiro[indene-2,4'-piperidine]-1'-carboxylate

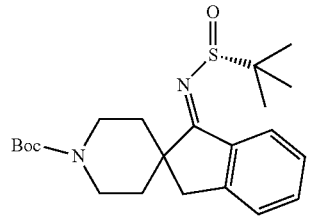 [SMILES: CC(C)(C)OC(=O)N1CCC2(CC1)Cc1ccccc1/C2=N\[S@](=O)C(C)(C)C]

tert-butyl 1-oxo-1,3-dihydrospiro[indene-2,4'-piperidine]-1'-carboxylate (7.0 g) and (R)-(+)-tert-butylsulfinamide (2.8 g) were added into tetraethoxy titanium (90 mL), and the solution was kept overnight at 90° C. The solution was diluted with water (500 mL) and dichloromethane (400 mL) and filtered with diatomaceous earth. The organic phase was dried by anhydrous sodium sulfate. After removal of solvent, the crude product (2.0 g) was obtained, which was used in the next step.

LC-MS, (ES, m/z): [M+H]⁺=404.

Step 7: (S)-tert-butyl 1-((R)-tert-butyl sufinamido)-1,3-dihydrospiro[indene-2,4'-piperidine]-1'-carboxylate

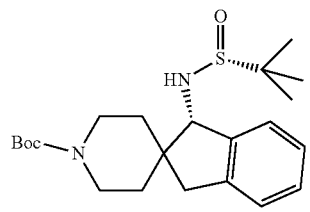 [SMILES: CC(C)(C)OC(=O)N1CCC2(CC1)Cc1ccccc1[C@H]2N[S@](=O)C(C)(C)C]

The crude (R)-1-tert-butyl 1-((tert-butylsufinyl)imino)-1,3-dihydrospiro[indene-2,4'-piperidine]-1'-carboxylate (2.0 g) was dissolved into tetrahydrofuran (40 mL), and cooled to −50° C. Sodium borohydride (752 mg) was added into the solution gradually and kept at the temperature for 2 hours. The solution was raised to the room temperature, and kept reaction overnight. Then, the reaction solution was poured into water (50 mL), extracted by dichloromethane (50 mL) for two times, and dried by anhydrous sodium sulfate. After removal of solvent, the crude product was obtained. The product was obtained after purification with column chromatography, and the target compound (1.1 g) was obtained by chiral resolution.

LC-MS, (ES, m/z): [M+H]$^+$=406.

Step 8: (R)—N—((S)-1,3-dihydrospiro[indene-2,4'-piperidin]-1-yl)-2-methylpropane-2-sulfinamide trifluoroacetate

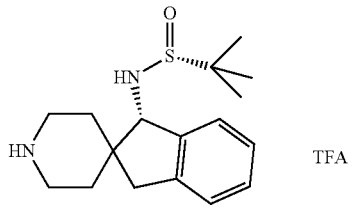 [SMILES: CC(C)(C)[S@@](=O)N[C@@H]1c2ccccc2CC12CCNCC2]

(S)-tert-butyl-1-((R)-1,1-dimethylethylsufinamido)-1,3-dihydrospiro [indene-2,4'-piperidine]-1'-carboxylate (1.0 g) was dissolved into dichloromethane (20 mL). Trifluoroacetic acid (4 mL) was added into the solution, and the solution was reacted at room temperature for an hour. After removal of solvent in vacuum, the crude product was obtained, which was directly used in the next step.

LC-MS, (ES, m/z): [M+H]$^+$=307.

Step 9: ethyl 6-(2,3-dichlorophenyl)-3-((S)-1-(R)-1,1-dimethylethylsulfinamido)-1,3-dihydrospiro[indene-2,4'-piperidin]-1'-yl)-5-methylpyrazine-2-carboxylate

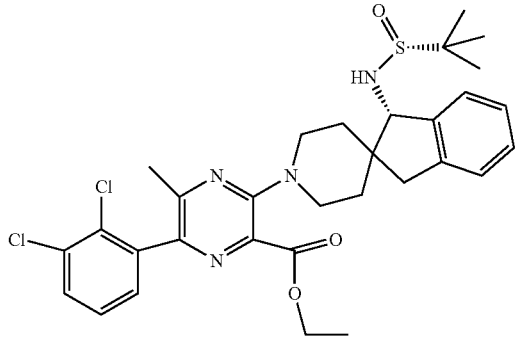 [SMILES: CCOC(=O)c1nc(-c2cccc(Cl)c2Cl)c(C)nc1N1CCC2(CC1)Cc1ccccc1[C@H]2N[S@](=O)C(C)(C)C]

At room temperature, ethyl 3-chloro-6-(2,3-dichlorophenyl)-5-methylpyrazine-2-carboxylate (100 mg), (R)—N—((S)-1,3-dihydrospiro[indene-2,4'-piperidin]-1-yl)-2-methylpropane-2-sulfinamide trifluoroacetate (200 mg) and potassium carbonate (200 mg) were added into N-methylpyrrolidine (5 mL) The solution was raised to 100° C. and kept overnight. Then, the solution was cooled to room temperature, and poured into water (20 mL). The solution was extracted by dichloromethane (10 mL) for 3 times, and the organic phase was dried by anhydrous sodium sulfate. After removal of solvent, the product (150 mg) was obtained by purification with column chromatography (dichloromethane/methanol=20/1). LC-MS, (ES, m/z): [M+H]$^+$=615.

Step 10: (S)-ethyl 3-(1-amino-1,3-dihydrospiro[indene-2,4'-piperidin]-1'-yl)-6-(2,3-dichlorophenyl)-5-methylpyrazine-2-carboxylate

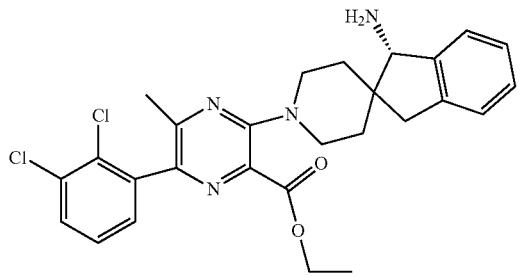 [SMILES: CCOC(=O)c1nc(-c2cccc(Cl)c2Cl)c(C)nc1N1CCC2(CC1)Cc1ccccc1[C@H]2N]

Ethyl 6-(2,3-dichlorophenyl)-3-((S)-1-(R)-1,1-dimethyl-ethylsulfinamido)-1,3-dihydrospiro[indene-2,4'-piperidin]-1'-yl)-5-methylpyrazine-2-carboxylate (150 mg) was added into the mixture of 1,4-dioxane (3 mL) and concentrated hydrochloric acid (1 mL) The solution was reacted at room temperature for 4 hours, poured into water (10 mL), neutralized by sodium bicarbonate to pH 7, and extracted by dichloromethane for 3 times. The organic phase was dried by anhydrous sodium sulfate. After removal of solvent and purification with column chromatography (dichloromethane/methanol=20/1), the final product (96 mg) was obtained.

LC-MS, (ES, m/z): [M+H]$^+$=511.

Step 11: (S)-(3-(1-amino-1,3-dihydrospiro[indene-2,4'-piperidin]-1'-yl)-6-(2,3-dichlorophenyl)-5-methylpyrazin-2-yl)methanol

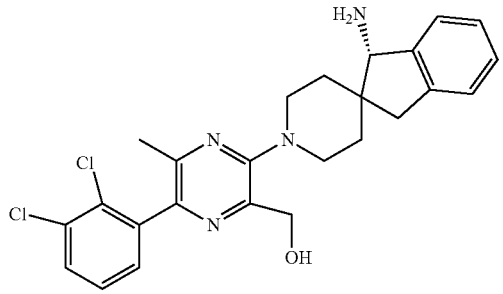 [SMILES: Cc1nc(N2CCC3(CC2)Cc2ccccc2[C@H]3N)c(CO)nc1-c1cccc(Cl)c1Cl]

(S)-ethyl 3-(1-amino-1,3-dihydrospiro[indene-2,4'-piperidin]-1'-yl)-6-(2,3-dichlorophenyl)-5-methylpyrazine-2-carboxylate (96 mg) was dissolved into tetrahydrofuran (10 mL) and cooled to −78° C. DIBAL-H (0.5 mL) was added into the solution and kept under the temperature for 1 hour. The solution was raised to 0° C. and kept being reacted for 2 hours. Then, the solution was raised to room temperature and kept being reacted overnight. Saturated ammonium chloride (5 mL) was added into the solution, and extracted with dichloromethane (10 mL) for 3 times. The organic phase was dried with anhydrous sodium sulfate. After removal of solvent and purification with column chromatography (dichloromethane/methanol=20/1), the product (10 mg) was obtained.

LC-MS, (ES, m/z): [M+H]$^+$=469.

$^1$H NMR (400 MHz, D6-DMSO) δ=7.74 (dd, J=7.9 Hz, 1.7, 1H), 7.49 (t, J=7.8 Hz, 1H), 7.44 (dd, J=7.6 Hz, 1.7 Hz, 1H), 7.39-7.33 (m, 1H), 7.26-7.15 (m, 3H), 5.29 (t, J=5.8 Hz, 1H), 4.53 (d, J=5.7 Hz, 2H), 3.98 (s, 1H), 3.80-3.70 (m,

2H), 3.15-3.05 (m, 3H), 2.69 (d, J=15.8 Hz, 1H), 2.20 (s, 3H), 1.92-1.82 (m, 2H), 1.57 (d, J=12.5 Hz, 1H), 1.27-1.24 (m, 1H).

Example 2

(S)-1-amino-1'-(5-(2,3-dichlorophenyl)-3-(hydroxymethyl)-6-methylpyrazin-2-yl)-1,3-dihydrospiro[indene-2,4'-piperidine]-6-carbonitrile (compound 2)

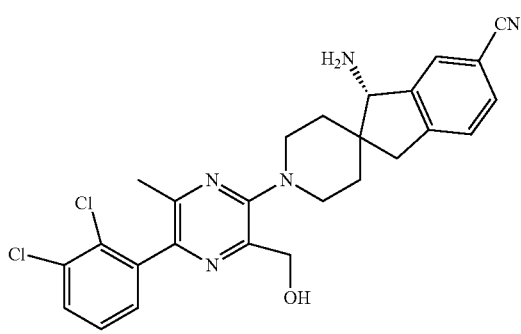 [SMILES: Cc1nc(N2CCC3(CC2)Cc2ccc(C#N)cc2[C@H]3N)c(CO)nc1-c1cccc(Cl)c1Cl]

Step 1: 1-tert-butyl 4-ethyl 4-(4-bromobenzyl)piperidine-1,4-dicarboxylate

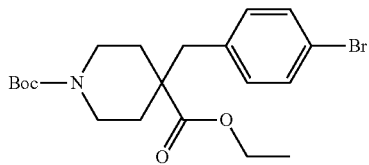 [SMILES: CCOC(=O)C1(Cc2ccc(Br)cc2)CCN(C(=O)OC(C)(C)C)CC1]

1-tert-butyl 4-ethylpiperidine-1,4-dicarboxylate (8.0 g) was dissolved into anhydrous tetrahydrofuran (200 mL) under the protection of N₂, and cooled to −78° C. LDA (2 mol/L, 16 mL) was added dropwisely to the solution and kept the reaction under the temperature for an hour. Then, 1-bromo-4-(bromomethyl) benzene (7.8 g) was added into the solution and kept reaction under the temperature for 3 hours. The solution was raised to room temperature and kept reacted overnight. After adding saturated ammonium chloride (50 mL) solution, the mixture was poured into water (400 mL), and extracted with dichloromethane (100 mL) for 3 times. The organic phase was dried by anhydrous sodium sulfate. The crude product was obtained after removal of solvent. After purification with column chromatography (dichloromethane/methanol=80/1), the product (14.0 g) was obtained.

LC-MS, (ES, m/z): [M+H]⁺=426.

Step 2: 4-(4-bromobenzyl)-1-(tert-butoxycarbonyl)piperidine-4-carboxylic acid

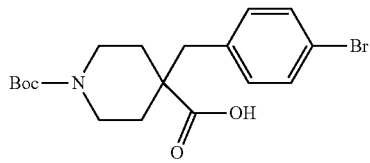 [SMILES: CC(C)(C)OC(=O)N1CCC(Cc2ccc(Br)cc2)(C(=O)O)CC1]

1-tert-butyl 4-ethyl 4-(4-bromobenzyl)piperidine-1,4-dicarboxylate (13.0 g) and sodium hydroxide (3.6 g) were dissolved into the mixture of ethanol (80 mL) and water (80 mL). The solution was refluxed overnight. The solution was cooled to room temperature, poured to water (200 mL) and neutralized to pH 6 with 2N hydrochloric acid. The solution was extracted with dichloromethane (100 mL) for 3 times, dried by anhydrous sodium sulfate. After removal of solvent, the crude product (16.5 g) was obtained, which can be used directly in the next step.

LC-MS, (ES, m/z): [M+H]⁺=396.

Step 3: tert-butyl 6-bromo-1-oxo-1,3-dihydrospiro[indene-2,4'-piperidine]-1'-carboxylate

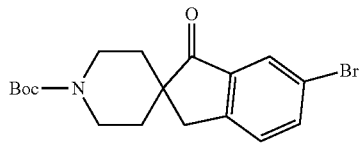 [SMILES: CC(C)(C)OC(=O)N1CCC2(CC1)Cc1ccc(Br)cc1C2=O]

The crude 4-(4-bromobenzyl)-1-(tert-butoxycarbonyl)piperidine-4-carboxylic acid (16.0 g) was added into polyphosphoric acid (100 mL). After the temperature was raised to 120° C., the solution was reacted for 0.5 hour. The solution was poured into an ice water mixture (300 mL), and neutralized by sodium hydroxide to pH 10. Di-tert-butyl dicarbonate (35.0 g) was added into the solution, and the solution was kept at room temperature overnight. The reaction solution was extracted by dichloromethane (100 mL) for 3 times, and dried by anhydrous sodium sulfate, and crude product was obtained after removal of solvent. After purification with column chromatography, the product (10.2 g) was obtained.

LC-MS, (ES m/z): [M+H]⁺=380.

Step 4: tert-butyl 6-cyano-1-oxo-1,3-dihydrospiro[indene-2,4'-piperidine]-1'-carboxylate

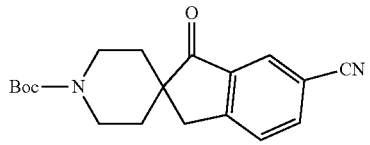 [SMILES: CC(C)(C)OC(=O)N1CCC2(CC1)Cc1ccc(C#N)cc1C2=O]

tert-butyl 6-bromo-1-oxo-1,3-dihydrospiro[indene-2,4'-piperidine]-1'-carboxylate (8.0 g), DBU (832 mg), tetra(triphenylphosphine) palladium (1.9 g) and potassium ferrocyanide (3.6 g) were added into the mixture of tertbutyl alcohol (50 mL) and water (50 mL), and the solution was kept at 90° C. under N₂ protection overnight. After the solution was cooled to room temperature, it was diluted by ethyl acetate (120 mL) and filtered. The filtered cake was washed by ethyl acetate (60 mL) Organic phases were combined, and dried by anhydrous sodium sulfate. After removal of solvent, the crude product was obtained. The product (3.2 g) was obtained after purification with column chromatography (dichloromethane/methanol=100/1).

LC-MS, (ES, m/z): [M+H]⁺=327.

Step 5: (R)-tert-butyl 1-((tert-butylsufinyl)imino)-6-cyano-1,3-dihydrospiro[indene-2,4'-piperidin]-1'-carboxylate

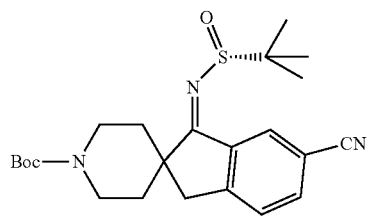 [SMILES: CC(C)(C)OC(=O)N1CCC2(CC1)Cc1ccc(C#N)cc1/C2=N\[S@](=O)C(C)(C)C]

The method was similar to the step 6 of example 1. The starting material was tert-butyl 6-cyano-1-oxo-1,3-dihydrospiro[indene-2,4'-piperidine]-1'-carboxylate (1.0 g) and the obtained crude product (1.2 g) was used directly in the next step.

LC-MS, (ES, m/z): [M+H]⁺=430

Step 6: (S)-tert-butyl 6-cyano-1-((R)-1,1-dimethylethylsulfinamido)-1,3-dihydrospiro[indene-2,4'-piperidine]-1'-carboxylate

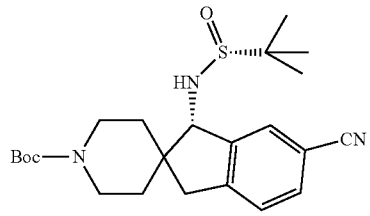 [SMILES: CC(C)(C)OC(=O)N1CCC2(CC1)Cc1ccc(C#N)cc1[C@H]2N[S@](=O)C(C)(C)C]

The method was similar to the step 7 of example 1. The starting material was (R)-tert-butyl 1-((tert-butylsufinyl)imino)-6-cyano-1,3-dihydrospiro[indene-2,4'-piperidine]-1'-carboxylate (1.0 g), and the crude product was obtained. After separation by chiral column, the target compound (1.1 g) was obtained.

LC-MS, (ES, m/z): [M+H]⁺=432.

Step 7: (R)—N—((S)-5-cyano-1,3-dihydrospiro[indene-2,4'-piperidin]-3-yl)-2-methylpropane-2-sulfinamide trifluoroacetate

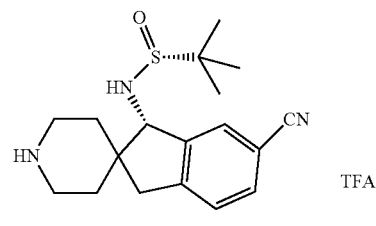 [SMILES: CC(C)(C)[S@@](=O)N[C@@H]1c2cc(C#N)ccc2CC12CCNCC2]

The method was similar to the step 8 of example 1. The crude product (98 mg) obtained from the starting material (S)-tert-butyl 6-cyano-1-((R)-1,1-dimethylethylsulfinamido)-1,3-dihydrospiro[indene-2,4'-piperidine]-1'-carboxylate (100 mg) was used directly in the next step.

LC-MS, (ES, m/z): [M+H]⁺=332.

Step 8: ethyl 3-((S)-6-cyano-1-((R)-1,1-dimethylethylsulfinamido)-1,3-dihydrospiro[indene-2,4'-piperidin]-1'-yl)-6-(2,3-dichlorophenyl)-5-methylpyrazine-2-carboxylate The method was similar to the step 9 of example 1. The product (150 mg) was obtained from ethyl 3-chloro-6-(2,3-dichlorophenyl)-5-methylpyrazine-2-carboxylate (100 mg) and (R)—N—((S)-5-cyano-1,3-dihydrospiro[indene-2,4'-piperidin]-3-yl)-2-methyl propane-2-sulfinamide trifluoroacetate (207 mg).

LC-MS, (ES, m/z): [M+H]⁺=640.

Step 9: (S)-ethyl-3-(1-amino-6-cyano-1,3-dihydrospiro[indene-2,4'-piperidin]-1'-yl)-6-(2,3-dichlorophenyl)-5-methylpyrazine-2-carboxylate

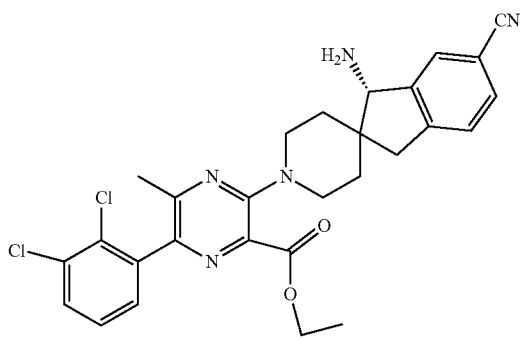 [SMILES: CCOC(=O)c1nc(-c2cccc(Cl)c2Cl)c(C)nc1N1CCC2(CC1)Cc1ccc(C#N)cc1[C@H]2N]

The method was similar to the step 10 of example 1. The product (70 mg) was obtained from the starting material ethyl 3-((S)-6-cyano-1-((R)-1,1-dimethylethylsulfinamido)-1,3-dihydrospiro[indene-2,4'-piperidin]-1'-yl)-6-(2,3-dichlorophenyl)-5-methylpyrazine-2-carboxylate (90 mg).

LC-MS, (ES, m/z): $[M+H]^+=536$.

Step 10: (S)-1-amino-1'-(5-(2,3-dichlorophenyl)-3-(hydroxymethyl)-6-methylpyrazin-2-yl)-1,3-dihydrospiro[indene-2,4'-piperidine]-6-carbonitrile

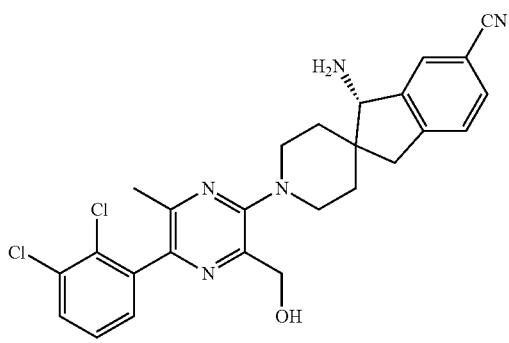 [SMILES: Cc1nc(N2CCC3(CC2)Cc2ccc(C#N)cc2[C@H]3N)c(CO)nc1-c1cccc(Cl)c1Cl]

(S)-ethyl-3-(1-amino-6-cyano-1,3-dihydrospiro[indene-2,4'-piperidin]-1'-yl)-6-(2,3-dichlorophenyl)-5-methylpyrazine-2-carboxylate (26 mg) was added into tetrahydrofuran (2 mL), and cooled to 0° C. Lithium borohydride (26 mg) was added into the solution, and the solution was kept at that temperature for 2 hours. The solution was reacted at room temperature overnight. Water (5 mL) was added into the solution and the mixture was extracted by dichloromethane (10 mL) for 3 times. The organic phase was dried by anhydrous sodium sulfate. After removal of solvent and purification by column chromatography, the product (3 mg) was obtained.

LC-MS, (ES, m/z): $[M+H]^+=494$.

$^1$H NMR (400 MHz, D6-DMSO) δ=8.02 (s, 1H) 7.78-7.70 (m, 2H), 7.53-7.41 (m, 3H), 5.31 (br 1H), 4.53 (s, 2H), 3.84-3.68 (m, 3H), 3.23-2.91 (m, 3H), 2.20 (s, 3H), 2.10-1.98 (m, 1H), 1.50-1.45 (m, 4H).

Example 3

(S)—N-(1-amino-1'-(5-(2,3-dichlorophenyl)-3-(hydroxymethyl)-6-methylpyrazin-2-yl)-1,3-dihydrospiro[indene-2,4'-piperidin]-6-yl) methanesulfonamide (compound 3)

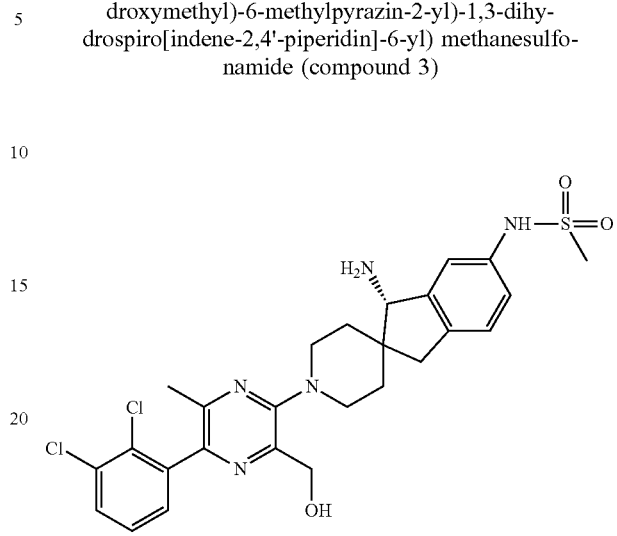

Step 1: tert-butyl 6-(methylsulfonamido)-1-oxo-1,3-dihydrospiro[indene-2,4'-piperidine]-1'-carboxylate

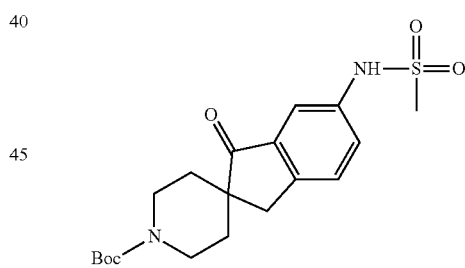

tert-butyl 6-bromo-1-oxo-1,3-dihydrospiro[indene-2,4'-piperidine]-1'-carboxylate (534 mg), methanesulfonamide (740 mg), $N^1,N^2$-dimethylethane-1,2-diamine (170 mg), and cuprous iodide (147 mg) were added into 1,4-dioxane (20 mL), and the solution was raised to 110° C. under $N_2$ protection, and reacted overnight. The solution was poured into water (50 mL), and extracted by dichloromethane (30 mL) for 3 times. The organic phase was dried by anhydrous sodium sulfate. After removal of solvent and purification by column chromatography, the product (410 mg) was obtained.

LC-MS, (ES m/z): $[M+H]^+=395$.

Step 2: (R)-tert-butyl 1-((tert-butylsulfinyl)imino)-6-(methylsulfonamido)-1,3-dihydrospiro[indene-2,4'-piperidine]-1'-carboxylate

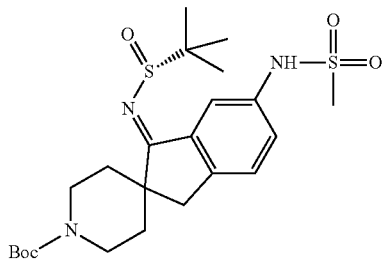 [SMILES: CC(C)(C)OC(=O)N1CCC2(CC1)Cc1ccc(NS(C)(=O)=O)cc1/C2=N\[S@](=O)C(C)(C)C]

The method was similar to the step 6 of example 1. The crude product (250 mg) was obtained from the starting material tert-butyl 6-(methylsulfonamido)-1-oxo-1,3-dihydrospiro[indene-2,4'-piperidine]-1'-carboxylate (300 mg) and was used directly in the next step.
LC-MS, (ES m/z): [M+H]$^+$=498.

Step 3: (S)-tert-butyl 1-((R)-1,1-dimethylethylsulfinamido)-6-(methylsulfonamido)-1,3-dihydrospiro[indene-2,4'-piperidine]-1'-carboxylate

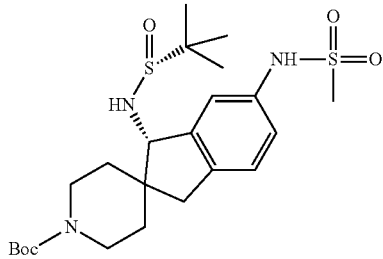 [SMILES: CC(C)(C)OC(=O)N1CCC2(CC1)Cc1ccc(NS(C)(=O)=O)cc1[C@H]2N[S@](=O)C(C)(C)C]

The method was similar to the step 7 of example 1. The target product (200 mg) was obtained from the starting material (R)-tert-butyl 1-((tert-butyl sulfinyl) imino)-6-(methylsulfonamido)-1,3-dihydrospiro[indene-2,4'-piperidine]-1'-carboxylate (250 mg).
LC-MS, (ES m/z): [M+H]$^+$=500.

Step 4: N—((S)-1-((R)-1,1-dimethylethylsulfinamido)-1,3-dihydrospiro[indene-2,4'-piperidin]-6-yl)methanesulfonamide trifluoroacetate

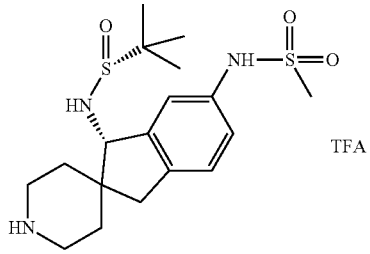 [SMILES: CC(C)(C)[S@@](=O)N[C@@H]1c2cc(NS(C)(=O)=O)ccc2CC12CCNCC2]

The method was similar to the step 8 of example 1, the crude product (180 mg) obtained from the starting material (S)-tert-butyl 1-((R)-1,1-dimethylethylsulfinamido)-6-(methylsulfonamido)-1,3-dihydro spiro[indene-2,4'-piperidine]-1'-carboxylate (200 mg) was used directly in the next step.
LC-MS, (ES m/z): [M+H]$^+$=400.

Step 5: ethyl 6-(2,3-dichlorophenyl)-3-((S)-1'-((R)-1,1-dimethylethylsulfinamido)-6'-(methylsulfonamido)-1',3'-dihydrospiro[indene-2,4'-piperidine]-1'-yl)-5-methylpyrazine-2-carboxylate

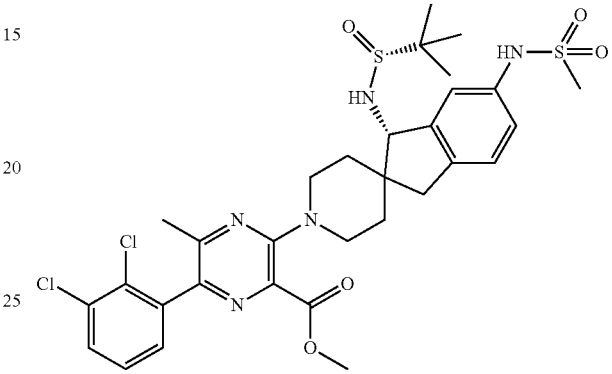

The method was similar to the step 9 of example 1. The product (90 mg) was obtained from the starting materials ethyl 3-chloro-6-(2,3-dichlorophenyl)-5-methyl-pyrazine-2-carboxylate (156 mg) and N—((S)-1-((R)-1,1-dimethylethylsulfinamido)-1,3-dihydrospiro[indene-2,4'-piperidin]-6-yl)methanesulfonamide trifluoroacetate (180 mg).
LC-MS, (ES m/z): [M+H]$^+$=708.

Step 6: (S)-ethyl 3-(1'-amino-6'-(methylsulfonamido)-1',3'-dihydrospiro[indene-2,4'-piperidine]-1'-yl)-6-(2,3-dichlorophenyl)-5-methylpyrazine-2-carboxylate

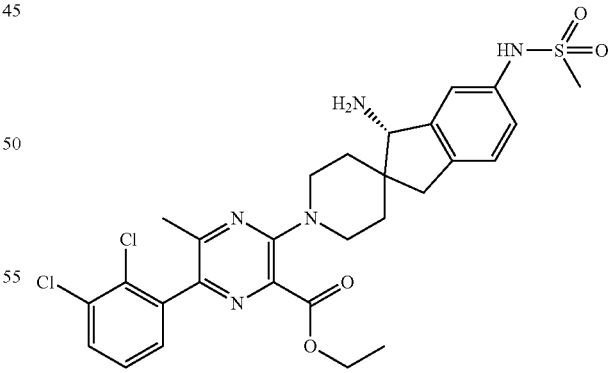

The method was similar to the step 10 of example 1. The product (30 mg) was obtained from the starting material ethyl 6-(2,3-dichlorophenyl)-3-((S)-1'-(R)-1,1-dimethylethylsulfinamido)-6'-(methylsulfonamido)-1',3'-dihydrospiro[indene-2,4'-piperidine]-1'-yl)-5-methyl pyrazine-2-carboxylate (90 mg).
LC-MS, (ES m/z): [M+H]$^+$=605.

Step 7: (S)—N-(1'-amino-1'-(5-(2,3-dichlorophenyl)-3-(hydroxymethyl)-6-methylpyrazin-2-yl)-1,3-dihydrospiro[indene-2,4'-piperidin]-6-yl)methanesulfonamide

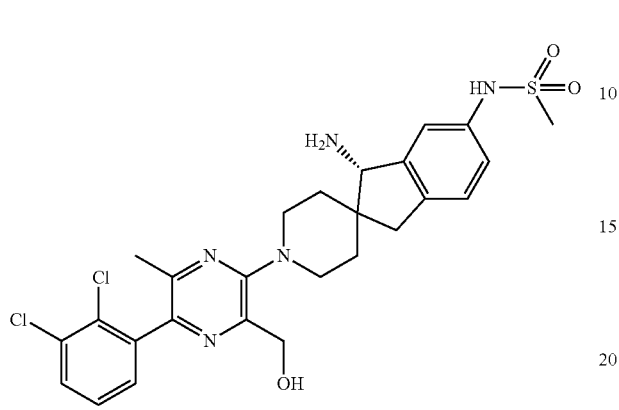

The method was similar to the step 10 of example 2. The product (9 mg) was obtained from the starting material (S)-ethyl 3-(1-amino-6-(methyl sulfonamido)-1,3-dihydrospiro[indene-2,4'-piperidine]-1'-yl)-6-(2,3-dichlorophenyl)-5-methylpyrazine-2-carboxylate (28 mg).

LC-MS, (ES m/z): [M+H]$^+$=562.

$^1$H NMR (400 MHz, D6-DMSO) δ=9.59 (br, 1H) 7.74 (dd, J=7.9 Hz, 1.7 Hz, 1H), 7.60 (t, J=3.5 Hz, 1H), 7.49 (t, J=7.8 Hz, 1H), 7.43 (m, 1.7, 1H), 7.19 (d, J=8.1 Hz, 1H), 7.08 (m, 2.01H), 5.28 (br, 1H), 4.53 (s, 2H), 3.75-3.65 (m, 3H), 3.14-3.01 (m, 3H), 2.98 (s, 3H), 2.78 (d, J=15.7 Hz, 1H), 2.20 (s, 3H), 2.09-1.89 (m, 2H), 1.57-1.29 (m, 2H).

Example 4

(S)-2-(1-amino-1'-(5-(2,3-dichlorophenyl)-3-(hydroxymethyl)-6-methylpyrazin-2-yl)-1,3-dihydrospiro[indene-2,4'-piperidin]-6-yl)propan-2-ol (compound 4)

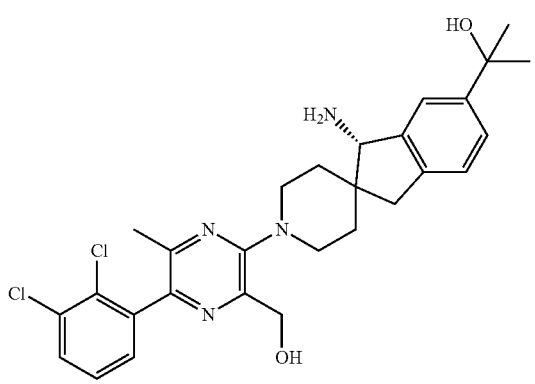 [SMILES: Cc1nc(N2CCC3(CC2)Cc2ccc(C(C)(C)O)cc2[C@H]3N)c(CO)nc1-c1cccc(Cl)c1Cl]

Step 1: (S)-tert-butyl 6-acetyl-1-((R)-1,1-dimethylethylsulfinamido)-1,3-dihydrospiro[indene-2,4'-piperidine]-1'-carboxylate

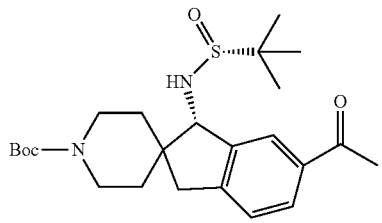 [SMILES: CC(=O)c1ccc2c(c1)[C@@H](N[S@](=O)C(C)(C)C)C1(CCN(C(=O)OC(C)(C)C)CC1)C2]

(S)-1-(R)-tert-butyl 1-((tert-butylsulfinyl)imino)-6-cyano-1,3-dihydrospiro[indene-2,4'-piperidine]-1'-carboxylate (2.1 g) was added into anhydrous tetrahydrofuran (20 mL) under the protection of N$_2$ and cooled to −50° C. Methylmagnesium bromide (2 mol/L, 10 mL) was added dropwisely into the solution. The solution was kept reacted at the temperature for 2 hours, then raised to room temperature and reacted overnight. The solution was poured into water (50 mL), and extracted by dichloromethane (50 mL) for 3 times. The organic phase was dried by anhydrous sodium sulfate. After removal of solvent and purification by column chromatography (petroleum/ethyl acetate=5/1), the product was obtained (700 mg).

LC-MS, (ES m/z): [M+H]$^+$=449.

Step 2: (R)—N—((S)-5-(2-hydroxypropan-2-yl)-1,3-dihydrospiro[indene-2,4'-piperidin]-3-yl)-2-methylpropane-2-sulfinamide

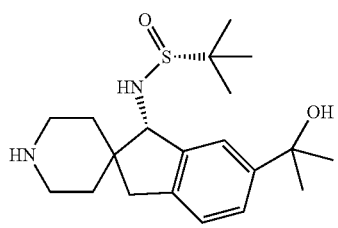 [SMILES: CC(C)(O)c1ccc2c(c1)[C@@H](N[S@](=O)C(C)(C)C)C1(CCNCC1)C2]

(S)-tert-butyl 6-acetyl-1-((R)-1,1-dimethylethylsulfinamido)-1,3-dihydrospiro[indene-2,4'-piperidine]-1'-carboxylate (700 mg) was dissolved into anhydrous tetrahydrofuran (10 mL) under the protection of N$_2$, and cooled to −78° C. Methyl lithium (2.4 mol/L, 1.6 mL) was added dropwisely into the solution. The solution was reacted at that temperature for 2 hours. The temperature was raised to room temperature and the solution was kept at the temperature overnight. Saturated ammonium chloride (20 mL) was added into the solution. The solution was extracted by dichloromethane (20 mL) for 3 times, and the organic phase was extracted for 3 times. The organic phase was dried by anhydrous sodium sulfate. After removal of solvent and purification by column chromatography (dichloromethane/methanol=20/1), the product (420 mg) was obtained.

LC-MS, (ES m/z): [M+H]$^+$=365.

Step 3: ethyl 6-(2,3-dichlorophenyl)-3-((S)-1-((R)-1,1-dimethyl ethylsulfinamido)-6-(2-hydroxypropan-2-yl)-1,3-dihydrospiro[indene-2,4'-piperidin]-1'-yl)-5-methylpyrazine-2-carboxylate

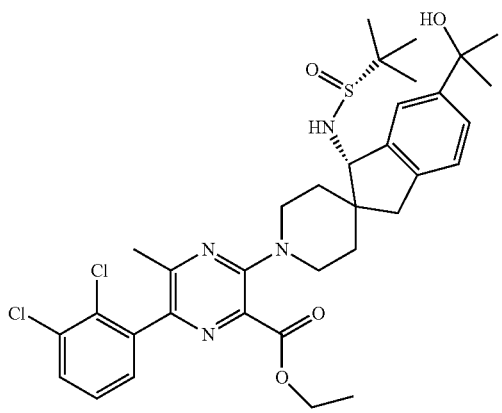 [SMILES: CCOC(=O)c1nc(-c2cccc(Cl)c2Cl)c(C)nc1N1CCC2(CC1)Cc1ccc(C(C)(C)O)cc1[C@H]2N[S@](=O)C(C)(C)C]

The method was similar to the step 9 of example 1. The product (120 mg) was obtained from the starting material ethyl 3-chloro-6-(2,3-dichlorophenyl)-5-methylpyrazine-2-carboxylate (320 mg) and (R)—N— ((S)-5-(2-hydroxypropan-2-yl)-1,3-dihydrospiro[indene-2,4'-piperidin]-3-yl)-2-methylpropane-2-sulfinamide (400 mg).

LC-MS, (ES m/z): [M+H]$^+$=673.

Step 4: (S)-ethyl 3-(1-amino-6-(2-hydroxypropan-2-yl)-1,3-dihydrospiro[indene-2,4'-piperidin]-1'-yl)-6-(2,3-dichlorophenyl)-5-methylpyrazine-2-carboxylate

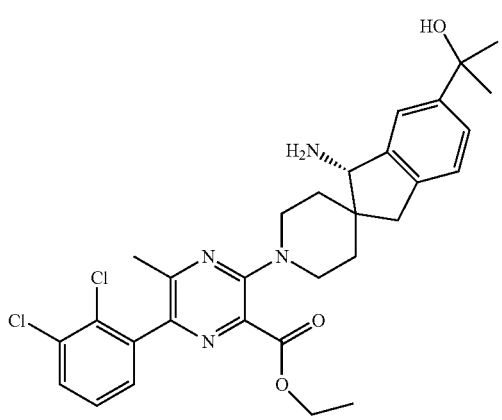 [SMILES: CCOC(=O)c1nc(-c2cccc(Cl)c2Cl)c(C)nc1N1CCC2(CC1)Cc1ccc(C(C)(C)O)cc1[C@H]2N]

The method was similar to step 10 of example 1. The product (40 mg) was obtained from the starting material ethyl 6-(2,3-dichlorophenyl)-3-((S)-1-((R)-1,1-dimethylethylsulfinamido)-6-(2-hydroxypropan-2-yl)-1,3-dihydrospiro[indene-2,4'-piperidin]-1'-yl)-5-methylpyrazine-2-carboxylate.

LC-MS, (ES m/z): [M+H]$^+$=569.

Step 5: (S)-2-(1-amino-1'(5-(2,3-dichlorophenyl)-3-(hydroxymethyl)-6-methylpyrazin-2-yl)-1,3-dihydrospiro[indene-2,4'-piperidin]-6-yl)propan-2-ol The method was similar to the step 10 of example 2. The product (6 mg) was obtained from the starting material (S)-ethyl 3-(1-amino-6-(2-hydroxypropan-2-yl)-1,3-dihydrospiro[indene-2,4'-piperidin]-1'-yl)-6-(2,3-dichlorophenyl)-5-methylpyrazine-2-carboxylate (38 mg).

LC-MS, (ES, m/z): [M+H]$^+$=527.

$^1$H NMR (400 MHz, D6-DMSO) δ=7.81 (s, 1H), 7.75 (dd, J=8.0 Hz, 2.0 Hz, 1H), 7.51-7.36 (m, 3H), 7.14 (d, J=7.9 Hz, 1H), 5.28 (br 1H), 4.93 (br, 1H), 4.53 (s, 2H), 3.74-3.65 (m, 3H), 3.10-3.04 (m, 3H), 2.78 (d, J=16 Hz, 1H)(s, 3H), 2.20 (s, 3H), 2.11-1.93 (m, 1H), 1.57-1.44 (m, 3H), 1.43 (d, J=7.5 Hz, 6H).

Example 5

(S)-1-amino-1'-(5-(2,3-dichlorophenyl)-3-(hydroxymethyl)-6-methylpyrazin-2-yl)-1,3-dihydrospiro[indene-2,4'-piperidine]-6-carboxamide (compound 5)

Step 1: (S)-tert-butyl 6-carbamoyl-1-((R)-1,1-dimethylethyl sulfinamido)-1,3-dihydrospiro[indene-2,4'-piperidine]-1'-carboxylate

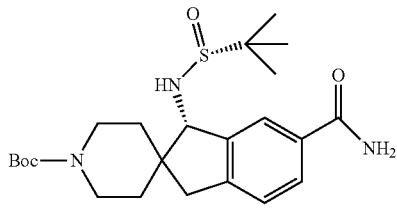 [SMILES: CC(C)(C)OC(=O)N1CCC2(CC1)Cc1ccc(C(N)=O)cc1[C@H]2N[S@](=O)C(C)(C)C]

(S)-tert-butyl 1-(R)-((tert-butylsufinyl)imino)-6-cyano-1,3-dihydro spiro[indene-2,4'-piperidin]-1'-carboxylate (400 mg) was added into the mixture of hydrogen peroxide (2 mL) and 1N sodium hydroxide solution (5 mL). The solution was protected by $N_2$, and reacted at 60° C. for 2 hours.

Then, the solution was poured into water (10 mL), and extracted with dichloromethane (20 mL) for 3 times. The organic phase was dried by anhydrous sodium sulfate. After removal of solvent and purification with column chromatography (petroleum ether/ethyl acetate=5/1), the product (310 mg) was obtained.

LC-MS, (ES, m/z): [M+H]$^+$=450.

Step 2: (S)-1-((R)-1,1-dimethylethylsufinamido)-1,3-dihydro spiro[indene-2,4'-piperidine]-6-carboxamide trifluoroacetate

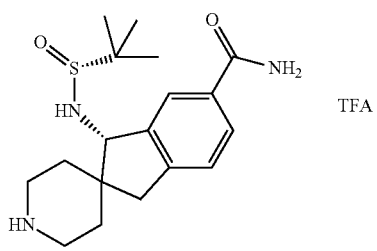 [SMILES: CC(C)(C)[S@@](=O)N[C@@H]1c2cc(C(N)=O)ccc2CC12CCNCC2]

The method was similar to the step 8 of example 1. The crude product (210 mg) obtained from the starting material (S)-tert-butyl 6-carbamoyl-1-((R)-1,1-dimethylethylsulfinamido)-1,3-dihydrospiro[indene-2,4'-piperidine]-1'-carboxylate (300 mg) was directly used in the next step.

LC-MS, (ES, m/z): [M+H]$^+$=350.

Step 3: ethyl 3-((S)-6-carbamoyl-1-((R)-1,1-dimethylethyl sulfinamido)-1,3-dihydrospiro[indene-2,4'-piperidin]-1'-yl)-6-(2,3-dichlorophenyl)-5-methylpyrazine-2-carboxylate

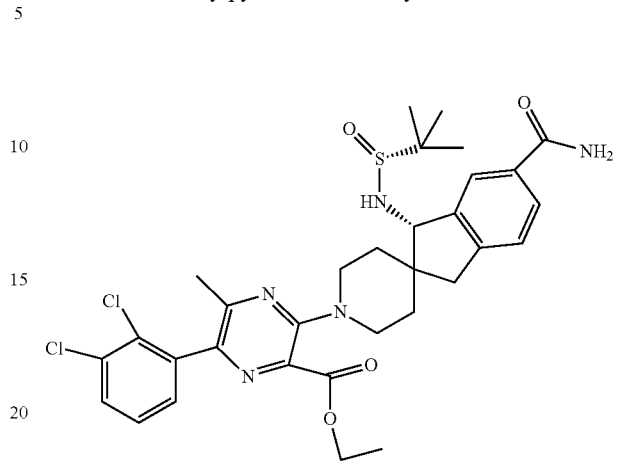

The method was similar to the step 9 of example 1. The product (100 mg) was obtained from the starting materials ethyl 3-chloro-6-(2,3-dichlorophenyl)-5-methyl-pyrazine-2-carboxylate (197 mg) and (S)-1-((R)-1,1-dimethylethylsufinamido)-1,3-dihydrospiro[indene-2,4'-piperidine]-6-carboxamide trifluoroacetate (200 mg).

LC-MS, (ES, m/z): [M+H]$^+$=658.

Step 4: (S)-ethyl 3-(1-amino-6-carbamoyl-1,3-dihydrospiro[indene-2,4'-piperidin]-1'-yl)-6-(2,3-dichlorophenyl)-5-methylpyrazine-2-carboxylate

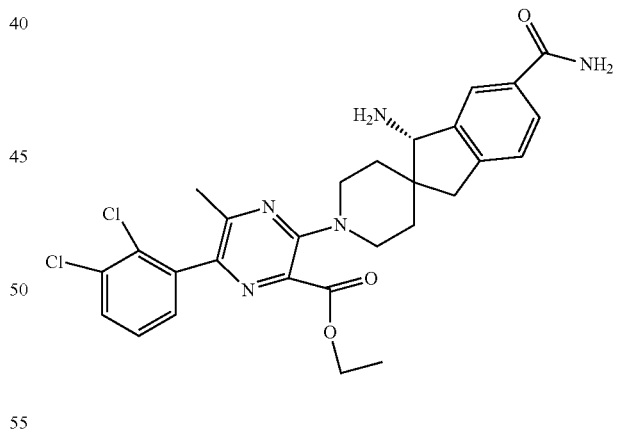

The method was similar to the step 10 of example 1. The product (35 mg) was obtained from the starting material ethyl 3-((S)-6-carbamoyl-1-((R)-1,1-dimethylethylsulfinamido)-1,3-dihydrospiro[indene-2,4'-piperidin]-1'-yl)-6-(2,3-dichlorophenyl)-5-methylpyrazine-2-carboxylate (100 mg).

LC-MS, (ES,m/z): [M+H]$^+$=554.

Step 5: (S)-1-amino-1'-(5-(2,3-dichlorophenyl)-3-(hydroxymethyl)-6-methylpyrazin-2-yl)-1,3-dihydrospiro[indene-2,4'-piperidine]-6-carboxamide

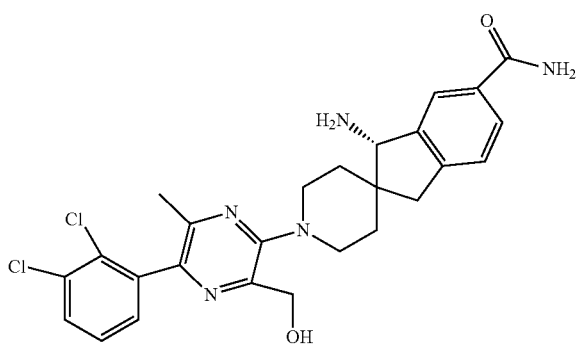 [SMILES: Cc1nc(N2CCC3(CC2)Cc2ccc(C(N)=O)cc2[C@H]3N)c(CO)nc1-c1cccc(Cl)c1Cl]

The method was similar to step 10 of example 2. The product (2 mg) was obtained from the starting material (S)-ethyl 3-(1-amino-6-carbamoyl-1,3-dihydrospiro[indene-2,4'-piperidin]-1'-yl)-6-(2,3-dichlorophenyl)-5-methylpyrazine-2-carboxylate (13 mg).

LC-MS, (ES, m/z): [M+H]⁺=512.

¹H NMR (400 MHz, D6-DMSO) δ=8.37 (S, 1H), 8.20 (s, 1H), 7.87 (d, J=10.4 Hz, 1H), 7.76 (dd, J=7.8 Hz, 1.6 Hz, 1H), 7.75 (S, 1H), 7.51-7.47 (m, 1H), 7.46 (dd, J=15.2 Hz, 4.8 Hz, 1H), 7.29 (d, J=7.9 Hz, 1H), 5.59-5.31 (m, 3H), 4.54 (s, 2H), 3.78-3.65 (m, 3H), 3.18-3.04 (m, 3H), 2.85 (d, J=16.1 Hz, 1H), 2.20 (s, 3H), 2.12-1.88 (m, 1H), 1.61-1.41 (m, 3H).

Example 6

(S)-3-(1-amino-1,3-dihydrospiro[indene-2,4'-piperidin]-1'-yl)-6-(2,3-dichlorophenyl)-5-methylpyrazine-2-carboxamide (compound 6)

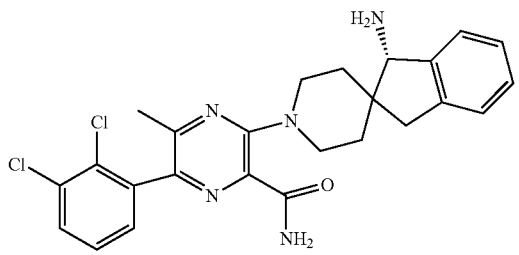 [SMILES: Cc1nc(N2CCC3(CC2)Cc2ccccc2[C@H]3N)c(C(N)=O)nc1-c1cccc(Cl)c1Cl]

Step 1: 3-chloro-6-(2,3-dichlorophenyl)-5-methylpyrazine-2-carboxamide

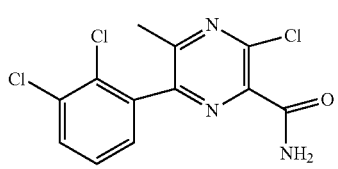 [SMILES: Cc1nc(Cl)c(C(N)=O)nc1-c1cccc(Cl)c1Cl]

Ethyl 3-chloro-6-(2,3-dichlorophenyl)-5-methylpyrazine-2-carboxylate (80 mg) was added into methanol (2 mL). Under N₂ protection, the solution was reacted overnight and white solid was precipitated. After filtering and washing, the product (60 mg) was obtained.

LC-MS, (ES, m/z): [M+H]⁺=315.

Step 2: 6-(2,3-dichlorophenyl)-3-((S)-1-((R)-1,1-dimethylethylsulfinamido)-1,3-dihydrospiro[indene-2,4'-piperidin]-1'-yl)-5-methylpyrazine-2-carboxamide

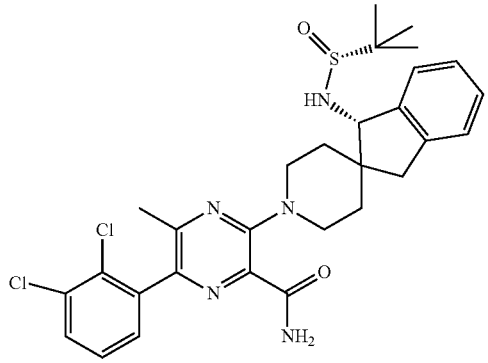 [SMILES: Cc1nc(N2CCC3(CC2)Cc2ccccc2[C@H]3N[S@](=O)C(C)(C)C)c(C(N)=O)nc1-c1cccc(Cl)c1Cl]

The method was similar to the step 9 of example 1. The product (30 mg) was obtained from the starting materials 3-chloro-6-(2,3-dichlorophenyl)-5-methylpyrazine-2-carboxamide (60 mg) and (R)—N—((S)-1,3-dihydrospiro[indene-2,4'-piperidin]-1-yl)-2-methylpropane-2-sulfinamide trifluoroacetate (200 mg).

LC-MS, (ES, m/z): [M+H]⁺=586

Step 3: (S)-3-(1-amino-1,3-dihydrospiro[indene-2,4'-piperidin]-1'-yl)-6-(2,3-dichlorophenyl)-5-methylpyrazine-2-carboxamide The method was similar to the step 10 of example 1. The product (4 mg) was obtained from the starting material 6-(2,3-dichlorophenyl)-3-((S)-1-((R)-1,1-dimethylethylsulfinamido)-1,3-dihydrospiro[indene-2,4'-piperidin]-1'-yl)-5-methylpyrazine-2-carboxamide (30 mg).

LC-MS, (ES,m/z): [M+H]⁺=482.

¹H NMR (400 MHz, D6-DMSO) δ=8.39 (S, 2H), 7.84 (S, 1H), 7.73 (dd, J=6.8 Hz, 2.7 Hz, 1H), 7.49-7.45 (m, 2H), 7.34-7.32 (m, 1H), 7.21-7.16 (m, 2H), 4.00-3.89 (m, 1H), 3.43-3.06 (m, 5H), 2.66 (d, J=15.8 Hz, 1H), 2.20 (s, 3H), 1.90-1.67 (m, 2H), 1.52-1.15 (m, 2H).

Example 7

(S)-3-(1-amino-1,3-dihydrospiro[indene-2,4'-piperidin]-1'-yl)-6-(2,3-dichlorophenyl)-5-methylpyrazine-2-carbonitrile (compound 7)

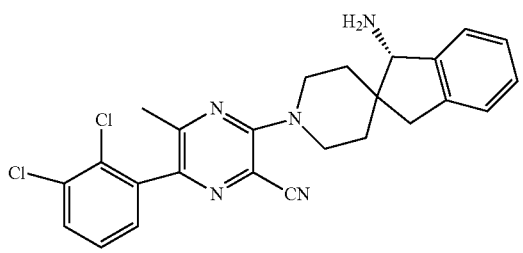 [SMILES: Cc1nc(N2CCC3(CC2)Cc2ccccc2[C@H]3N)c(C#N)nc1-c1cccc(Cl)c1Cl]

Step 1: 3-chloro-6-(2,3-dichlorophenyl)-5-methylpyrazine-2-carbonitrile

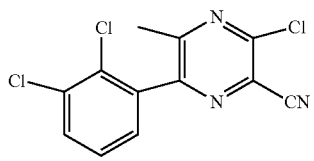 [SMILES: Cc1nc(Cl)c(C#N)nc1-c1cccc(Cl)c1Cl]

At 0° C., under N₂ protection, 3-chloro-6-(2,3-dichlorophenyl)-5-methylpyrazine-2-carboxamide (100 mg) and pyridine (0.11 mL) were added into phosphorus oxychloride (1 mL) The solution was raised to 130° C., and reacted for 10 minutes. After removal of solvent, the obtained product (100 mg) was directly used in the next step.

LC-MS, (ES,m/z): [M+H]⁺=297.

Step 2: (R)—N—((S)-1'-(3-cyano-5-(2,3-dichlorophenyl)-6-methylpyrazin-2-yl)-1,3-dihydrospiro[indene-2,4'-piperidin]-1-yl)-2-methylpropane-2-sulfinamide

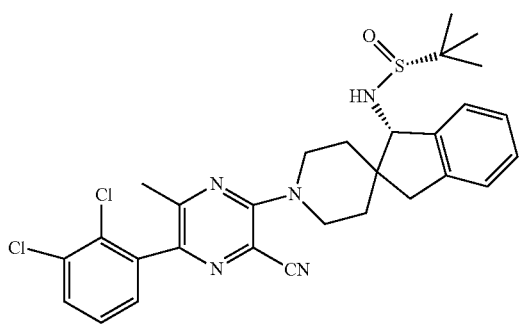 [SMILES: Cc1nc(N2CCC3(CC2)Cc2ccccc2[C@H]3N[S@](=O)C(C)(C)C)c(C#N)nc1-c1cccc(Cl)c1Cl]

The method was similar to the step 9 of example 1. The product (3 ling) was obtained from the starting materials 3-chloro-6-(2,3-dichlorophenyl)-5-methylpyrazine-2-carbonitrile (100 mg) and (R)—N—((S)-1,3-dihydrospiro[indene-2,4'-piperidin]-1-yl)-2-methylpropane-2-sulfinamide trifluoroacetate (103 mg).

LC-MS, (ES,m/z): [M+H]⁺=568.

Step 3: (S)-3-(1-amino-1,3-dihydrospiro[indene-2,4'-piperidin]-1'-yl)-6-(2,3-dichlorophenyl)-5-methylpyrazine-2-carbonitrile

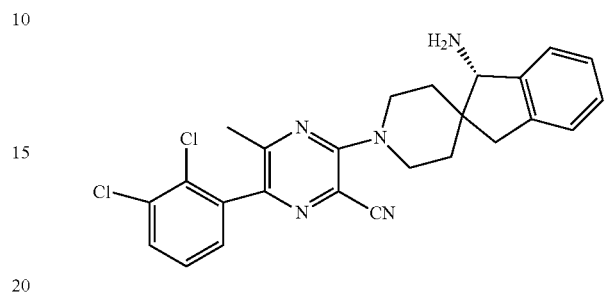

The method was similar to the step 10 of example 1. The product (5 mg) was obtained from the starting material (R)—N—((S)-1'-(3-cyano-5-(2,3-dichlorophenyl)-6-methylpyrazin-2-yl)-1,3-dihydrospiro[indene-2,4'-piperidin]-1-yl)-2-methylpropane-2-sulfinamide (31 mg).

LC-MS, (ES,m/z): [M+H]⁺=463
¹H NMR (400 MHz, D6-DMSO) δ=7.81-7.72 (m, 3H), 7.64 (d, J=7.7 Hz, 1H), 7.56-7.44 (m, 3H), 4.67-4.62 (m, 2H), 4.13-4.10 (m, 1H), 3.29-3.17 (m, 3H), 2.69-2.67 (m, 1H), 2.28 (s, 3H), 2.19-2.12 (m, 2H), 1.77-1.47 (m, 2H).

Example 8

(S)-1-amino-1'-(5-(2,3-dichlorophenyl)-3-(hydroxymethyl)-6-methylpyrazin-2-yl)-1,3-dihydrospiro[indene-2,4'-piperidine]-7-carbonitrile (compound 8)

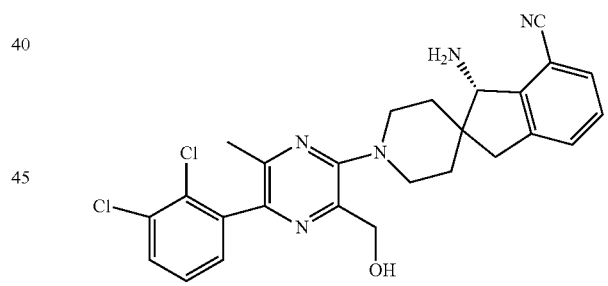

Step 1: 1-tert-butyl 4-ethyl 4-(3-bromobenzyl)piperidine-1,4-dicarboxylate

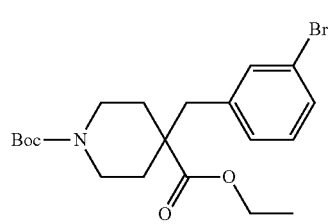 [SMILES: CCOC(=O)C1(Cc2cccc(Br)c2)CCN(C(=O)OC(C)(C)C)CC1]

The method was similar to the step 2 of example 2. The crude product (50.1 g) obtained from the starting material 1-tert-butyl 4-ethyl piperidine-1,4-dicarboxylate (25.7 g) and 1-bromo-3-(bromomethyl)benzene (25.0 g) was used directly in the next step.

LC-MS, (ES, m/z): [M+H]⁺=426.

Step 2: 4-(3-bromobenzyl)-1-(tert-butoxycarbonyl) piperidine-4-carboxylic acid

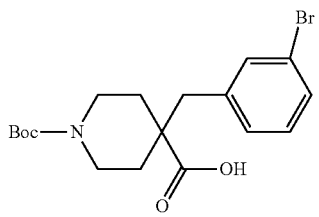 [SMILES: CC(C)(C)OC(=O)N1CCC(Cc2cccc(Br)c2)(C(=O)O)CC1]

The method was similar to the step 3 of example 2. The crude product (30.5 g) was obtained from the starting material 1-tert-butyl 4-ethyl 4-(3-bromobenzyl) piperidine-1,4-dicarboxylate (50.1 g).

LC-MS, (ES, m/z): [M+H]⁺=396.

Step 3: tert-butyl 7-bromo-1-oxo-1,3-dihydrospiro[indene-2,4'-piperidine]-1'-carboxylate

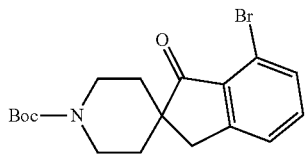

The method was similar to the step 4 of example 2. The product (1.1 g) was obtained from the starting material 4-(3-bromobenzyl)-1-(tert-butoxycarbonyl) piperidine-4-carboxylic acid (30 g).

LC-MS, (ES, m/z): [M+H]⁺=380.

Step 4: tert-butyl 7-cyano-1-oxo-1,3-dihydrospiro[indene-2,4'-piperidine]-1'-carboxylate

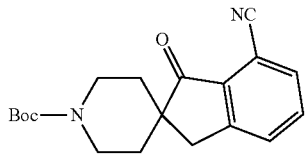 [SMILES: CC(C)(C)OC(=O)N1CCC2(CC1)Cc1cccc(Br)c1C2=O]

The method was similar to the step 5 of example 2. The product (501 mg) was obtained from the starting material tert-butyl 7-bromo-1-oxo-1,3-dihydrospiro[indene-2,4'-piperidine]-1'-carboxylate (1.0 g).

LC-MS, (ES, m/z): [M+H]⁺=327.

Step 5: (R)-tert-butyl 1-(1,1-dimethylethylsulfinamido)-7-cyano-1,3-dihydrospiro[indene-2,4'-piperidine]-1'-carboxylate

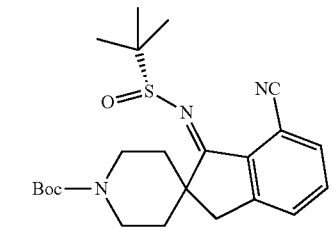 [SMILES: CC(C)(C)OC(=O)N1CCC2(CC1)Cc1cccc(C#N)c1/C2=N/[S@](=O)C(C)(C)C]

The method was similar to the step 6 of example 1. The crude product (701 mg) was obtained from the starting material tert-butyl 7-cyano-1-oxo-1,3-dihydrospiro[indene-2,4'-piperidine]-1'-carboxylate (500 mg).

LC-MS, (ES, m/z): [M+H]⁺=430.

Step 6

(R)—N—((S)-4-cyano-1'-tert-butoxycarbonyl-1,3-dihydrospiro[indene-2,4'-piperidin]-3-yl)-2-methylpropane-2-sulfinamide

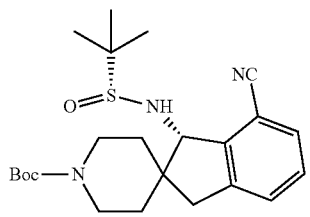 [SMILES: CC(C)(C)OC(=O)N1CCC2(CC1)Cc1cccc(C#N)c1[C@H]2N[S@](=O)C(C)(C)C]

The method was similar to the step 7 of example 1. The product (520 mg) was obtained from the starting material (R)-tert-butyl 1-(1,1-dimethylethylsulfinamido)-7-cyano-1,3-dihydrospiro[indene-2,4'-piperidine]-1'-carboxylate.

LC-MS, (ES, m/z): [M+H]⁺=432.

Step 7: (R)—N—((S)-4-cyano-1,3-dihydrospiro[indene-2,4'-piperidin]-3-yl)-2-methylpropane-2-sulfinamide trifluoroacetate

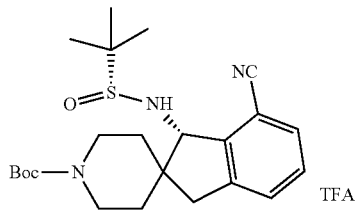 [SMILES: CC(C)(C)OC(=O)N1CCC2(CC1)Cc1cccc(C#N)c1[C@H]2N[S@](=O)C(C)(C)C]

The method was similar to the step 8 of example 1. The crude product (107 mg) was obtained from the starting material (R)—N—((S)-4-cyano-1'-tert-butoxycarbonyl-1,3-dihydrospiro[indene-2,4'-piperidin]-3-yl)-2-methylpropane-2-sulfinamide (140 mg).

LC-MS, (ES, m/z): [M+H]⁺=332.

Step 8: ethyl 3-((S)-7-cyano-1-((R)-1,1-dimethyl-ethylsulfinamido)-1,3-dihydrospiro[indene-2,4'-piperidin]-1'-yl)-6-(2,3-dichlorophenyl)-5-methylpyrazine-2-carboxylate

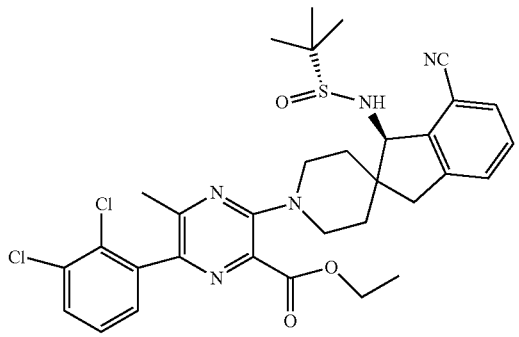 [SMILES: CCOC(=O)c1nc(-c2cccc(Cl)c2Cl)c(C)nc1N1CCC2(CC1)Cc1cccc(C#N)c1[C@@H]2N[S@](=O)C(C)(C)C]

The method was similar to the step 9 of example 1. The product (101 mg) was obtained from the starting materials ethyl 3-chloro-6-(2,3-dichlorophenyl)-5-methyl-pyrazine-2-carboxylate (100 mg) and (R)—N—((S)-4-cyano-1,3-dihydrospiro[indene-2,4'-piperidin]-3-yl)-2-methylpropane-2-sulfinamide trifluoroacetate (107 mg).

LC-MS, (ES, m/z): [M+H]$^+$=640.

Step 9: (S)-ethyl 3-(1-amino-7-cyano-1,3-dihydrospiro[indene-2,4'-piperidin]-1'-yl)-6-(2,3-dichlorophenyl)-5-methylpyrazine-2-carboxylate

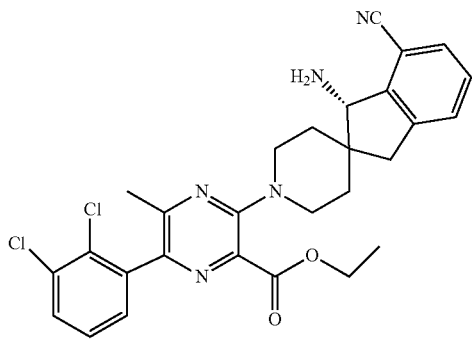 [SMILES: CCOC(=O)c1nc(-c2cccc(Cl)c2Cl)c(C)nc1N1CCC2(CC1)Cc1cccc(C#N)c1[C@H]2N]

The method was similar to the step 10 of example 1. The product (61 mg) was obtained from the starting material ethyl 3-((S)-7-cyano-1-((R)-1,1-dimethylethylsulfinamido)-1,3-dihydrospiro[indene-2,4'-piperidin]-1'-yl)-6-(2,3-dichlorophenyl)-5-methylpyrazine-2-carboxylate.

LC-MS, (ES, m/z): [M+H]$^+$=536.

Step 10: (S)-1-amino-1'-(5-(2,3-dichlorophenyl)-3-(hydroxymethyl)-6-methylpyrazin-2-yl)-1,3-dihydrospiro[indene-2,4'-piperidine]-7-carbonitrile

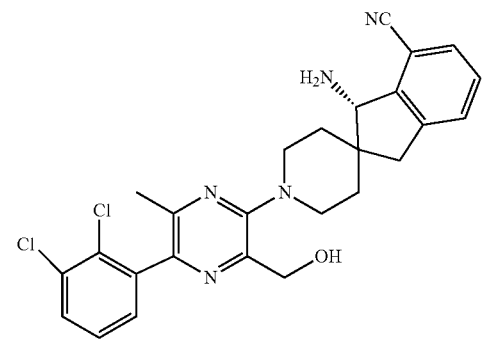 [SMILES: Cc1nc(N2CCC3(CC2)Cc2cccc(C#N)c2[C@H]3N)c(CO)nc1-c1cccc(Cl)c1Cl]

The method was similar to the step 10 of example 2. The product (6 mg) was obtained from the starting material (S)-ethyl 3-(1-amino-7-cyano-1,3-dihydrospiro[indene-2,4'-piperidin]-1'-yl)-6-(2,3-dichlorophenyl)-5-methylpyrazine-2-carboxylate (25 mg).

LC-MS, (ES, m/z): [M+H]$^+$=494.

1H NMR (400 MHz, D6-DMSO) δ=7.74 (dd, J=7.9 Hz, 1.7 Hz, 1H), 7.64-7.54 (m, 2H), 7.51-7.36 (m, 3H), 5.34-5.28 (m, 1H), 4.54-4.50 (m, 2H), 4.1-3.53 (m, 2H), 3.27-2.78 (m, 4H), 2.20 (s, 3H), 2.03-1.92 (m, 2H), 1.74-1.30 (m, 2H).

Example 9 (S)—N-(1-amino-1'-(5-(2,3-dichlorophenyl)-3-(hydroxymethyl)-6-methylpyrazin-2-yl)-1,3-dihydrospiro[indene-2,4'-piperidin]-5-yl)methanesulfonamide (compound 9)

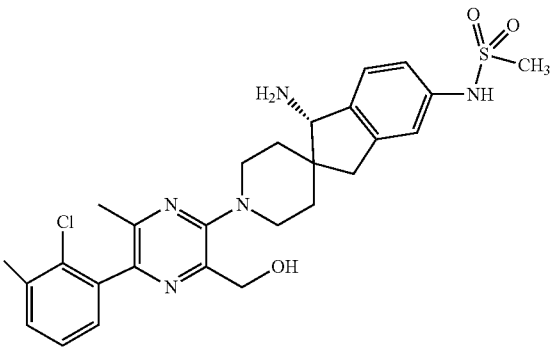

Step 1: tert-butyl 5-bromo-1-oxo-1,3-dihydrospiro[indene-2,4'-piperidine]-1'-carboxylate

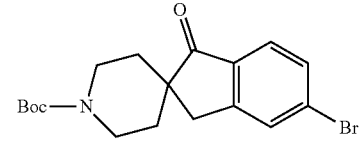 [SMILES: CC(C)(C)OC(=O)N1CCC2(CC1)Cc1cc(Br)ccc1C2=O]

The method was similar to the step 4 of example 2. The product (6.1 g) was obtained from the starting material 4-(3-bromobenzyl)-1-(tert-butoxycarbonyl) piperidine-4-carboxylic acid (30 g).

LC-MS, (ES, m/z): [M+H]⁺=380.

Step 2: tert-butyl 5-(methylsulfonamido)-1-oxo-1,3-dihydrospiro[indene-2,4'-piperidine]-1'-carboxylate

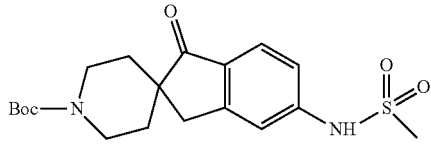 [SMILES: CC(C)(C)OC(=O)N1CCC2(CC1)Cc1cc(NS(C)(=O)=O)ccc1C2=O]

The method was similar to the step 1 of example 3. The crude product (2.5 g) was obtained from the starting material tert-butyl 5-bromo-1-oxo-1,3-dihydrospiro[indene-2,4'-piperidine]-1'-carboxylate (2.0 g).

LC-MS, (ES, m/z): [M+H]⁺=395.

Step 3: (R)-tert-butyl 1-((tert-butylsulfinyl)imino)-5-(methylsulfonamido)-1,3-dihydrospiro[indene-2,4'-piperidine]-1'-carboxylate

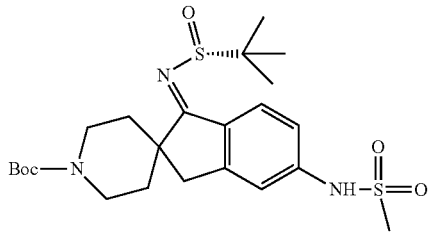 [SMILES: CC(C)(C)OC(=O)N1CCC2(CC1)Cc1cc(NS(C)(=O)=O)ccc1/C2=N\[S@](=O)C(C)(C)C]

The method was similar to the step 6 of example 1. The crude product (3.0 g) was obtained from the starting material tert-butyl 5-(methylsulfonamido)-1-oxo-1,3-dihydrospiro[indene-2,4'-piperidine]-1'-carboxylate (2.5 g).

LC-MS, (ES,m/z): [M+H]⁺=498.

Step 4: (S)-tert-butyl 1-((R)-1,1-dimethylethylsulfinamido)-5-(methylsulfonamido)-1,3-dihydrospiro[indene-2,4'-piperidine]-1'-carboxylate

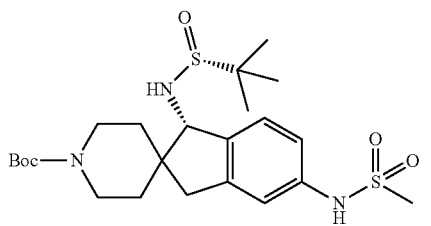 [SMILES: CC(C)(C)OC(=O)N1CCC2(CC1)Cc1cc(NS(C)(=O)=O)ccc1[C@H]2N[S@](=O)C(C)(C)C]

The method was similar to the step 7 of example 1. The product (1.1 g) was obtained from the starting material (R)-tert-butyl 1-((tert-butylsulfinyl)imino)-5-(methylsulfonamido)-1,3-dihydrospiro[indene-2,4'-piperidine]-1'-carboxylate (3.0 g).

LC-MS, (ES, m/z): [M+H]⁺=500.

Step 5: N—((S)-1-((R)-1,1-dimethylethylsulfinamido)-1,3-dihydrospiro[indene-2,4'-piperidin]-5-yl)methanesulfonamide trifluoroacetate

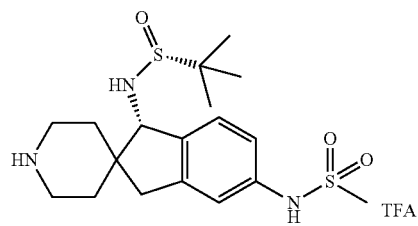 [SMILES: CC(C)(C)[S@@](=O)N[C@@H]1c2ccc(NS(C)(=O)=O)cc2CC12CCNCC2]

The method was similar to the step 8 of example 1. The crude product (140 mg) was obtained from the starting material (S)-tert-butyl 1-((R)-1,1-dimethylethylsulfinamido)-5-(methylsulfonamido)-1,3-dihydrospiro[indene-2,4'-piperidine]-1'-carboxylate (17 Sing).

LC-MS, (ES, m/z): [M+H]⁺=400.

Step 6: ethyl 6-(2,3-dichlorophenyl)-3-((S)-1-((R)-1,1-dimethyl ethylsulfinamido)-5-(methylsulfonamido)-1,3-dihydrospiro[indene-2,4'-piperidin]-1'-yl)-5-methylpyrazine-2-carboxylate

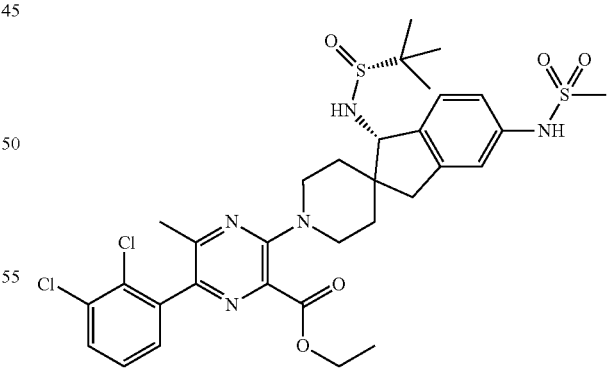

The method was similar to the step 9 of example 1. The product (31 mg) was obtained from the starting materials ethyl 3-chloro-6-(2,3-dichlorophenyl)-5-methylpyrazine-2-carboxylate (100 mg) and N—((S)-1-((R)-1,1-dimethylethylsulfinamido)-1,3-dihydrospiro[indene-2,4'-piperidin]-5-yl)methanesulfonamide trifluoroacetate (140 mg).

LC-MS, (ES, m/z): [M+H]⁺=708.

Step 7: (S)-ethyl 3-(1-amino-5-(methylsulfona-mido)-1,3-dihydrospiro[indene-2,4'-piperidin]-1'-yl)-6-(2,3-dichlorophenyl)-5-methylpyrazine-2-carboxylate

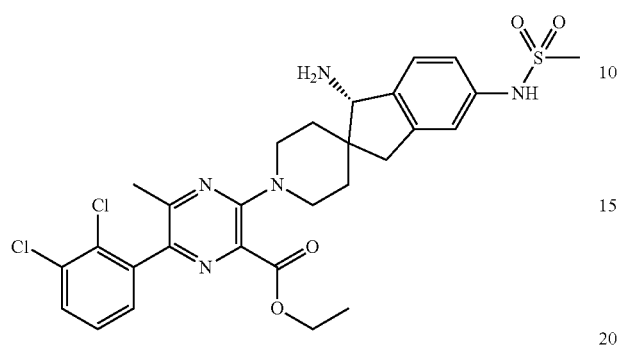

The method was similar to the step 10 of example 1. The product (61 mg) was obtained from the starting material ethyl 6-(2,3-dichlorophenyl)-3-((S)-1-((R)-1,1-dimethylethylsulfinamido)-7-(methylsulfonamido)-1,3-dihydrospiro[indene-2,4'-piperidin]-1'-yl)-5-methylpyrazine-2-carboxylate (80 mg).

LC-MS, (ES, m/z): [M+H]$^+$=603.

Step 8: (S)—N-(1-amino-1'-(5-(2,3-dichlorophenyl)-3-(hydroxyl methyl)-6-methylpyrazin-2-yl)-1,3-dihydrospiro[indene-2,4'-piperidin]-5-yl)methanesulfonamide

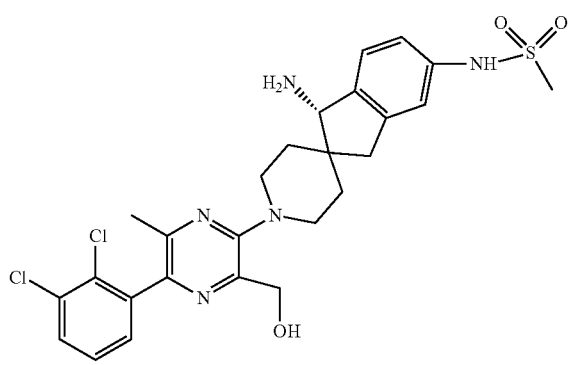 [SMILES: Cc1nc(N2CCC3(CC2)Cc2cc(NS(C)(=O)=O)ccc2[C@H]3N)c(CO)nc1-c1cccc(Cl)c1Cl]

The method was similar to the step 10 of example 2. The product (11 mg) was obtained from the starting material (S)-ethyl 3-(1-amino-5-(methylsulfonamido)-1,3-dihydrospiro[indene-2,4'-piperidin]-1'-yl)-6-(2,3-dichlorophenyl)-5-methylpyrazine-2-carboxylate (57 mg).

LC-MS, (ES, m/z): [M+H]$^+$=562.

$^1$H NMR (400 MHz, D6-DMSO) δ=9.62 (s, 1H), 7.74 (dd, J=7.8 Hz, 1.7 Hz, 1H), 7.51-7.42 (m, 2H), 7.27 (d, J=7.8 Hz, 1H), 7.06-7.04 (m, 2H), 4.64-4.51 (m, 3H), 3.69-3.65 (m, 2H), 3.36-3.12 (m, 3H), 3.02-2.63 (m, 5H), 2.20 (s, 3H), 1.98-1.75 (m, 2H), 1.58-1.33 (m, 2H).

Example 10

(S)-(3-(1-amino-1,3-dihydrospiro[indene-2,4'-piperidin]-1'-yl)-6-(2-amino-3-chloropyridin-4-yl)-5-methylpyrazin-2-yl)methanol (compound 10)

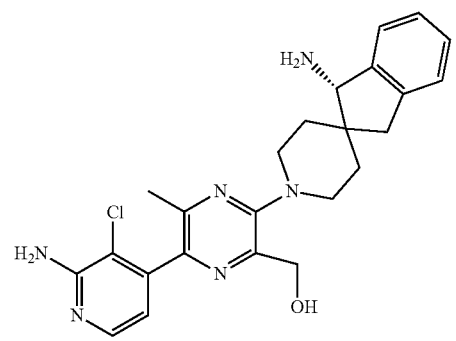 [SMILES: Cc1nc(N2CCC3(CC2)Cc2ccccc2[C@H]3N)c(CO)nc1-c1ccnc(N)c1Cl]

Step 1: 3-chloro-4-iodo-N,N-ditertbutoxycarbonyl-pyridine-2-amine

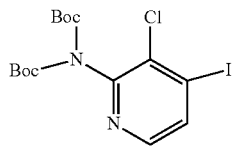

3-chloro-4-iodopyridin-2-amine (15.0 g), di-tert-butyl dicarbonate (51.5 g) and triethylamine (23.8 g) were added into tetrahydrofuran (500 mL). The reaction solution was refluxed overnight. After pouring the reaction solution to the water (500 mL), the solution was extracted by dichloromethane (400 mL) for 3 times and dried by anhydrous sodium sulfate. The product (21.2 g) was obtained after removal of solvent and purification with column chromatography (petroleum ether/ethyl acetate=5/1).

LC-MS, (ES, m/z): [M+H]$^+$=455.

Step 2: 2-(N,N-(ditertbutoxycarbonyl)amino)-3-chloropyridin-4-pinacolato boron

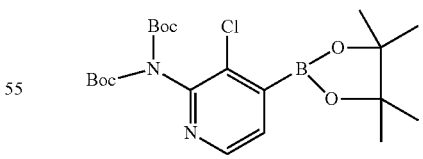

3-chloro-4-iodo-N,N-ditertbutoxycarbonyl-pyridine-2-amine (9.0 g), bis(pinacolato)diboron (6.0 g), Pd(dppf)Cl$_2$ (103 mg) and anhydrous potassium acetate (3.9 g) were added into N,N-dimethyl acetamide (60 mL). The mixture was reacted under 100° C. for 3 hours under N$_2$ protection. Then, the mixture was poured into water (200 mL), extracted by ethyl acetate (50 mL) for 3 times, the obtained organic phase was dried by anhydrous sodium sulfate. After removal of solvent and purification with column chromatography (dichloromethane/methanol=50/1), the product (2.2 g) was obtained.

LC-MS, (ES,m/z): [M+H]$^+$=372.

Step 3: ethyl 6-(2-(N,N-di(tert-butoxycarbonyl)amino)-3-chloropyridin-4-yl)-3-chloro-5-methylpyrazine-2-carboxylate

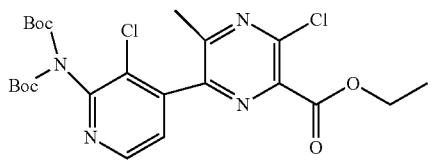 [SMILES: CCOC(=O)c1nc(-c2ccnc(N(C(=O)OC(C)(C)C)C(=O)OC(C)(C)C)c2Cl)c(C)nc1Cl]

2-(N,N-(ditertbutoxycarbonyl)amino)-3-chloropyridin-4-pinacolato boron (2.0 g), ethyl 6-bromo-3-chloro-5-methylpyrazine-2-carboxylate (1.4 g), Pd(dppf)Cl$_2$ (525 mg) and potassium carbonate (1.9 g) were added into acetonitrile (100 mL). Under N$_2$ protection, the mixture was raised to 90° C. and reacted overnight. Then, the mixture was poured into water (200 mL), and extracted by dichloromethane (100 mL) for 3 times, and the obtained organic phase was dried by anhydrous sodium sulfate. After removal of solvent and purification with column chromatography (dichloromethane/methanol=50/1), the product (970 mg) was obtained.

LC-MS, (ES,m/z): [M+H]$^+$=527.

Step 4: ethyl 6-(2-(N,N-di(tert-butoxycarbonyl)amino)-3-chloropyridin-4-yl)-3-((S)-1-(R)-1,1-dimethylethylsulfinamido)-1,3-dihydrospiro[indene-2,4'-piperidin]-1'-yl)-5-methylpyrazine-2-carboxylate

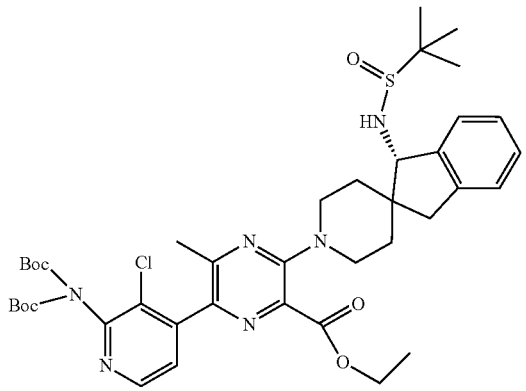 [SMILES: CCOC(=O)c1nc(-c2ccnc(N(C(=O)OC(C)(C)C)C(=O)OC(C)(C)C)c2Cl)c(C)nc1N1CCC2(CC1)Cc1ccccc1[C@H]2NS(=O)C(C)(C)C]

The method was similar the step 9 of example 1. The product (150 mg) was obtained from the starting materials ethyl 6-(2-(N,N-di(tert-butoxycarbonyl) amino)-3-chloropyridin-4-yl)-3-chloro-5-methylpyrazine-2-carboxylate (200 mg) and (R)—N—((S)-1,3-dihydrospiro[indene-2,4'-piperidin]-1'-yl)-2-methylpropane-2-sulfinamide trifluoroacetate (177 mg).

LC-MS, (ES,m/z): [M+H]$^+$=797.

Step 5: (S)-ethyl 3-(1-amino-1,3-dihydrospiro[indene-2,4'-piperidin]-1'-yl)-6-(2-amino-3-chloropyridin-4-yl)-5-methylpyrazine-2-carboxylate

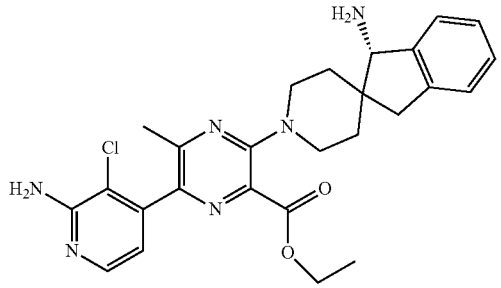 [SMILES: CCOC(=O)c1nc(-c2ccnc(N)c2Cl)c(C)nc1N1CCC2(CC1)Cc1ccccc1[C@H]2N]

The method was similar to the step 10 of example 1. The product (50 mg) was obtained from the starting material the ethyl 6-(2-(N,N-di(tert-butoxycarbonyl)amino)-3-chloropyridin-4-yl)-3-((S)-1-(R)-1,1-dimethylethylsulfinamido)-1,3-dihydrospiro[indene-2,4'-piperidin]-1'-yl)-5-methylpyrazine-2-carboxylate (150 mg).

LC-MS, (ES, m/z): [M+H]$^+$=493

Step 6: (S)-(3-(1-amino-1,3-dihydrospiro[indene-2,4'-piperidin]-1'-yl)-6-(2-amino-3-chloropyridin-4-yl)-5-methylpyrazin-2-yl)methanol

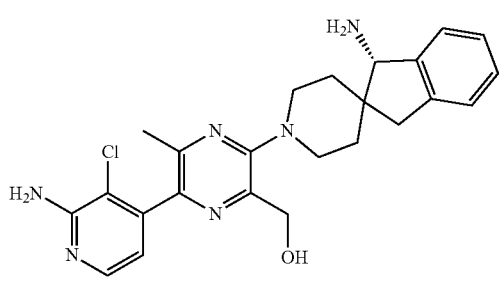 [SMILES: Cc1nc(N2CCC3(CC2)Cc2ccccc2[C@H]3N)c(CO)nc1-c1ccnc(N)c1Cl]

The method was similar to the step 10 of example 2. The product (6 mg) was obtained from the starting material (S)-ethyl 3-(1-amino-1,3-dihydrospiro[indene-2,4'-piperidin]-1'-yl)-6-(2-amino-3-chloropyridin-4-yl)-5-methylpyrazine-2-carboxylate (50 mg).

LC-MS, (ES, m/z): [M+H]$^+$=451.

Example 11

(S)-(3-(1-amino-1,3-dihydrospiro[indene-2,4'-piperidin]-1'-yl)-6-(2,3-dichlorophenyl)pyrazin-2-yl)methanol (compound 11)

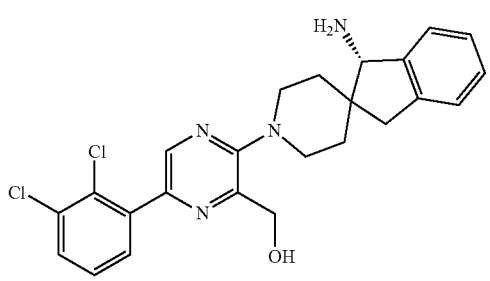 [SMILES: N[C@@H]1c2ccccc2CC12CCN(c1ncc(-c3cccc(Cl)c3Cl)nc1CO)CC2]

Step 1: 3-chloro-6-(2,3-dichlorophenyl)pyrazine-2-carboxylic acid

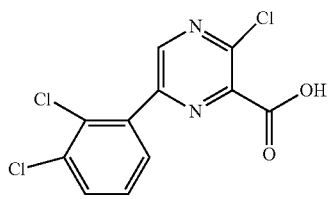 [SMILES: O=C(O)c1nc(-c2cccc(Cl)c2Cl)cnc1Cl]

At room temperature, ethyl 6-bromo-3-chloropyrazine-2-carboxylate (1.0 g), 2,3-dichlorophenylboronic acid (760 g), PddppfCl$_2$ (290 mg) and sodium carbonate (1.3 g) were added into a mixture of 1,4-dioxane (20 mL) and water (5 mL) Under N$_2$ protection, the solution was raised to 100° C. and reacted for 4 hours. The solution was poured into water (200 mL) and extracted by ethyl acetate (100 mL) for 3 times. The organic phase was washed by saturated brine and dried by anhydrous sodium sulfate. The crude product was obtained after removal of solvent. And the product (0.7 g) was obtained through column chromatography.

LC-MS, (ES, m/z): [M+H]$^+$=303.

Step 2: methyl 3-chloro-6-(2,3-dichlorophenyl)pyrazine-2-carboxylate

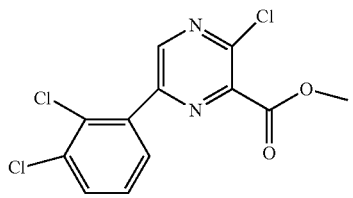 [SMILES: COC(=O)c1nc(-c2cccc(Cl)c2Cl)cnc1Cl]

At room temperature, 3-chloro-6-(2,3-dichlorophenyl)pyrazine-2-carboxylic acid (0.7 g) and potassium carbonate (0.5 g) were added into N,N-dimethylformamide (7 mL). Iodomethane (0.8 mL) was added dropwisely into the solution. The solution was kept being reacted at room temperature for 2 hours. Then the solution was poured into water (200 mL), and extracted by ethyl acetate (20 mL) for 3 times. The organic phase was washed by saturated brine and dried by anhydrous sodium sulfate. The product (550 mg) was obtained after removal of solvent.

LC-MS, (ES, m/z): [M+H]$^+$=339.

Step 3: methyl 6-(2,3-dichlorophenyl)-3-((S)-1-(R)-1,1-dimethylethylsulfinamido)-1,3-dihydrospiro[indene-2,4'-piperidin]-1'-yl)pyrazine-2-carboxylate

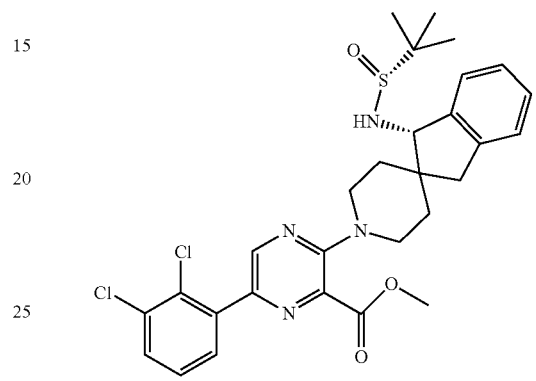

The method was similar to step 9 of example 1. The product (252 mg) was obtained from the starting materials methyl 3-chloro-6-(2,3-dichlorophenyl)pyrazine-2-carboxylate (141 mg) and (R)—N—((S)-1,3-dihydrospiro[indene-2,4'-piperidin]-1'-yl)-2-methylpropane-2-sulfinamide trifluoroacetate (206 mg).

LC-MS, (ES, m/z): [M+H]$^+$=587.

Step 4: (S)-methyl 3-(1-amino-1,3-dihydrospiro[indene-2,4'-piperidin]-1'-yl)-6-(2,3-dichlorophenyl)pyrazine-2-carboxylate

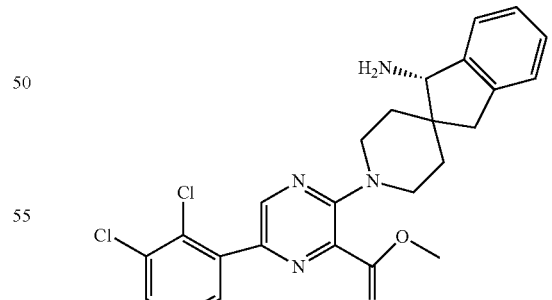

The method was similar to step 10 of example 1. The product (139 mg) was obtained from the starting material methyl 6-(2,3-dichlorophenyl)-3-((S)-1-(R)-1,1-dimethylethylsulfinamido)-1,3-dihydrospiro[indene-2,4'-piperidin]-1'-yl)pyrazine-2-carboxylate (202 mg).

LC-MS, (ES, m/z): [M+H]$^+$=483.

Step 5: (S)-(3-(1-amino-1,3-dihydrospiro[indene-2,4'-piperidin]-1'-yl)-6-(2,3-dichlorophenyl)pyrazin-2-yl)methanol

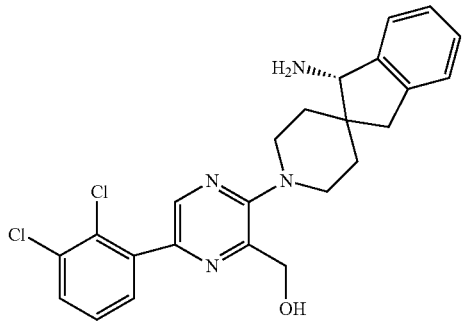 [SMILES: N[C@@H]1c2ccccc2CC12CCN(c1ncc(-c3cccc(Cl)c3Cl)nc1CO)CC2]

The method was similar to the step 10 of example 2. The product (8 mg) was obtained from the starting material (S)-methyl 3-(1-amino-1,3-dihydrospiro[indene-2,4'-piperidin]-1'-yl)-6-(2,3-dichlorophenyl) pyrazine-2-carboxylate (23 mg).

LC-MS, (ES, m/z): [M+H]$^+$=455.

1H NMR (400 MHz, CDCl$_3$) δ=8.49 (s, 1H), 7.57-7.49 (m, 2H), 7.40-7.32 (m, 3H), 7.28-7.23 (m, 2H), 4.79 (d, J=5.7 Hz, 2H), 4.06 (s, 1H), 3.66-3.56 (m, 3H), 3.26-3.11 (m, 3H), 2.77 (d, J=15.8 Hz, 1H), 2.05-1.88 (m, 1H), 1.70-1.45 (m, 2H).

Example 12

(S)-(3-(1-amino-1,3-dihydrospiro[indene-2,4'-piperidin]-1'-yl)-5-methyl-6-(2-(trifluoromethyl)pyridin-3-yl)pyrazin-2-yl)methanol (compound 12)

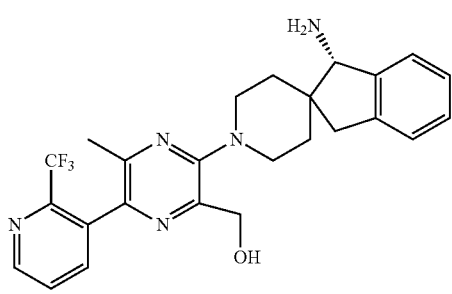 [SMILES: Cc1nc(N2CCC3(CC2)Cc2ccccc2[C@H]3N)c(CO)nc1-c1cccnc1C(F)(F)F]

Step 1: 3-(4,4,5,5-tetramethyl-1,3,2-dioxaborolan-2-yl)-2-(trifluoromethyl)pyridine

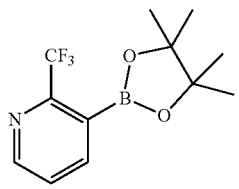 [SMILES: CC1(C)OB(c2cccnc2C(F)(F)F)OC1(C)C]

3-bromo-2-(trifluoromethyl) pyridine (500 mg), bis(pinacolato) diboron (562 mg), Pd(dppf)Cl$_2$ (113 mg) and potassium acetate (433 mg) were added into 1,4-dioxane (5 mL). Under N$_2$ protection, the solution was raised to 105° C. and reacted for 2 hours. The solution was cooled to the room temperature, poured into water (10 mL), extracted by dichloromethane (20 mL) for 3 times and dried by anhydrous sodium sulfate. The product (401 mg) was obtained after removal of solvent and purification with column chromatography (petroleum ether/ethyl acetate=3/1).

LC-MS, (ES, m/z): [M+H]$^+$=274.

Step 2: ethyl 3-chloro-5-methyl-6-(2-(trifluoromethyl)pyridin-3-yl)pyrazine-2-carboxylate

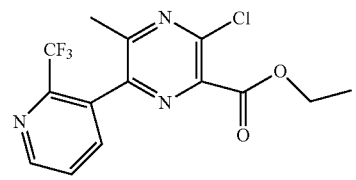 [SMILES: CCOC(=O)c1nc(-c2cccnc2C(F)(F)F)c(C)nc1Cl]

3-(4,4,5,5-tetramethyl-1,3,2-dioxaborolan-2-yl)-2-(trifluoromethyl) pyridine (400 mg), ethyl 6-bromo-3-chloro-5-methylpyrazine-2-carboxylate (400 mg), Pd(dppf)Cl$_2$ (240 mg) and potassium carbonate (800 mg) were added into acetonitrile (4 mL) Under N$_2$ protection, the solution was refluxed overnight. Then, the solution was cooled to the room temperature, poured into water (20 mL), and extracted by dichloromethane (100 mL) for three times. The organic phase was dried by anhydrous sodium sulfate. After removal of solvent and purification with column chromatography (petroleum ether/ethyl acetate)=5/1, the product was obtained (149 mg).

LC-MS, (ES,m/z): [M+H]$^+$=346.

Step 3: ethyl 3-((S)-1-(R)-1,1-dimethylethylsulfinamido)-1,3-dihydrospiro[indene-2,4'-piperidin]-1'-yl)-5-methyl-6-(2-(trifluoromethyl) pyridin-3-yl)pyrazine-2-carboxylate

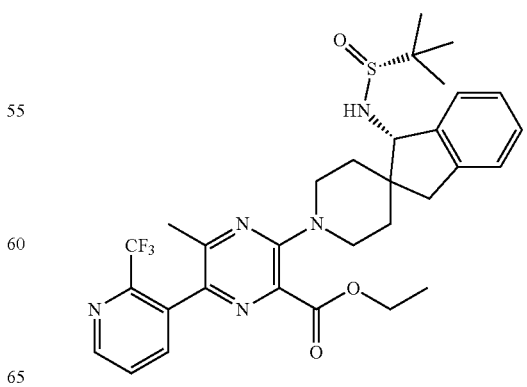

The method was similar to the step 9 of example 1. The product (60 mg) was obtained from the starting materials ethyl 3-chloro-5-methyl-6-(2-(trifluoromethyl)pyridin-3-yl)pyrazine-2-carboxylate (149 mg) and (R)—N—((S)-1,3-dihydrospiro[indene-2,4'-piperidin]-1-yl)-2-methylpropane-2-sulfinamide trifluoroacetate (180 mg).

LC-MS, (ES,m/z): [M+H]⁺=616.

Step 4: (S)-ethyl 3-(1-amino-1,3-dihydrospiro[indene-2,4'-piperidin]-1'-yl)-5-methyl-6-(2-(trifluoromethyl)pyridin-3-yl)pyrazine-2-carboxylate

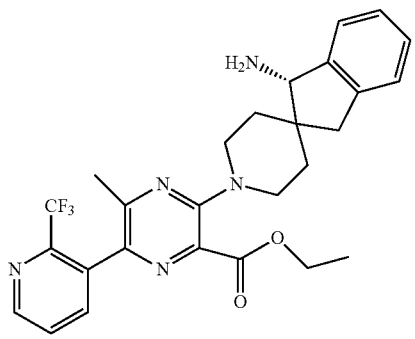 [SMILES: CCOC(=O)c1nc(-c2cccnc2C(F)(F)F)c(C)nc1N1CCC2(CC1)Cc1ccccc1[C@H]2N]

The method was similar to the step 10 of example 1. The product (32 mg) was obtained from the starting material ethyl 3-((S)-1-(R)-1,1-dimethylethylsulfinamido)-1,3-dihydrospiro[indene-2,4'-piperidin]-1'-yl)-5-methyl-6-(2-(trifluoromethyl)pyridin-3-yl)pyrazine-2-carboxylate (60 mg).

LC-MS, (ES, m/z): [M+H]⁺=512.

Step 5: (S)-(3-(1-amino-1,3-dihydrospiro[indene-2,4'-piperidin]-1'-yl)-5-methyl-6-(2-(trifluoromethyl)pyridine-3-yl)pyrazin-2-yl)methanol

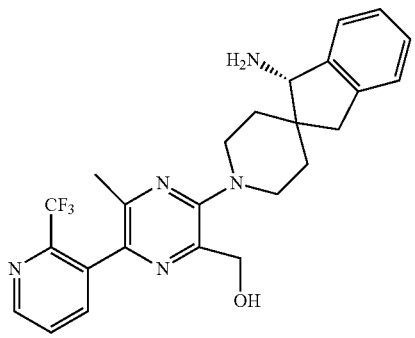 [SMILES: Cc1nc(N2CCC3(CC2)Cc2ccccc2[C@H]3N)c(CO)nc1-c1cccnc1C(F)(F)F]

The method was similar to the step 10 of example 2. The product (4 mg) was obtained from the starting material (S)-ethyl 3-(1-amino-1,3-dihydrospiro[indene-2,4'-piperidin]-1'-yl)-5-methyl-6-(2-(trifluoromethyl) pyridin-3-yl)pyrazine-2-carboxylate (30 mg).

LC-MS, (ES, m/z): [M+H]⁺=470.

¹H NMZ (400 MHz, D6-DMSO) δ=8.86-8.83 (m, 1H), 8.06-8.04 (m, 1H), 7.86-7.83 (m, 1H), 7.71-7.68 (m, 1H), 7.25-7.17 (m, 3H), 5.60-5.45 (m, 2H), 5.24 (t, J=5.8 Hz, 1H), 4.51 (d, J=5.7 Hz, 2H), 3.77-3.70 (m, 3H), 3.15-3.04 (m, 3H), 2.79 (d, J=15.8 Hz, 1H), 2.17 (s, 3H), 2.05-1.96 (m, 2H), 1.57-1.28 (m, 2H).

Example 13

(S)-(3-(5-amino-5,7-dihydrospiro[cyclopenta[b]pyridine-6,4'-piperidin]-1'-yl)-6-(2,3-dichlorophenyl)-5-methylpyrazin-2-yl)methanol (compound 13)

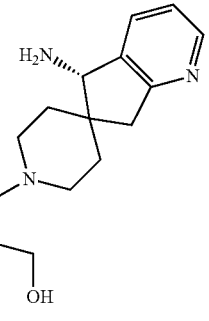

Step 1: tert-butyl 4-((2-chloropyridin-3-yl)(hydroxy)methyl)-4-methylpiperidine-1-carboxylate

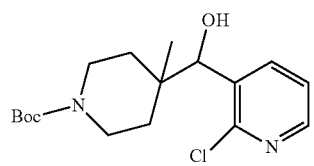 [SMILES: CC(C)(C)OC(=O)N1CCC(C)(C(O)c2cccnc2Cl)CC1]

Under N₂ protection, 2-chloropyridine was dissolved into tetrahydrofuran (10 mL), and cooled to −70° C. LDA (2.8 mL, 2M) was added to the solution and stirred for 2 hours, and tert-butyl 4-formyl-4-methylpiperidine-1-carboxylate (1.0 g) was added to the solution. The solution was kept being stirred at the temperature for 2 hours. As monitored by LC-MS, the reaction was complete. Water (200 mL) was added to the solution to quench reaction. After the solution was extracted by EA (100 mL*3) and dried by spinning, the crude product 1.4 g was obtained.

LC-MS, (ES, m/z): [M+H]⁺=341.

Step 2: tert-butyl 4-(2-chloronicotinoyl)-4-methylpiperidine-1-carboxylate

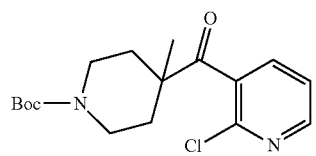 [SMILES: CC(C)(C)OC(=O)N1CCC(C)(C(=O)c2cccnc2Cl)CC1]

Under N₂ protection, tert-butyl 4-((2-chloropyridin-3-yl)(hydroxy)methyl)-4-methylpiperidine-1-carboxylate (1.4 g) was dissolved into dichloromethane (14 mL), and cooled to 0° C. Dess-martin reagent (3.5 g) was added to the solution, and the solution was reacted at room temperature overnight.

The reaction was quenched by saturated sodium thiosulfate solution. After the solution was extracted by EA and organic phase was separated by column chromatography (PE/EA=1:2), yellow oily product (0.9 g) was obtained.

LC-MS, (ES, m/z): [M+H]⁺=338.

Step 3: tert-butyl 5-oxo-5,7-dihydrospiro[cyclopenta[13]pyridine-6,4'-piperidine]-1'-carboxylate

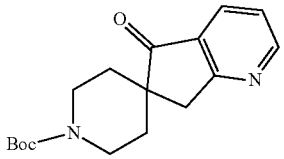 [SMILES: CC(C)(C)OC(=O)N1CCC2(CC1)Cc1ncccc1C2=O]

Under N₂ protection, tert-butyl 4-(2-chloronicotinoyl)-4-methylpiperidine-1-carboxylate (1.0 g), cesium carbonate (1.2 g), trimethylacetic acid (91 mg), palladium acetate (33 mg), Cy₃PHBF₄ (109 mg) and mesitylene (10 mL) were added into a 100 mL three-neck flask, and reacted at 140° C. for 24 hours. After the reaction temperature was lowered, EA was added into the solution. The mixture was filtered and dried by spinning After separation by column chromatography (PE/EA=2:1), yellow solid (53 ling) was obtained.

LC-MS, (ES, m/z): [M+H]⁺=303.

Step 4: (S)-(3-(5-amino-5,7-dihydrospiro[cyclopenta[b]pyridine-6,4'-piperidin]-1'-yl)-6-(2,3-dichlorophenyl)-5-methylpyrazin-2-yl)methanol

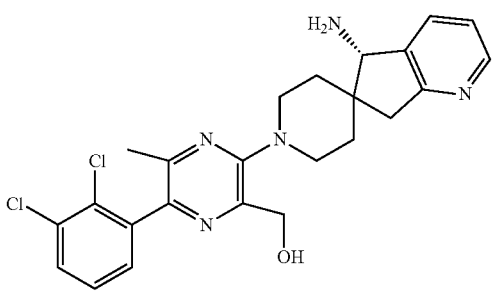 [SMILES: Cc1nc(N2CCC3(CC2)Cc2ncccc2[C@H]3N)c(CO)nc1-c1cccc(Cl)c1Cl]

The method was similar to the steps 6-11 of example 1. The product (26 mg) was obtained.

LC-MS, (ES,m/z): [M+H]⁺=512.

¹H NMR (400 MHz, D6-DMSO) δ 8.40 (d, J=5.4 Hz, 1H), 7.87-7.68 (m, 2H), 7.49 (t, J=7.8 Hz, 1H), 7.44 (dd, J=7.6, 1.7 Hz, 1H), 7.24 (dd, J=7.5, 5.0 Hz, 1H), 5.32 (t, J=4.7 Hz, 1H), 4.54 (d, J=4.5 Hz, 2H), 4.15 (s, 1H), 3.87-3.68 (m, 2H), 3.14 (dd, J=14.3, 8.4 Hz, 3H), 2.87 (d, J=16.4 Hz, 1H), 2.21 (s, 3H), 1.91 (dd, J=20.9, 11.4 Hz, 2H), 1.59 (d, J=13.8 Hz, 1H), 1.36 (d, J=12.4 Hz, 1H).

Example 14

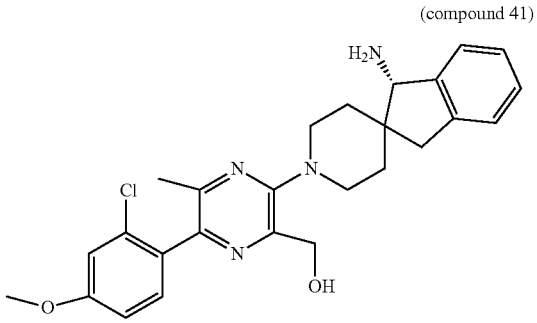 [SMILES: COc1ccc(-c2nc(CO)c(N3CCC4(CC3)Cc3ccccc3[C@H]4N)nc2C)c(Cl)c1]

(compound 41)

The method of compound 41 was similar to the compound 1. The difference was substituting 2,3-dichloroboronic acid with 2-chloro-4-methoxyphenylbronic acid. 2-chloro-4-methoxyphenylbronic acid (CAS: 219735-99-6) was purchased from Shanghai Yuanye Bio-Technology Co., Ltd.

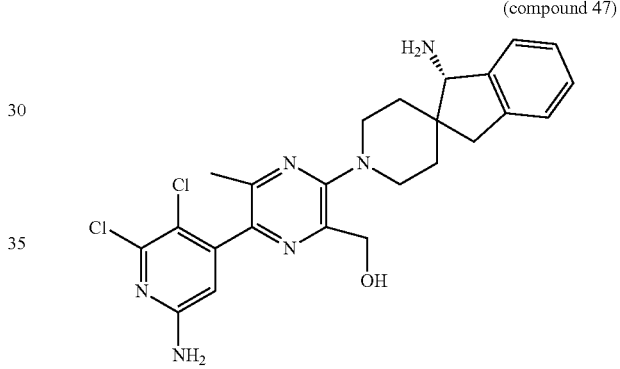

(compound 47)

Example 15

Step 1: tert-butyl (6-chloropyridin-2-yl)carbamate

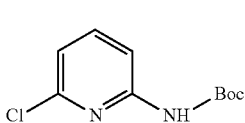 [SMILES: CC(C)(C)OC(=O)Nc1cccc(Cl)n1]

6-chloropyridin-2-amine (10 g) was dissolved into dichloromethane (100 mL). TEA (11.8 g), DMAP (928 mg) and (Boc)₂O (25.4 g) were added to the solution, and stirred overnight. After reaction of the solution was complete monitored through LC-MS, water (500 mL) was poured into the solution, and the solution was extracted by dichloromethane (400 mL*3). The organic phase was washed by saturated sodium chloride, and dried by anhydrous sodium sulfate. Solvent was removed from the organic phase. After beating with PE:EA (10:1) and filtering, the product (8.0 g) was obtained.

LC-MS, (ES,m/z): [M+H]⁺=229.7

Step 2: tert-butyl (5,6-dichloropyridin-2-yl)carbamate

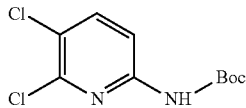 [SMILES: CC(C)(C)OC(=O)Nc1ccc(Cl)c(Cl)n1]

tert-butyl (6-chloropyridin-2-yl) carbamate (8.0 g) was dissolved in DMF (50 mL), and NCS (5.1 g) was added to the solution. The temperature of the solution was raised to 100° C., and the solution was kept reacted for 3 hours. The reaction was complete by LC-MS. The solution was cooled to room temperature, poured to water (500 mL), and extracted by ethyl acetate (400 mL*3). The organic phase was washed by saturated sodium chloride (500 mL), and dried by anhydrous sodium sulfate. The crude product was obtained after removal of solvent. After column chromatography with PE:EA (0-100%), white solid (5.0 g) was obtained.

LC-MS, (ES,m/z): [M+H]$^+$=264.1.

Step 3: ethyl 6-(6-((tert-butoxycarbonyl)amino)-2,3-dichloropyridin-4-yl)-3-chloro-5-methylpyrazine-2-carboxylate

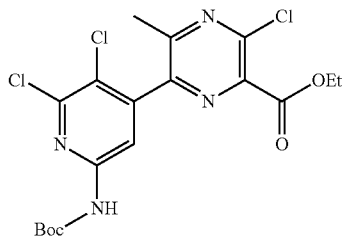 [SMILES: CCOC(=O)c1nc(-c2cc(NC(=O)OC(C)(C)C)nc(Cl)c2Cl)c(C)nc1Cl]

tert-butyl (5,6-dichloropyridin-2-yl)carbamate (2.63 g) was added into a 100 mL single-neck flask, and was dissolved by introducing anhydrous THF (20 mL) Under N$_2$ protection, the solution was cooled to −78° C. LDA (13 mL) was added dropwisely to the solution, and the solution was stirred at that temperature for one hour. ZnCl$_2$ solution in THF (1 mol/L, 13 mL) was added dropwisely and stirred at room temperature for an hour. The solution was a yellow clear liquid. Pd(PPh$_3$)$_4$ (1.15 g) and ethyl 6-bromo-3-chloro-5-methylpyrazine-2-carboxylate (4.10 g) were added to the solution, and the flask was filled with N$_2$. After the temperature was raised to 80° C., the solution was stirred for about 1 hour. The reaction was complete as monitored by LC-MS. The solution was cooled to room temperature, and aqueous NH$_4$Cl (20 mL) was added to the solution. The solution was extracted by ethyl acetate (60 mL*3), washed by saturated salt water (50 mL*1), and dried by anhydrous sodium sulfate. After removal of solvent and separation by column chromatography PE:EA (0-100%), the product was obtained. (1.3 g)

LC-MS, (ES,m/z): [M+H]$^+$=462.7.

The method of compound 47 was similar to that of compound 1. The difference was substituting ethyl 3-chloro-6-(2,3-dichlorophenyl)-5-methylpyrazine-2-carboxylate with ethyl 6-(6-((tert-butoxycarbonyl)amino)-2,3-dichloropyridin-4-yl)-3-chloro-5-methyl pyrazine-2-carboxylate.

Example 16

(compound 49)

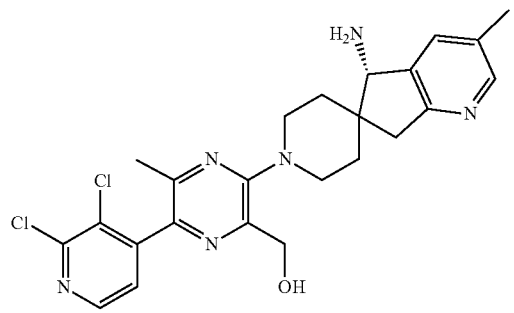

Step 1: (2,3-chloropyridin-4-yl)boronic acid

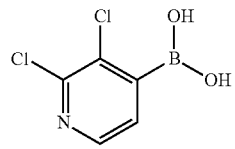 [SMILES: OB(O)c1ccnc(Cl)c1Cl]

At −78° C., n-butyl lithium (29.8 mL, 71.45 mmol) was added slowly into 2,3-dichloropyridine (10 g) solution in THF (100 mL) and reacted for 90 minutes. Triisopropyl borate (15 g) was added to the solution, and reacted at −78° C. for 1 hour. Saturated ammonium chloride was added to the solution to quench the reaction. The solution was adjusted by 1N sodium hydroxide to pH=12, and extracted by ethyl acetate (100 mL). Organic phase was washed by saturated sodium chloride (50 mL*3). After the solution was dried by anhydrous sodium sulfate and spinning, the product was obtained (7 g).

The method of compound 49 was similar to that of compound 47 and compound 13. (2,3-dichloropyridin-4-yl) boronic acid and tert-butyl 5-oxo-3-methyl-5,7-dihydrospiro [cyclopenta[b]pyridine-6,4'-piperidine]-1'-carboxylate were used as starting materials for compound 49.

The preparation of tert-butyl 5-oxo-3-methyl-5,7-dihydrospiro[cyclopenta[b]pyridine-6,4'-piperidine]-1'-carboxylate was similar to the steps of example 13. The difference was that the material of step 1 was replaced by 2-chloro-6-methylpyridine.

Example 17

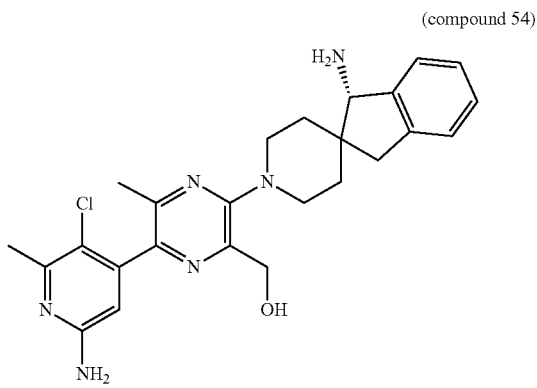 [SMILES: Cc1nc(N2CCC3(CC2)Cc2ccccc2[C@H]3N)c(CO)nc1-c1cc(N)nc(C)c1Cl]
(compound 54)

The intermediate ethyl 6-(6-((tert-butoxycarbonyl)amino)-2,3-dichloropyridin-4-yl)-3-((S)-1-((R)-1,1-dimethylethylsulfinamido)-1,3-dihydrospiro[indene-2,4'-piperidin]-1'-yl)-5-methylpyrazine-2-carboxylate of compound 47 was used.

Step 1: ethyl 6-(6-((tert-butoxycarbonyl)amino)-3-chloro-2-methylpyridin-4-yl)-3-((S)-1-((R)-1,1-dimethylethylsulfinamido-1,3-dihydrospiro[indene-2,4'-piperidin]-1'-yl)-5-methylpyrazine-2-carboxylate

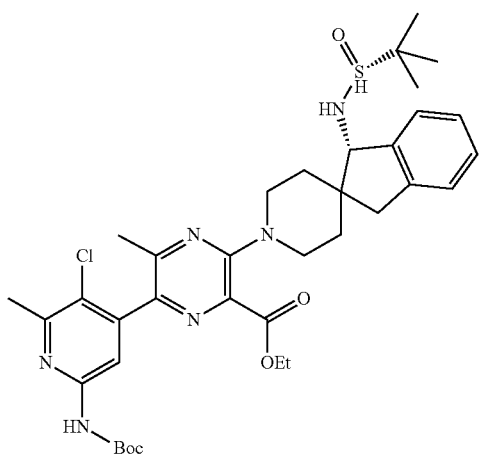 [SMILES: CCOC(=O)c1nc(-c2cc(NC(=O)OC(C)(C)C)nc(C)c2Cl)c(C)nc1N1CCC2(CC1)Cc1ccccc1[C@H]2N[S@](=O)C(C)(C)C]

Ethyl 6-(6-((tert-butoxycarbonyl)amino)-2,3-dichloropyridin-4-yl)-3-((S)-1-((R)-1,1-dimethylethylsulfinamido)-1,3-dihydrospiro[indene-2,4'-piperidin]-1'-yl)-5-methylpyrazine-2-carboxylate (250 mg) was dissolved into 1,4-dioxane (5 mL). Pd(dppf)Cl$_2$ (21.9 mg), K$_2$CO$_3$ (138.0 mg), methyl boric acid (20.4 mg) and water (1 mL) were added into the solution. Under N$_2$ protection, the solution was stirred at 100° C. overnight. The reaction of the solution was complete as monitored by LC-MS. The solution was cooled to room temperature, and poured to water (50 mL) After being extracted with ethyl acetate (40 mL*3), the organic phase was washed by saturated sodium chloride (50 mL), and dried by anhydrous sodium sulfate. After removal of solvent and separation by chromatography PE:EA (1-100%), the product (200 mg) was obtained.

LC-MS, (ES,m/z): [M+H]$^+$=712.7.

The method of compound 54 was similar to that of example 10.

Example 18

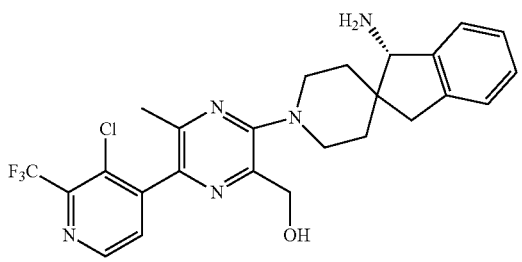
(compound 62)

The intermediate ethyl 3-chloro-6-[3-chloro-2-(trifluoromethyl)pyridin-4-yl]-5-methylpyrazine-2-carboxylate was obtained from the starting material 3-chloro-2-(trifluoromethyl)pyridine according to a method similar to step 3 of compound 47. Then the product was obtained by a method similar to steps 9-11 of example 1.

Compounds in the following table was obtained according to a method similar to example 1.

| Example | compounds | LC-MS | ¹H NMR (D6-DMSO) |
| --- | --- | --- | --- |
| 14 | | 470 | δ 7.74 (dd, J = 7.9, 1.5 Hz, 1H), 7.59-7.37 (m, 2H), 7.31 (d, J = 2.1 Hz, 1H), 7.13 (d, J = 8.2 Hz, 1H), 6.81 (dd, J = 8.2, 2.3 Hz, 1H), 5.61 (s, 1H), 5.49 (s, 1H), 5.38-5.22 (m, 1H), 4.54 (d, J = 5.9 Hz, 2H), 3.84-3.58 (m, 5H), 3.04 (t, J = 13.0 Hz, 3H), 2.69 (d, J = 15.5 Hz, 1H), 2.20 (s, 3H), 2.03 (dt, J = 52.2, 22.8 Hz, 2H), 1.49 (dd, J = 33.2, 14.9 Hz, 3H). |
| 15 | | 429.5 | δ 7.33-7.34 (m, 1H), 7.26-7.11 (m, 5H), 7.05-7.06 (m, 1H), 5.20 (t, J = 5.8 Hz, 1H), 4.53 (d, J = 5.5 Hz, 2H), 3.88 (s, 1H), 3.70-3.58 (m, 2H), 3.05 (d, J = 15.7 Hz, 3H), 2.62 (d, J = 15.6 Hz, 1H), 2.31 (s, 3H), 2.17 (s, 3H), 1.95 (s, 3H), 1.91-1.76 (m, 2H), 1.56 (d, J = 13.1 Hz, 1H), 1.24 (s, 1H), 1.16 (d, J = 13.3 Hz, 1H). |
| 16 | | 480.7 | δ 7.62-7.55 (m, 1H), 7.51-7.43 (m, 3H), 7.36 (m, 1H), 7.25-7.13 (m, 3H), 5.27 (m, 1H), 4.53 (m, 2H), 3.88 (s, 1H), 3.71 (m, 2H), 3.17-2.99 (m, 3H), 2.62 (d, J = 15.6 Hz, 1H), 2.21 (s, 3H), 1.98-1.79 (m, 2H), 1.69-1.49 (m, 2H), 1.24 (s, 1H), 1.21-1.12 (m, 1H). |
| 17 | | 440.8 | δ 13.17 (s, 1H), 8.15 (s, 1H), 8.00 (s, 1H), 7.64 (m, 2H), 7.46-7.09 (m, 4H), 5.24 (dd, J = 13.6, 5.7 Hz, 1H), 4.73-4.46 (m, 2H), 3.98 (s, 1H), 3.79-3.62 (m, 1H), 3.62-3.42 (m, 3H), 3.23-2.95 (m, 3H), 2.95-2.78 (m, 1H), 2.69 (d, J = 15.2 Hz, 1H), 1.88 (m, 2H), 1.62-1.43 (m, 2H), 1.27 (d, J = 25.4 Hz, 2H). |
| 18 | | | δ 8.15 (d, J = 21.8 Hz, 1H), 8.00 (s, 1H), 7.70 (d, J = 11.0 Hz, 2H), 7.44-7.30 (m, 1H), 7.20 (dd, J = 13.8, 10.1 Hz, 3H), 5.25 (m, 1H), 4.55 (m, 2H), 4.17-4.03 (m, 3H), 3.92 (s, 1H), 3.71 (s, 2H), 3.22-2.95 (m, 3H), 2.73-2.60 (m, 1H), 1.89 (m, 3H), 1.67-1.39 (m, 2H), 1.31-1.13 (m, 3H), 0.99-0.79 (m, 1H). |

-continued

| Example | compounds | LC-MS | ¹H NMR (D6-DMSO) |
|---|---|---|---|
| 19 | | 470 | δ 8.50 (d, J = 4.8 Hz, 1H), 7.59 (d, J = 4.8 Hz, 1H), 7.42 (d, J = 3.8 Hz, 1H), 7.24 (dd, J = 6.2, 2.9 Hz, 3H), 4.54 (s, 2H), 4.10 (s, 1H), 3.83 (d, J = 9.2 Hz, 2H), 3.14 (dd, J = 28.0, 13.6 Hz, 3H), 2.78 (d, J = 15.8 Hz, 1H), 1.97-1.78 (m, 2H), 1.57 (d, J = 13.2 Hz, 1H), 1.35 (d, J = 13.2 Hz, 1H). |
| 20 | | 483 | δ 7.74 (dd, J = 7.9, 1.7 Hz, 1H), 7.57-7.39 (m, 3H), 7.12 (d, J = 7.7 Hz, 1H), 7.05 (d, J = 7.3 Hz, 1H), 5.49 (d, J = 30.8 Hz, 2H), 5.29 (t, J = 5.6 Hz, 1H), 4.53 (d, J = 5.3 Hz, 2H), 3.70 (dd, J = 18.7, 11.9 Hz, 3H), 3.06 (t, J = 13.6 Hz, 3H), 2.81-2.65 (m, 1H), 2.30 (s, 3H), 2.20 (s, 3H), 2.01 (dd, J = 20.7, 11.3 Hz, 2H), 1.47 (d, J = 13.0 Hz, 2H). |
| 21 | | 484 | δ 8.50 (d, J = 4.9 Hz, 1H), 7.59 (d, J = 4.9 Hz, 1H), 7.14 (s, 1H), 7.07 (d, J = 7.5 Hz, 1H), 6.97 (d, J = 7.5 Hz, 1H), 5.34 (t, J = 5.7 Hz, 1H), 4.53 (d, J = 5.6 Hz, 2H), 3.97-3.54 (m, 3H), 3.11 (dd, J = 29.8, 11.1 Hz, 2H), 3.01 (d, J = 15.5 Hz, 1H), 2.57 (d, J = 15.5 Hz, 1H), 2.29 (s, 3H), 2.23 (s, 3H), 1.92 (dd, J = 12.2, 8.7 Hz, 1H), 1.85-1.73 (m, 1H), 1.55 (d, J = 12.6 Hz, 1H), 1.29-1.06 (m, 1H). |
| 22 | | 469 | δ 7.93 (d, J = 2.0 Hz, 1H), 7.72 (d, J = 8.4 Hz, 1H), 7.66 (d, J = 2.0 Hz, 1H), 7.31 (d, J = 6.0 Hz, 1H), 7.20-7.12 (m, 3H), 5.30-5.27 (t, J = 5.6 Hz, 1H), 4.60-4.44 (m, 3H), 3.86 (s, 1H), 3.82-3.66 (m, 2H), 3.06 (dd, J = 18.5, 11.6 Hz, 2H), 2.61 (d, J = 15.7 Hz, 1H), 2.47 (s, 3H), 1.95-1.85 (m, 1H), 1.80 (s, 1H), 1.54 (d, J = 13.0 Hz, 1H), 1.24 (d, J = 9.8 Hz, 2H). |
| 23 | | 434.8 | δ 7.75 (d, J = 8.0, 0.8 Hz, 1H), 7.51 (dd, J = 7.5, 1.1 Hz, 1H), 7.44-7.36 (m, 2H), 7.33 (d, J = 6.0 Hz, 1H), 7.23-7.14 (m, 3H), 5.27 (t, J = 5.7 Hz, 1H), 4.53 (d, J = 5.7 Hz, 2H), 3.89 (s, 1H), 3.71 (t, J = 14.1 Hz, 2H), 3.14-3.02 (m, 3H), 2.62 (d, J = 15.6 Hz, 1H), 2.46 (s, 1H), 2.20 (s, 3H), 1.95 (dd, J = 12.2, 8.9 Hz, 1H), 1.88-1.78 (m, 1H), 1.57 (d, J = 12.6 Hz, 1H). |

| Example | compounds | LC-MS | ¹H NMR (D6-DMSO) |
|---|---|---|---|
| 24 | | 469 | δ = 7.74 (dd, J = 7.9 Hz, 1.7, 1H), 7.49 (t, J = 7.8 Hz, 1H), 7.44 (dd, J = 7.6 Hz, 1.7 Hz, 1H), 7.39-7.33 (m, 1H), 7.26-7.15 (m, 3H), 5.29 (t, J = 5.8 Hz, 1H), 4.53 (d, J = 5.7 Hz, 2H), 3.98 (s, 1H), 3.80-3.70 (m, 2H), 3.15-3.05 (m, 3H), 2.69 (d, J = 15.8 Hz, 1H), 2.20 (s, 3H), 1.92-1.82 (m, 2H), 1.57 (d, J = 12.5 Hz, 1H), 1.27-1.24 (m, 1H). |
| 25 | | 449 | δ 7.33 (d, J = 7.3 Hz, 2H), 7.26 (d, J = 7.4 Hz, 3H), 7.24-7.15 (m, 2H), 4.74 (s, 2H), 3.80-3.70 (m, 2H), 3.72 (d, J = 7.6 Hz, 1H), 3.46 (d, J = 16.2 Hz, 2H), 3.12 (dd, J = 33.1, 10.6 Hz, 2H), 2.92 (d, J = 16.3 Hz, 1H), 2.48 (d, J = 3.6 Hz, 3H), 2.33 (d, J = 3.1 Hz, 3H), 2.03 (dd, J = 26.6, 12.3 Hz, 2H), 1.61 (t, J = 14.9 Hz, 2H). |
| 26 | | 439.8 | δ 11.60 (s, 1H), 7.62 (d, J = 7.9 Hz, 1H), 7.47 (d, J = 8.1 Hz, 1H), 7.34 (d, J = 7.2 Hz, 1H), 7.23-7.12 (m, 4H), 7.07-6.98 (m, 1H), 6.89 (d, J = 2.0 Hz, 1H), 5.19 (m, 1H), 4.65 (d, J = 5.6 Hz, 2H), 3.89 (s, 1H), 3.57 (m, 2H), 3.14-3.01 (m, 3H), 2.72 (s, 3H), 2.63 (d, J = 15.5 Hz, 1H), 2.00-1.89 (m, 1H), 1.83 (m, 1H), 1.57 (d, J = 13.5 Hz, 1H). |

The compound in the following table was obtained according to a method similar to example 2.

| Example | compounds | LC-MS | 1H NMR (D6-DMSO) |
|---|---|---|---|
| 27 | | 512 | δ 8.41 (s, 2H), 7.74 (d, J = 7.8 Hz, 1H), 7.66 (d, J = 4.9 Hz, 1H), 7.47 (dd, J = 11.0, 9.3, 4.2 Hz, 2H), 7.37-7.15 (m, 2H), 4.71 (d, J = 42.8 Hz, 2H), 4.52 (s, 2H), 3.94-3.60 (m, 4H), 3.14 (dd, J = 20.8, 13.2 Hz, 2H), 3.00 (d, J = 15.7 Hz, 1H), 2.80-2.59 (m, 1H), 2.20 (s, 3H), 1.87 (dd, J = 29.9, 11.6 Hz, 2H), 1.60 (dd, J = 28.0, 13.4 Hz, 1H), 1.29 (dd, J = 24.4, 12.9 Hz, 1H). |

-continued

| Example | compounds | LC-MS | 1H NMR (D6-DMSO) |
|---|---|---|---|
| 28 | | 549 | δ 7.81-7.70 (m, 1H), 7.48 (dd, J = 17.1, 9.3 Hz, 1H), 7.44-7.35 (m, 2H), 7.26 (d, J = 6.6 Hz, 1H), 7.22-7.10 (m, 1H), 5.39-5.24 (m, 1H), 4.53 (d, J = 4.5 Hz, 2H), 4.00 (s, 1H), 3.62 (d, J = 10.7 Hz, 1H), 3.50 (d, J = 10.7 Hz, 1H), 3.30-3.16 (m, 2H), 3.06 (d, J = 16.0 Hz, 1H), 2.94 (d, J = 16.0 Hz, 1H), 2.20 (s, 3H), 2.01 (d, J = 7.5 Hz, 1H), 1.87-1.74 (m, 1H), 1.59-1.38 (m, 2H). |
| 29 | | 560 | δ 7.74 (dd, J = 9.6, 3.3 Hz, 1H), 7.61 (d, J = 7.3 Hz, 1H), 7.54-7.40 (m, 2H), 7.32 (s, 1H), 7.03 (d, J = 7.9 Hz, 1H), 6.79 (d, J = 7.8 Hz, 1H), 5.61-5.31 (m, 2H), 5.28 (t, J = 5.8 Hz, 1H), 4.61-4.49 (m, 2H), 3.84-3.52 (m, 2H), 3.22 (d, J = 13.7 Hz, 6H), 3.11-2.93 (m, 3H), 2.47 (s, 3H), 2.16-1.79 (m, 2H), 1.62-1.40 (m, 2H). |
| 30 | | 494 | δ 7.82 (t, J = 7.0 Hz, 1H), 7.75 (dd, J = 7.9, 1.7 Hz, 1H), 7.59-7.35 (m, 4H), 5.35 (dd, J = 9.4, 5.2 Hz, 1H), 4.55 (d, J = 5.7 Hz, 1H), 3.26-3.07 (m, 4H), 2.21 (s, 4H), 2.01 (dd, J = 14.5, 6.8 Hz, 3H), 1.91 (s, 2H), 1.68-1.52 (m, 2H). |
| 31 | | 547 | δ 7.84 (s, 1H), 7.79 (dd, J = 7.8, 1.6 Hz, 1H), 7.74 (dd, J = 7.8, 1.7 Hz, 1H), 7.55-7.46 (m, 2H), 7.44 (dd, J = 7.6, 1.7 Hz, 1H), 5.66 (d, J = 6.2 Hz, 1H), 5.29 (t, J = 5.7 Hz, 1H), 4.79 (d, J = 6.1 Hz, 1H), 4.53 (d, J = 5.7 Hz, 2H), 3.70 (t, J = 14.7 Hz, 2H), 3.20 (d, J = 7.6 Hz, 3H), 3.14 (dd, J = 16.2, 5.4 Hz, 3H), 2.76 (d, J = 16.5 Hz, 1H), 2.20 (s, 3H), 1.92 (dd, J = 21.1, 11.1 Hz, 2H), 1.64 (d, J = 12.9 Hz, 1H), 1.27 (d, J = 14.8 Hz, 1H). |

-continued

| Example | compounds | LC-MS | 1H NMR (D6-DMSO) |
|---|---|---|---|
| 32 | | 547 | δ 7.86 (s, 1H), 7.74 (dd, J = 7.9, 1.6 Hz, 1H), 7.49 (t, J = 7.8 Hz, 1H), 7.46-7.39 (m, 2H), 7.21 (d, J = 8.1 Hz, 1H), 5.66 (d, J = 34.7 Hz, 2H), 5.29 (t, J = 5.9 Hz, 1H), 4.53 (d, J = 5.6 Hz, 2H), 3.82-3.66 (m, 3H), 3.09 (t, J = 13.9 Hz, 3H), 2.82-2.63 (m, 1H), 2.20 (s, 3H), 2.03 (d, J = 9.0 Hz, 2H), 1.47 (dd, J = 23.3, 13.7 Hz, 2H). |
| 33 | | 503 | δ 7.74 (dd, J = 7.8, 1.7 Hz, 1H), 7.53-7.40 (m, 2H), 7.34 (s, 1H), 7.21 (t, J = 5.4 Hz, 2H), 5.29 (t, J = 5.7 Hz, 1H), 4.52 (d, J = 5.7 Hz, 2H), 3.89 (s, 1H), 3.74 (dd, J = 16.9, 13.4 Hz, 2H), 3.17-2.96 (m, 3H), 2.59 (d, J = 15.7 Hz, 1H), 2.20 (s, 3H), 1.95 (td, J = 12.5, 3.9 Hz, 1H), 1.81 (t, J = 10.6 Hz, 1H), 1.58 (d, J = 13.1 Hz, 1H), 1.14 (d, J = 13.0 Hz, 1H). |
| 34 | | 537 | δ 7.74 (dd, J = 7.8, 1.7 Hz, 1H), 7.67 (s, 1H), 7.54 (d, J = 8.1 Hz, 1H), 7.49 (t, J = 7.7 Hz, 1H), 7.46-7.38 (m, 2H), 5.30 (t, J = 5.8 Hz, 1H), 4.53 (d, J = 5.6 Hz, 2H), 3.99 (s, 1H), 3.83-3.65 (m, 2H), 3.20-3.02 (m, 3H), 2.79-2.62 (m, 2H), 2.33 (dd, J = 6.7, 4.9 Hz, 1H), 2.19 (d, J = 6.0 Hz, 3H), 2.02-1.92 (m, 1H), 1.83 (t, J = 10.5 Hz, 1H), 1.60 (d, J = 12.6 Hz, 1H), 1.16 (d, J = 13.4 Hz, 1H). |
| 35 | | 470 | δ 8.38 (d, J = 4.9 Hz, 1H), 7.74 (dd, J = 7.9, 1.7 Hz, 1H), 7.64 (d, J = 7.6 Hz, 1H), 7.56-7.37 (m, 2H), 7.27-7.17 (m, 1H), 5.30 (t, J = 5.4 Hz, 1H), 4.53 (d, J = 5.2 Hz, 2H), 4.00 (s, 1H), 3.80-3.64 (m, 2H), 3.24-3.03 (m, 3H), 2.71 (d, J = 15.9 Hz, 1H), 2.20 (s, 3H), 1.95 (d, J = 10.3 Hz, 2H), 1.64 (d, J = 12.3 Hz, 1H), 1.23 (d, J = 7.9 Hz, 1H). |

-continued

| Example | compounds | LC-MS | 1H NMR (D6-DMSO) |
|---|---|---|---|
| 36 | 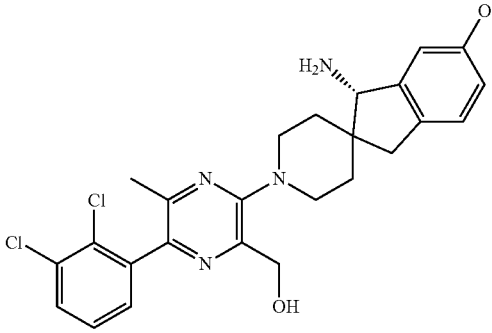 [SMILES: Cc1nc(N2CCC3(CC2)Cc2ccc(Cl)cc2[C@H]3N)c(CO)nc1-c1cccc(Cl)c1Cl] | 553 | δ 7.74 (dd, J = 7.8, 1.7 Hz, 1H), 7.51-7.46 (m, 2H), 7.33-7.29 (m, 2H), 7.16-7.14 (m, 1H), 5.29 (t, J = 5.8 Hz, 1H), 4.53 (d, J = 5.6 Hz, 2H), 3.97-3.94 (m, 1H), 3.78-3.71 (m, 2H), 3.20-3.02 (m, 3H), 2.68-2.61 (m, 2H), 2.20 (s, 3H), 2.02-1.80 (m, 2H), 1.60 (d, J = 12.6 Hz, 1H). |

The compounds listed in the following table was obtained according to a method similar to example 13.

| Example | compounds | LC-MS | $^1$H NMR (D6-DMSO) |
|---|---|---|---|
| 37 | 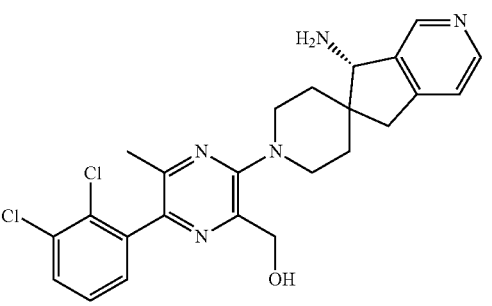 [SMILES: Cc1nc(N2CCC3(CC2)Cc2ccncc2[C@H]3N)c(CO)nc1-c1cccc(Cl)c1Cl] | 471 | δ 8.42 (s, 1H), 8.36 (d, J = 5.8 Hz, 1H), 7.74 (dd, J = 7.8, 1.6 Hz, 1H), 7.58-7.40 (m, 3H), 4.52 (s, 2H), 4.04 (s, 1H), 3.83-3.64 (m, 2H), 3.23 (d, J = 17.4 Hz, 1H), 3.17-2.97 (m, 3H), 2.79 (d, J = 17.2 Hz, 1H), 2.20 (s, 3H), 1.99-1.79 (m, 2H), 1.61 (d, J = 13.4 Hz, 1H), 1.15 (d, J = 13.0 Hz, 1H). |
| 38 | 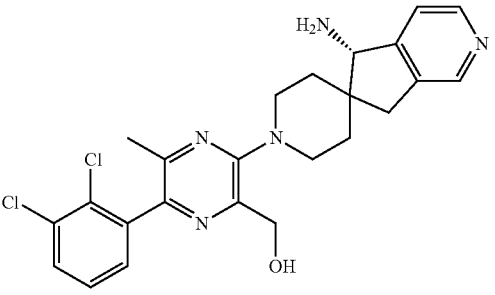 [SMILES: Cc1nc(N2CCC3(CC2)Cc2cnccc2[C@H]3N)c(CO)nc1-c1cccc(Cl)c1Cl] | 470 | δ 8.43 (d, J = 4.5 Hz, 2H), 7.74 (dd, J = 7.9, 1.7 Hz, 1H), 7.59 (d, J = 5.9 Hz, 1H), 7.49 (t, J = 7.8 Hz, 1H), 7.44 (dd, J = 7.6, 1.7 Hz, 1H), 5.99 (d, J = 6.4 Hz, 1H), 5.30 (t, J = 5.7 Hz, 1H), 4.84 (d, J = 5.7 Hz, 1H), 4.52 (d, J = 5.7 Hz, 2H), 3.73 (dd, J = 27.9, 13.3 Hz, 2H), 3.21 (d, J = 16.3 Hz, 1H), 3.17-2.96 (m, 2H), 2.83-2.63 (m, 1H), 2.20 (s, 3H), 2.06-1.82 (m, 2H), 1.70 (d, J = 13.4 Hz, 1H). |
| 39 | 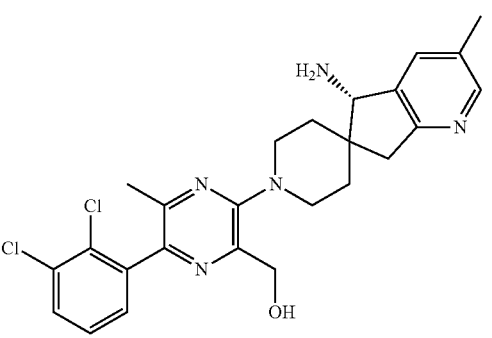 [SMILES: Cc1cnc2c(c1)[C@@H](N)C1(CCN(c3nc(C)c(-c4cccc(Cl)c4Cl)nc3CO)CC1)C2] | 484 | δ 8.16 (s, 1H), 7.74 (dd, J = 7.8, 1.7 Hz, 1H), 7.47 (ddd, J = 9.4, 7.6, 2.6 Hz, 3H), 5.30 (t, J = 5.5 Hz, 1H), 4.53 (d, J = 5.0 Hz, 2H), 3.92 (s, 1H), 3.75 (dd, J = 13.0, 4.8 Hz, 2H), 3.21-2.94 (m, 3H), 2.69 (d, J = 16.1 Hz, 1H), 2.28 (s, 3H), 2.20 (s, 3H), 1.91 (ddd, J = 25.9, 17.3, 6.3 Hz, 2H), 1.58 (d, J = 12.7 Hz, 1H), 1.31-1.07 (m, 2H). |

The compounds in the following table were prepared by the above method.

| Example | Compounds | LC-MS |
|---|---|---|
| 40 | | 471 |
| 41 | | 466 |
| 42 | | 514 |
| 43 | | 471 |
| 44 | | 437 |

-continued
| Example | Compounds | LC-MS |
|---|---|---|
| 45 | 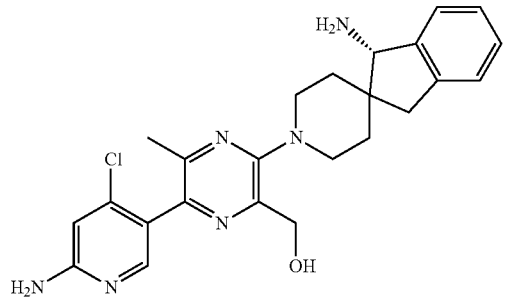 | 452 |
| 46 | 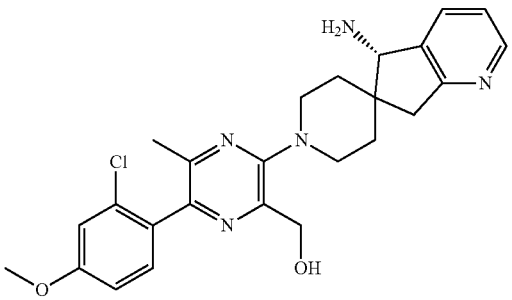 [SMILES: COc1ccc(-c2nc(CO)c(N3CCC4(CC3)Cc3ccccc3[C@H]4N)nc2C)c(Cl)c1] | 467 |
| 47 | 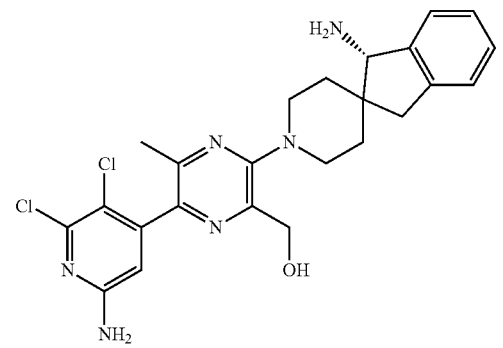 [SMILES: Cc1nc(N2CCC3(CC2)Cc2ccccc2[C@H]3N)c(CO)nc1-c1cc(N)nc(Cl)c1Cl] | 486 |
| 48 | 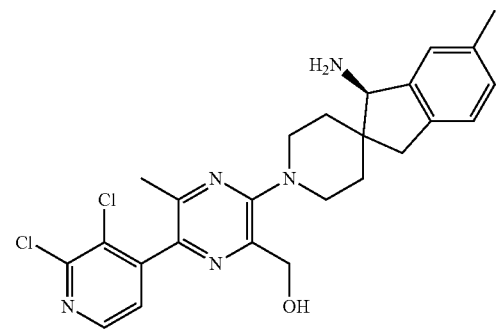 [SMILES: Cc1ccc2c(c1)[C@H](N)C1(CCN(c3nc(C)c(-c4ccnc(Cl)c4Cl)nc3CO)CC1)C2] | 485 |

-continued
| Example | Compounds | LC-MS |
|---|---|---|
| 49 | 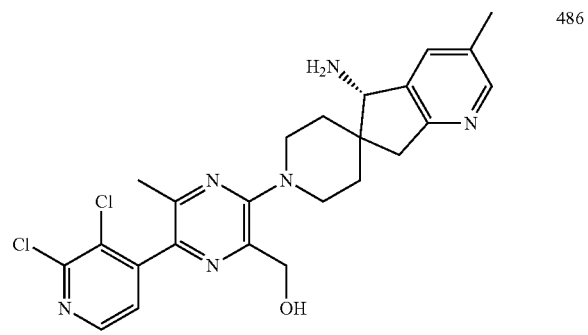 | 486 |
| 50 | 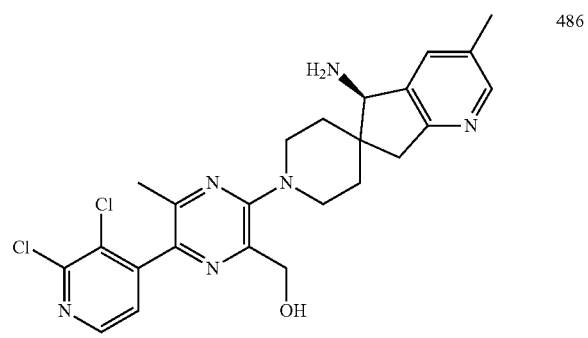 | 486 |
| 51 | 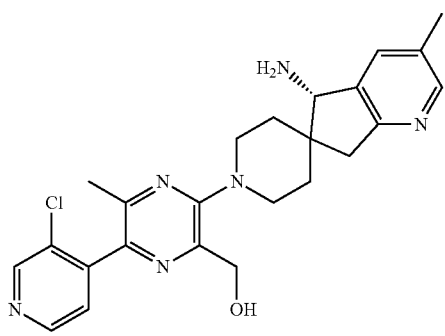 [SMILES: Cc1cnc2c(c1)[C@@H](N)C1(CCN(c3nc(C)c(-c4ccncc4Cl)nc3CO)CC1)C2] | 452 |
| 52 | 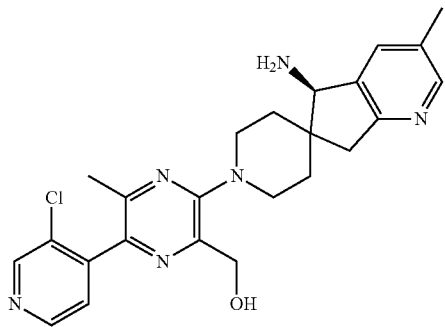 [SMILES: Cc1cnc2c(c1)[C@H](N)C1(CCN(c3nc(C)c(-c4ccncc4Cl)nc3CO)CC1)C2] | 452 |

-continued

| Example | Compounds | LC-MS |
|---|---|---|
| 53 | | 500 |
| 54 | | 466 |
| 55 | | 451 |
| 56 | | 467 |
| 57 | | 453 |

-continued
| Example | Compounds | LC-MS |
|---|---|---|
| 58 | 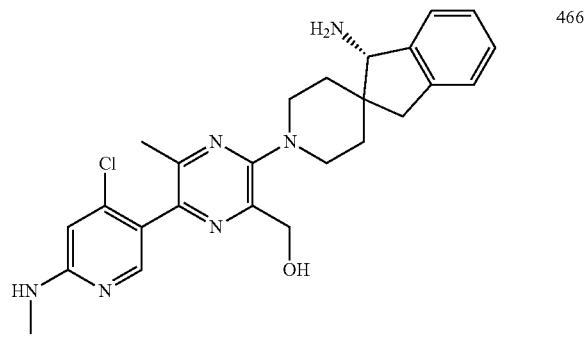 | 466 |
| 59 | 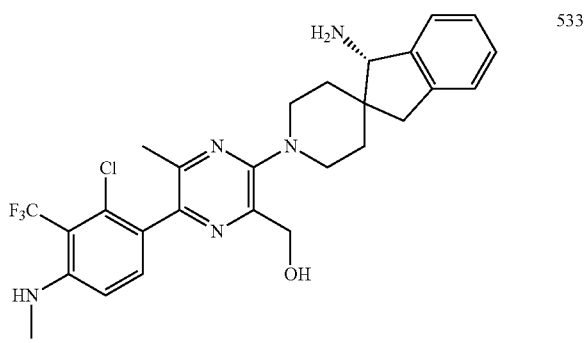 | 533 |
| 60 | 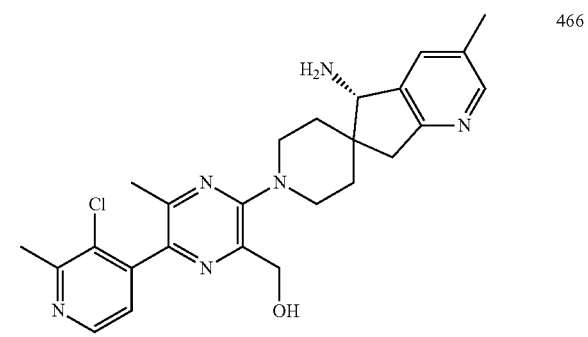 | 466 |
| 61 | 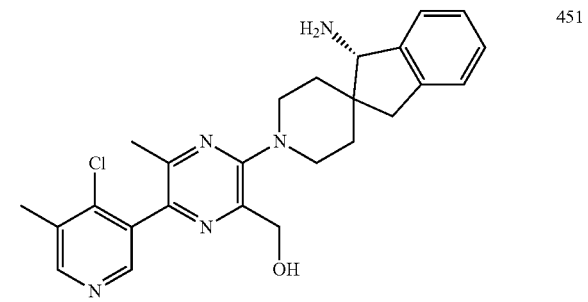 | 451 |

-continued
| Example | Compounds | LC-MS |
|---|---|---|
| 62 | 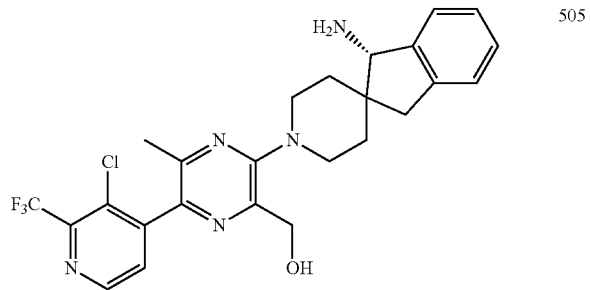 | 505 |
| 63 | 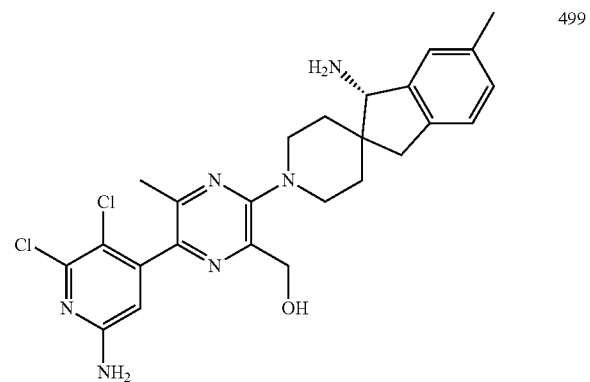 | 499 |
| 64 | 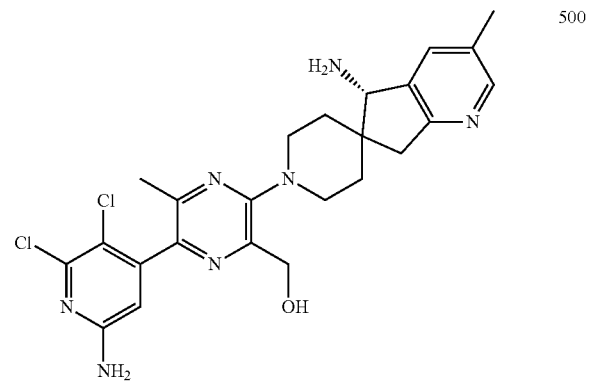 | 500 |
| 65 | 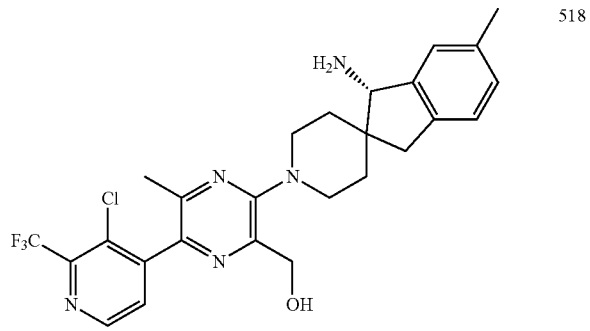 | 518 |

-continued

| Example | Compounds | LC-MS |
|---|---|---|
| 66 | | 505 |
| 67 | | 519 |
| 68 | | 500 |
| 69 | | 519 |
| 70 | | 533 |

-continued
| Example | Compounds | LC-MS |
|---|---|---|
| 71 | 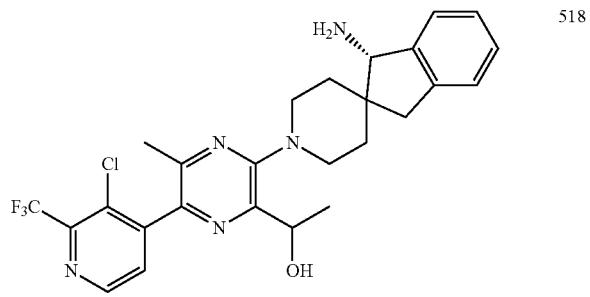 | 518 |
| 72 | 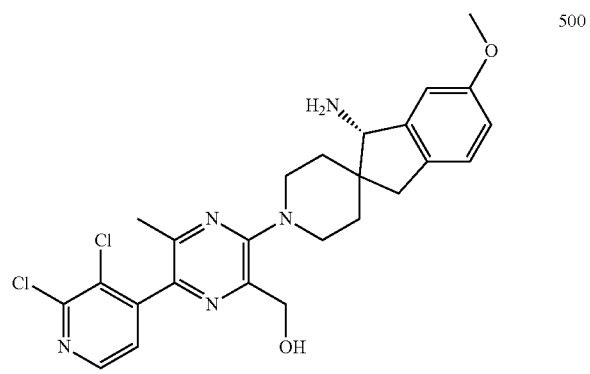 | 500 |
| 73 | 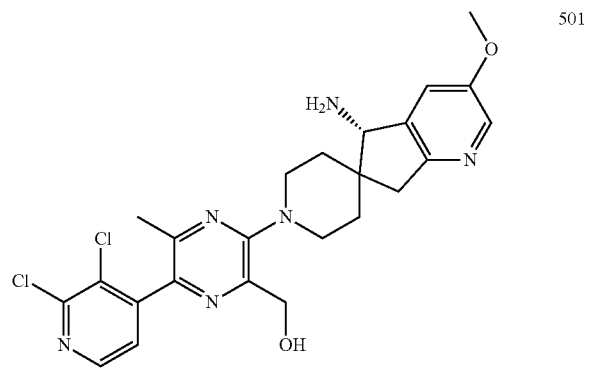 | 501 |
| 74 | 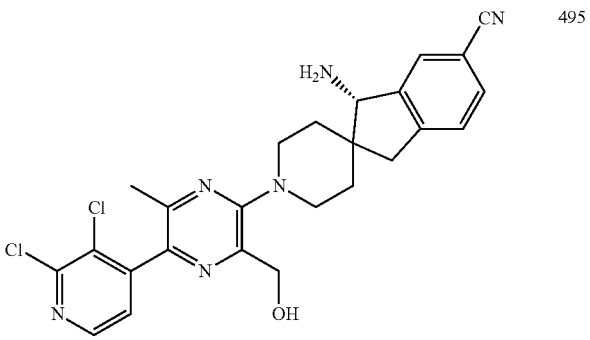 | 495 |

-continued

| Example | Compounds | LC-MS |
|---|---|---|
| 75 | | 466 |
| 76 | | 481 |
| 77 | | 461 |

Example I

Biological Activity Experiment

1. Detection of In Vitro Protein Activity of Compounds

The screening method of SHP2 protein activity was established by fluorescence detection. The basic principle is: SHP2 as phosphatase can catalyze the dephosphorization of DiFMUP to form DiFMU and free phosphate groups. The product DiFMU emits fluorescence under 340 nm excitation, and 450 nm emission is collected. If the binding of small molecule compounds with SHP2 can inhibit the activity of SHP2 enzyme, the 450 nm emission light detected will be weakened, and the activity of SHP2 enzyme will be finally reflected by the intensity of fluorescence value.

The specific operation was as follows: the 10 mM compound stock solution was diluted to 1 mM with DMSO, and then diluted 3 times with DMSO. 95 µL reaction buffer (60 mM HEPES), 75 mM NaCl, 75 mM KCl, 1 mM EDTA, 5 mM DTT, 1 µL gradient diluted compound, 2 µL SHP2 (concentration was 2 µg/µL) and 1 µL polypeptide (concentration was 50 mM) were added into each well of a 96 well flat clear bottom black plate (costar, 3603). The above test mixture was incubated at room temperature in dark for 60 minutes. Then 2 µL of 10 mM DiFMUP was added into each well, and was incubated at room temperature for 30 minutes. Fluorescence value was determined in the enzyme reader at Ex340/Em450. $IC_{50}$ of the compounds was obtained by the data analysis software Prism.

2. Cell Proliferation Assay of the Compound

Cell proliferation inhibition screening method was established by CellTier-Glu® test reagent from Promega.

Human non-small cell lung cancer NCI-H358 was cultured by RPMI-1640 (Gibco®) medium with 10% fetal bovine serum (Gibco®) at 37° C., 95% air and 5% $CO_2$, in 25 $cm^2$ or 75 $cm^2$ plastic culture bottle ((Nunc®) and passaged 2-3 times a week.

The cells were seeded on the 96 well cell culture plate (Nunc®) at the density of $2*10^3$/well, 90 µL/well, and cultured at 37° C., 95% air and 5% $CO_2$. The compound to be tested was added 24 hours later: the compound was diluted 3 times with DMSO from the concentration of 2 mM compound (dissolved in DMSO). 5 µL of the compound at each concentration was added into 45 µL complete medium containing 1% DMSO. 10 µL of the compound diluted by culture medium was added into the culture plate seeded with cells. The final concentration of DMSO in cell culture medium was 0.1%, and the final concentration of test compound was 0.3 nM-2 µM. The cells were incubated at 37° C. for 3 days. The culture medium was substituted with 90 μL/well fresh complete medium. According to the above diluting method of compounds, the compound to be tested was added.

After 5 days, cell viability was tested by CellTiter-Glu (Promega) kit, and finally, the semi-inhibitory concentration of compounds on cell proliferation, i.e. $IC_{50}$ was calculated by Prism program.

Biological data of some candidate compounds were analyzed, the result was listed in the following table.

| Proteinase activity | | |
|---|---|---|
| Compounds No. | SHP2 IC50 (nM) | H358 IC50 (nM) |
| 1 | 9 | 88 |
| 2 | 35 | 84 |
| 3 | — | 273 |
| 4 | | 817 |
| 5 | | 98 |
| 6 | | >1000 |
| 7 | | >1000 |
| 8 | | >1000 |
| 9 | | >1000 |
| 10 | | >1000 |
| 11 | | 405 |
| 12 | | >1000 |
| 13 | | 1.6 |
| 14 | | 56 |
| 15 | | 590 |
| 16 | | 261 |
| 17 | | 464 |
| 18 | | 630 |
| 19 | | 29 |
| 20 | | 48 |
| 21 | | 11 |
| 22 | | 195 |
| 23 | | 479 |
| 24 | | >1000 |
| 25 | | 37 |
| 26 | | 449 |
| 27 | | >1000 |
| 28 | | >1000 |
| 29 | | 199 |
| 30 | | 207 |
| 31 | | 249 |
| 32 | | 29 |
| 33 | | 17 |
| 34 | | 90 |
| 35 | | 101 |
| 36 | | 31 |
| 37 | | 75 |
| 38 | | >1000 |
| 39 | | 11 |
| 40 | | 30 |
| 41 | | 97 |
| 42 | | 732 |
| 43 | | 225 |
| 44 | | >1000 |
| 45 | | >1000 |
| 46 | | 379 |
| 47 | | 30 |
| 48 | | >1000 |
| 49 | | 28 |
| 50 | | 453 |
| 51 | | 81 |
| 52 | | >1000 |
| 53 | | 328 |
| 54 | | 83 |
| 55 | | >1000 |
| 56 | | 182 |
| 57 | | >1000 |
| 58 | | >1000 |
| 59 | | 115 |
| 60 | | 75 |
| 61 | | 63 |
| 62 | | 15 |
| 63 | | 40 |
| 64 | | 22 |
| 68 | | 530 |
| 72 | | 65.9 |
| 76 | | 25 |
| 77 | | 33 |

3. hERG Inhibitory Activity of the Compounds

Patch Clamp Amplifier System (Multiclamp 700B Amplifier) (AXON), Olympus microscope (Olympus IX51/71/73), and MP285 micromanipulator were used.

HEK293 cell line for transfecting hERG was purchased from Invitrogen Company. The cells were grown in the culture medium with 85% DMEM, 10% fetal bovine serum, 0.1 mM NEAA, 25 mM HEPES buffer, 100 U/mL penicillin-streptomycin, 5 μg/mL blasticidin and 400 μg/mL G418 geneticin.

The cells were passaged three times a week and digested with TrypLE Express to maintain a fusion degree of about 40% to 80%. Before testing, the cells were seeded at the density of $5*10^5$ cells/petri dish with a diameter of 6 cm and the cells were induced with 1 μg/ml doxycycline for 48 hours.

The test concentration of the compound solution was 30, 10, 2, 0.5, 0.1 μM after 1000-fold dilution and the final concentration of DMSO was in the range of 0.1%.

The manipulator was adjusted to move the electrode tip to the cell surface to form a high sealing. Liquid connection potential and fast capacitance were compensated, and the cell membrane was broken to form a whole cell recording mode. The membrane potential was set as −60 mV to ensure that the HERG channel was not opened. $C_{slow}$ on the amplifier was used to eliminate the peak of capacity current. Holding voltage was set as −90 MV for 500 ins. The leakage current test was performed at −80 mV for 500 ms. +30 mV was depolarized for 4.8 seconds, and HERG channel was activated. The voltage was restored to −50 mV for 5.2 seconds, and the tail current was observed.

Peak current suppression=[1−(peak tail current$_{inhibitor}$−peak tail current$_{positive\ control}$)/(peak tail current$_{blank}$−peak tail current$_{positive\ control}$)]*100

The dose response curve of hERG current inhibition rate versus the concentration of the tested compound was plotted by using Graphpad Prism 8.0 software. The candidate compounds were analyzed and the result was shown in the table below.

| hERG inhibition data | |
|---|---|
| Compound No. | hERG IC50 (μM) |
| 1 | <0.1 |
| 13 | <0.1 |
| 21 | 3.03 |
| 47 | 4.29 |
| 49 | 1.80 |
| 62 | 4.23 |
| 64 | 6.13 |
| 72 | 2.59 |
| 76 | 2.11 |
| 77 | 0.62 |

We claim:

1. An optical isomer compound of SHP2 phosphatase allosteric inhibitor of formula (I), or a pharmaceutically acceptable salt thereof:

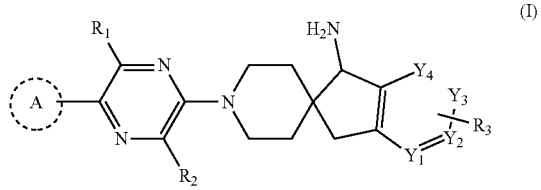

(I)

wherein,

is a substituted or unsubstituted phenyl, indazolyl or pyridyl; $R_1$ and $R_2$ are each independently selected from —$CH_3$, —$NH_2$, —$CH_2OH$, —$C(O)O(CH_2)_nCH_3$, —CN, —H, —OH, —$C(O)NH_2$ or —$CH(OH)CH_3$; $R_3$ is selected from H, $C_{1-6}$ alkyl, —$CF_3$, halogen, —$SO_2CH_3$, —$OCH_3$, —CN, —$C(O)NH_2$, —$NH_nSO_{3-m}(CH_3)_m$, —$CH_n(CH_3)_mOH$, —$OCF_3$ or —$C(O)CH_3$;

$Y_1$, $Y_2$, $Y_3$ and $Y_4$ are each independently selected from —C— or —N—; n=0 or 1; and m=1 or 2.

2. The compound or pharmaceutically acceptable salt of claim 1, wherein, the inhibitor compound has the structure of formula (II):

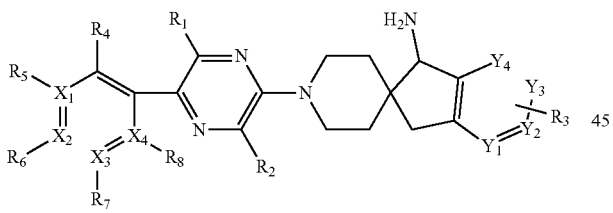

(II)

wherein $X_1$, $X_2$, $X_3$ or $X_4$ is each independently selected from C or N; $R_1$ and $R_2$ are each independently selected from —H, —$CH_3$, —$NH_2$, —$C(O)O(CH_2)_nCH_3$, —CN, —OH, —$CH_2OH$, —$C(O)NH_2$ or —$CH(OH)CH_3$; $R_3$ is selected from H, $C_{1-6}$ alkyl, —$CF_3$, halogen, —$SO_2CH_3$, —$OCH_3$, —CN, —$C(O)NH_2$, —$NHSO_2CH_3$, —$NSO(CH_3)_2$, —$CH_n(CH_3)_{2-n}OH$, —$C(O)CH_3$ or —$OCF_3$; $R_4$, $R_5$, $R_6$, $R_7$ and $R_8$ are each independently selected from —H, —Cl, —$CH_3$, —Br, —$CF_3$, $CH_3O$—, $CH_3SO_2$—, =O, $CH_3NH$— and —$NH_2$; $Y_1$, $Y_2$, $Y_3$ and $Y_4$ are each independently selected from C or N; and n=0 or 1.

3. The compound or pharmaceutically acceptable salt of claim 2, wherein, $R_1$ is selected from —$CH_3$ or —$NH_2$; $R_2$ is selected from —$CH_2OH$, —$C(OH)CH_3$, —$C(O)O(CH_2)_nCH_3$, —CN, —H or —$C(O)NH_2$.

4. The compound or pharmaceutically acceptable salt of claim 1, wherein the compound has the structure of formula (III):

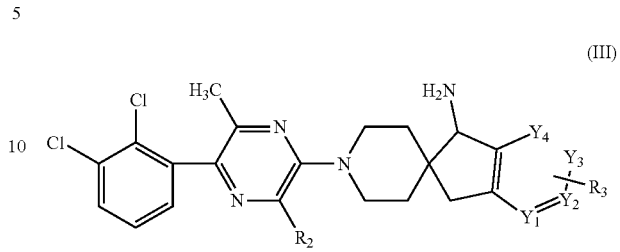

(III)

wherein $R_2$ is selected from —$C(O)O(CH_2)_nCH_3$, —$CH_2OH$ or —$CH(OH)CH_3$; $Y_1$, $Y_2$, $Y_3$ and $Y_4$ are each independently selected from N or C; $R_3$ is selected from H, halogen, —CN, —$CONH_2$, —$NSO(CH_3)_2$, —$CF_3$, —$CH_3$, —$OCF_3$, —$SO_2CH_3$ or —$OCH_3$.

5. The compound or pharmaceutically acceptable salt of claim 1, wherein the compound has the structure of formula (IV)

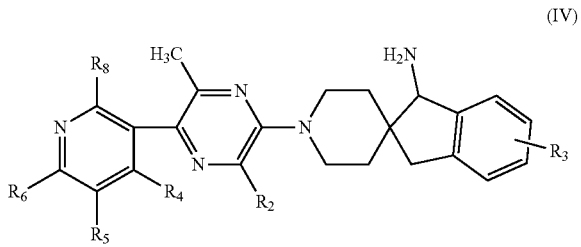

(IV)

wherein $R_4$, $R_5$, $R_6$ or $R_8$ is each independently selected from —H, —$CH_3$, $CH_3NH$—, —$NH_2$, —Cl, $CH_3O$— and —$CF_3$; $R_3$ is selected from H, —$CH_3$, —$OCH_3$, —CN or halogen; $R_2$ is selected from —$CH_2OH$ or —$C(O)O(CH_2)_nCH_3$; and n=1.

6. The compound or pharmaceutically acceptable salt of claim 1, wherein the compound has the structure of formula (V)

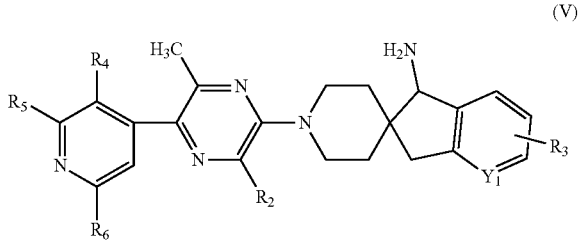

(V)

wherein $R_2$ is selected from —$CH_2OH$, —$CHOHCH_3$ or —$C(O)O(CH_2)_nCH_3$; $Y_1$ is selected from C or N; $R_3$ is selected from H, —$CH_3$, —$OCH_3$, —CN or halogen; $R_4$, $R_5$ and $R_6$ are each independently selected from —H, halogen, —$CH_3$, —$CF_3$, —$OCH_3$, —CN, —NHR, —$N(CH_3)_2$ or —$NH_2$; n=0 or 1; and R is $C_1$-$C_3$ alkyl or cycloalkyl.

7. The compound or pharmaceutically acceptable salt of claim 1, wherein the compound has the structure of the formula (VI)

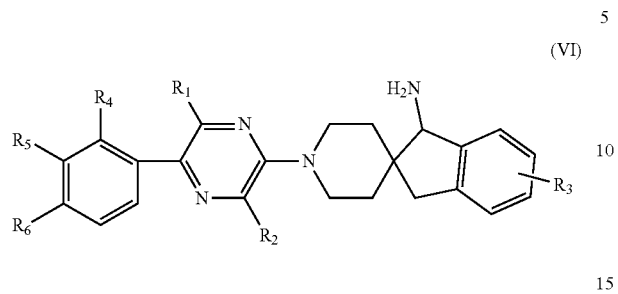

(VI)

wherein R₁ is selected from —CH₃ or H; R₂ is selected from —CH₂OH or —C(O)OCH₃; R₃ is selected from H, halogen, —CF₃, —OCH₃, —OCF₃, —CN, —C(O)NH₂, —NH$_n$SO$_{3-m}$(CH₃)$_m$, C$_{1-6}$ alkyl or CH₃SO₂—; R₄, R₅ or R₆ is each independently selected from H, halogen, —CF₃, alkoxyl, CH₃NH—, CH₃SO₂—, or C$_{1-3}$ substituted or unsubstituted alkyl; n=0 or 1, and m=1 or 2.

8. The compound or pharmaceutically acceptable salt of the claim 1, wherein the compound has the structure comprising:

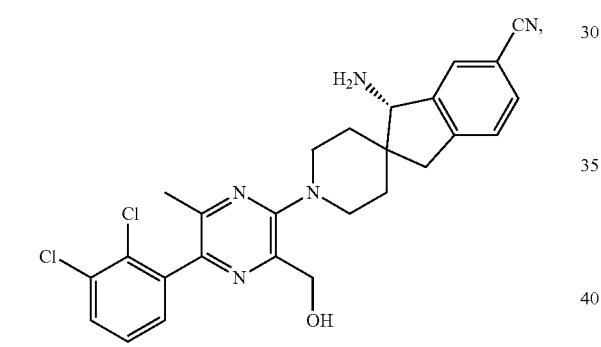

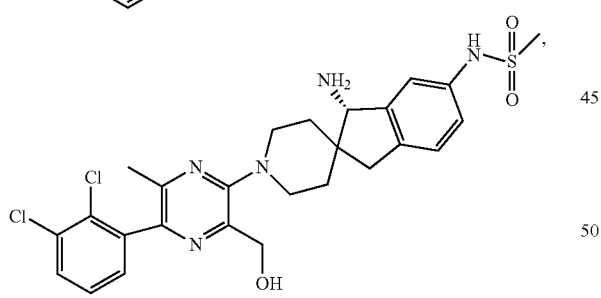

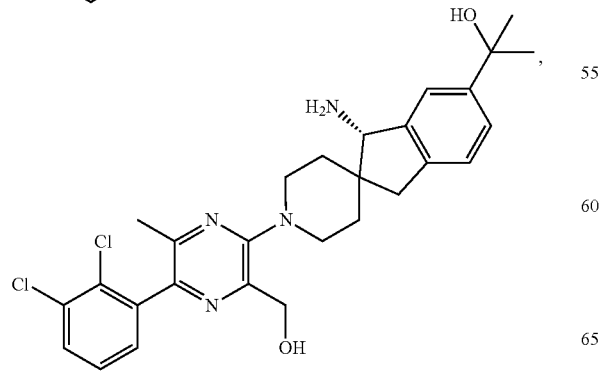

-continued

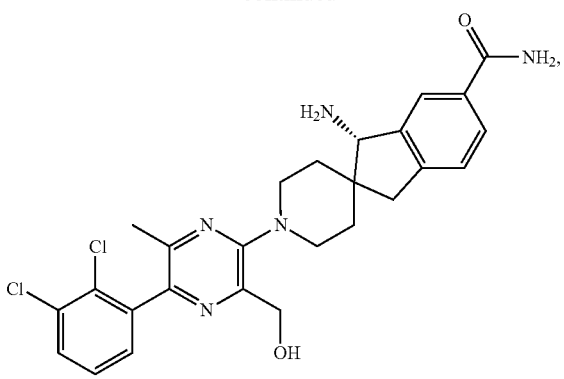

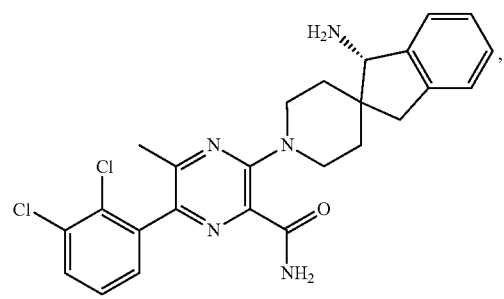

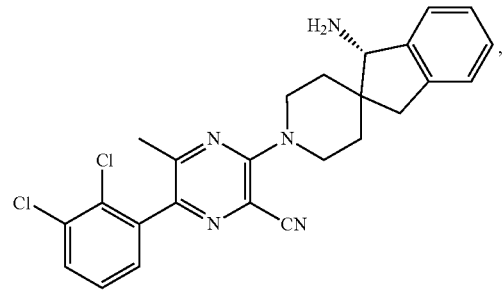

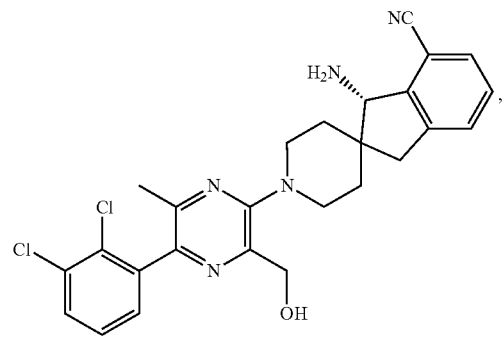

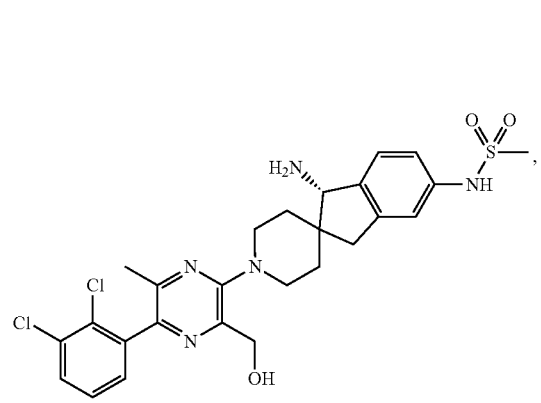

103
-continued
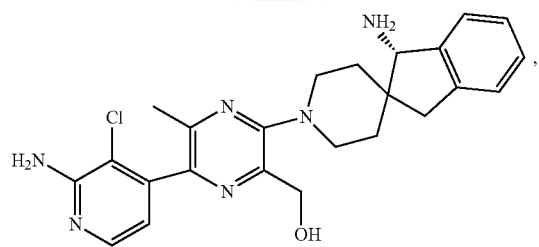
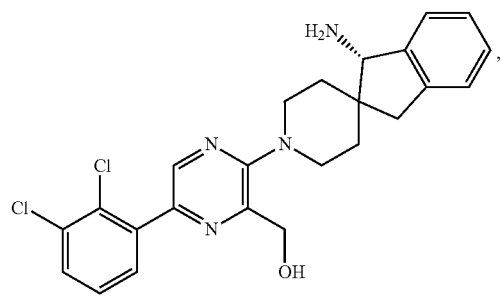
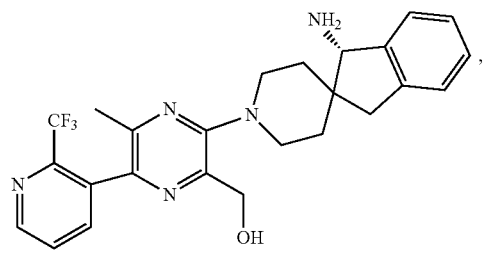
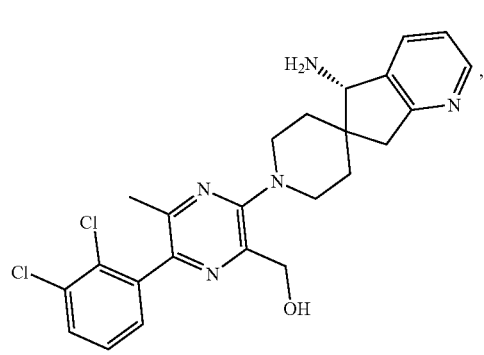
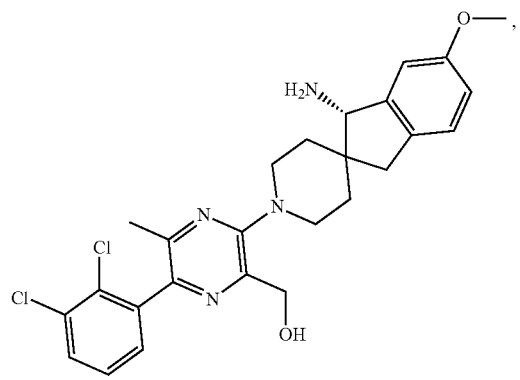
104
-continued
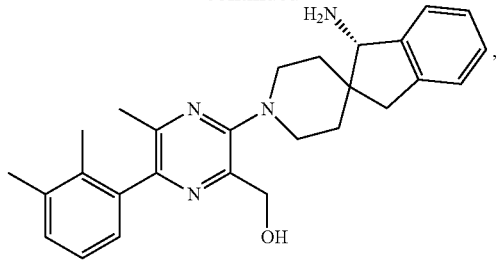
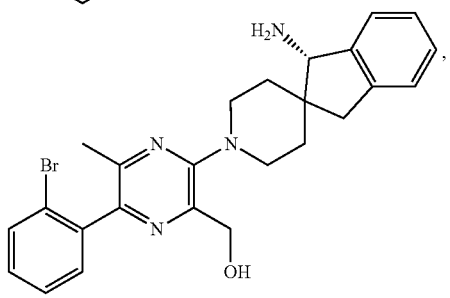
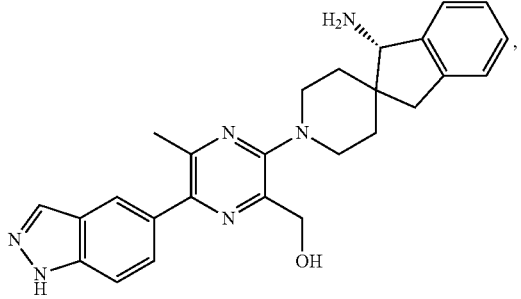
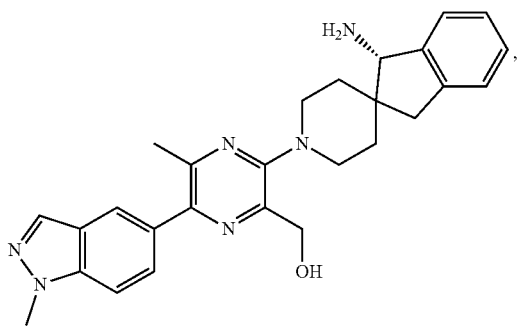
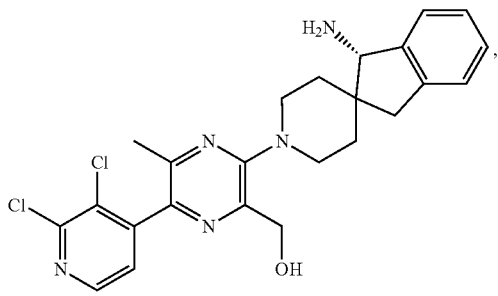

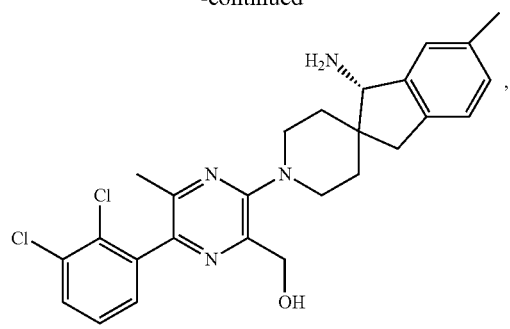
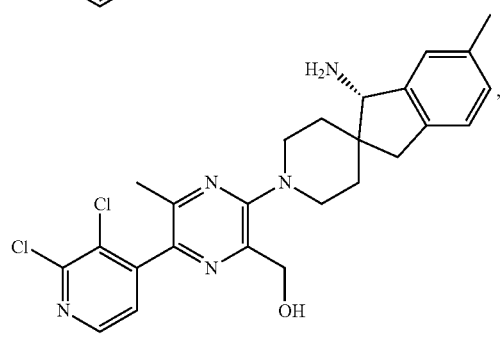
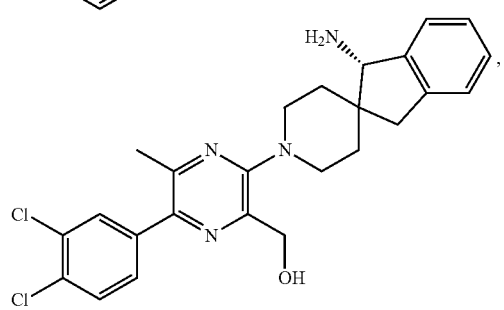
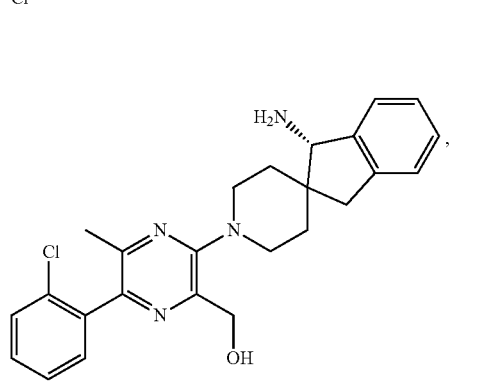
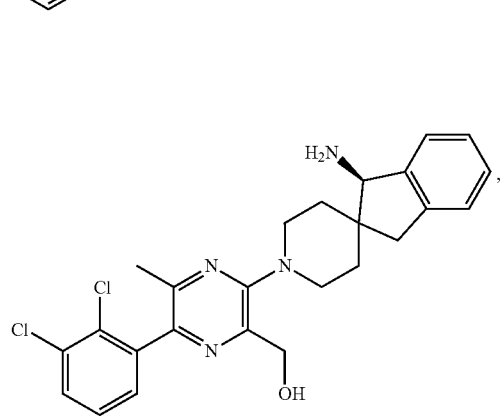
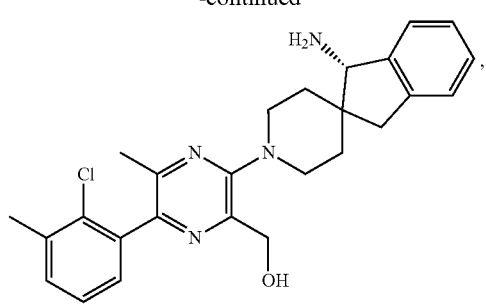
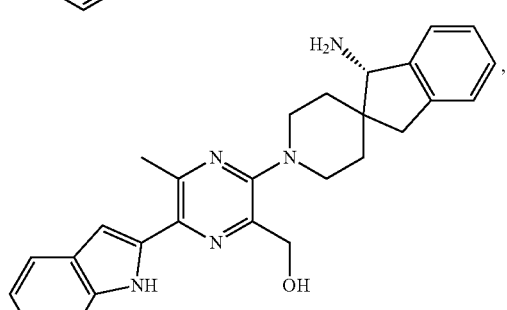
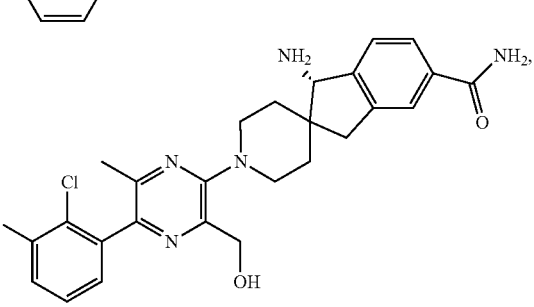
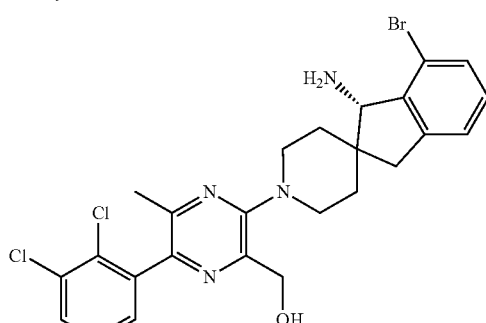
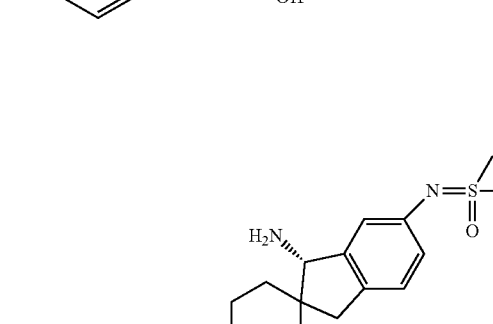

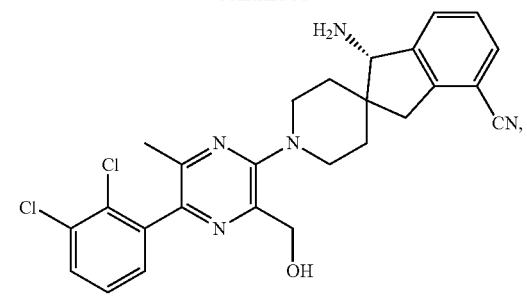
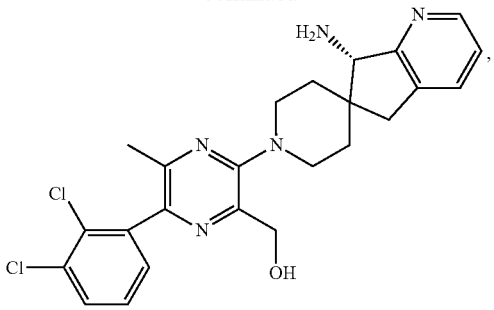
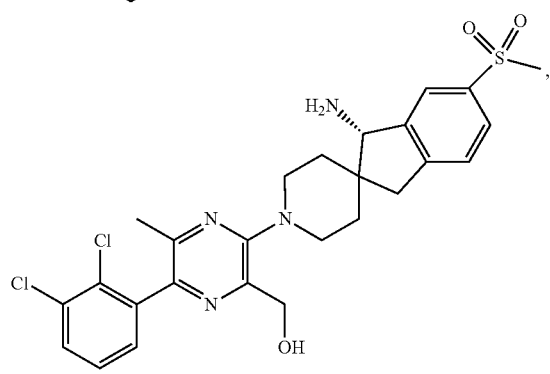
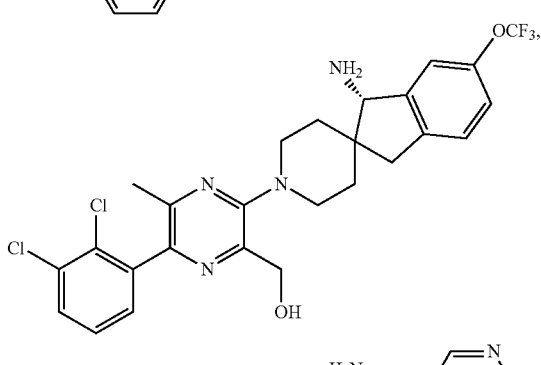
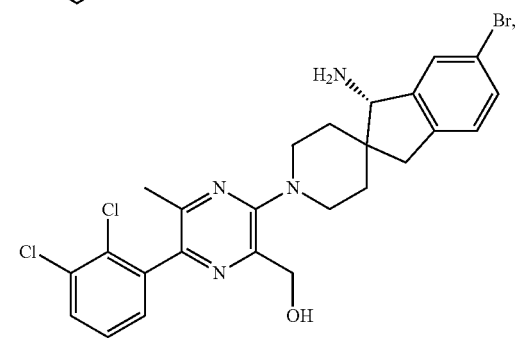
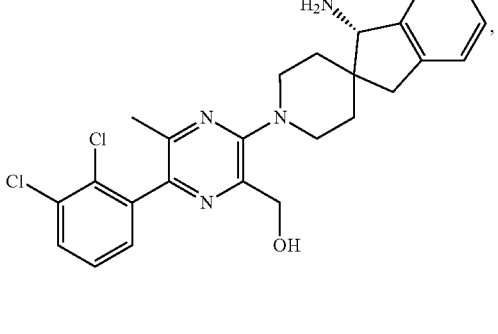
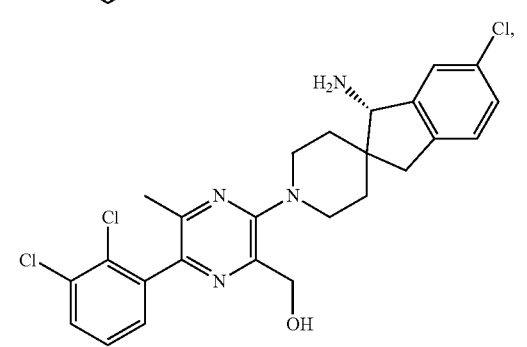
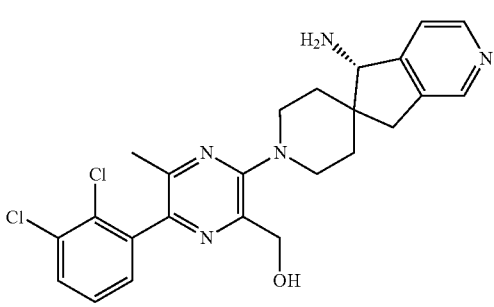
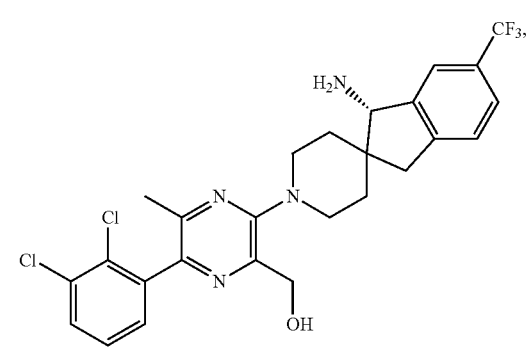
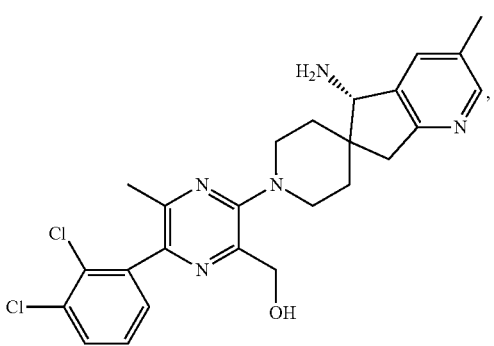

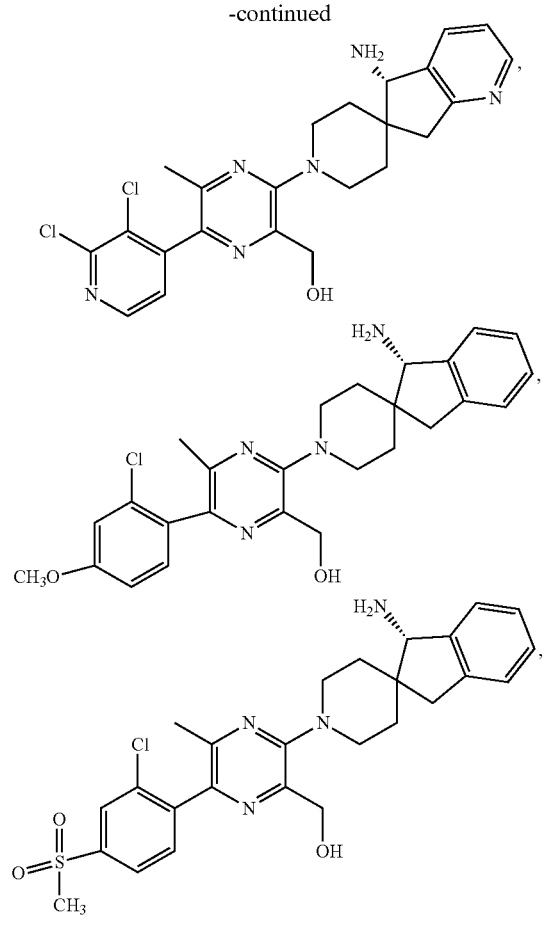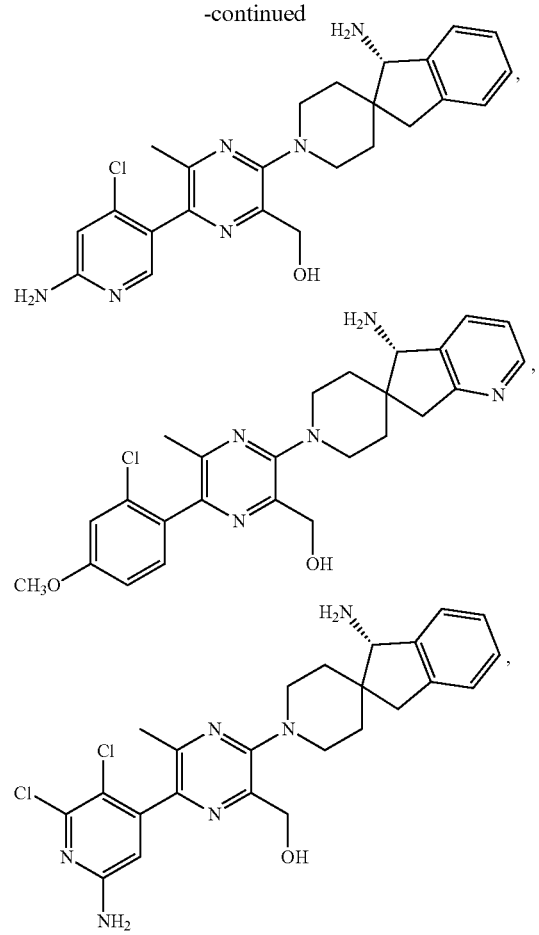

111
-continued
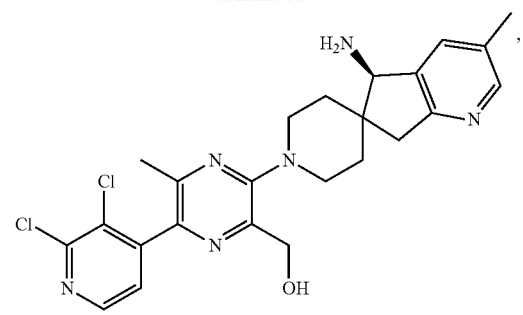
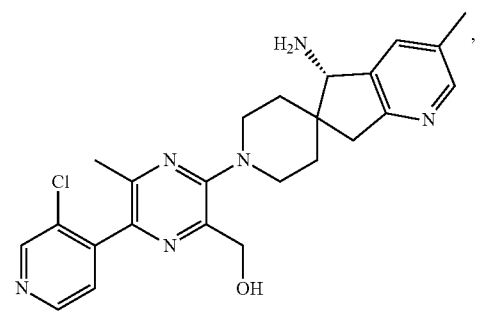
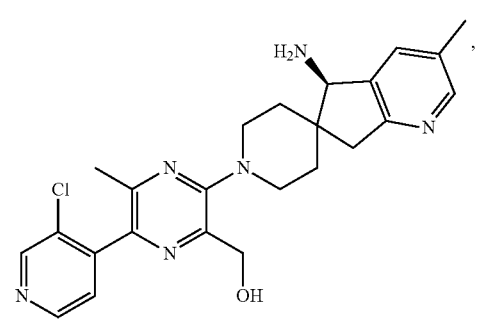
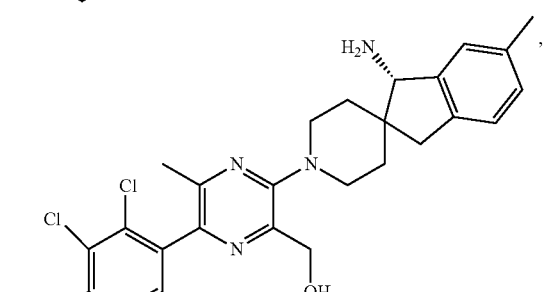
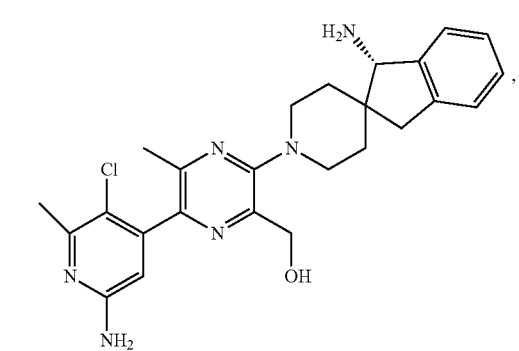
112
-continued
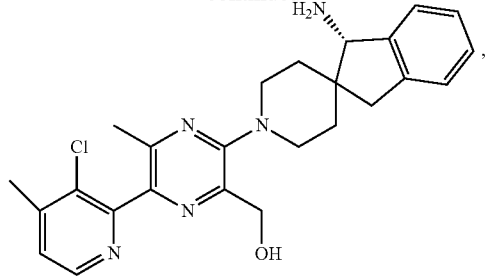
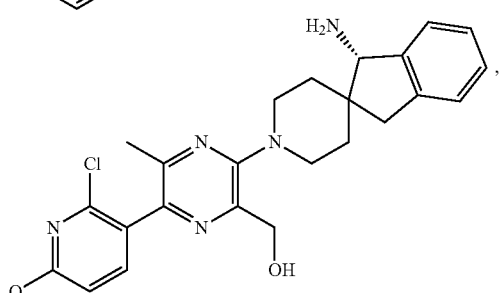
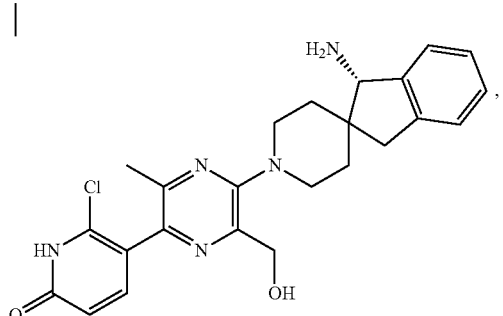
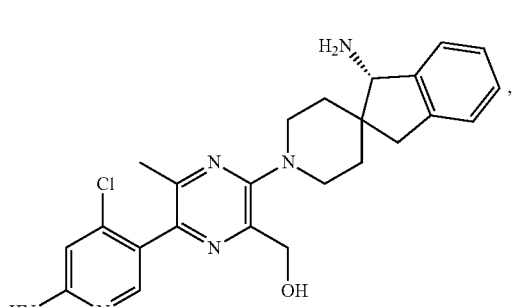
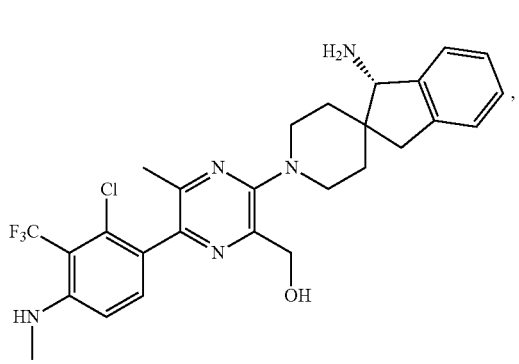

113
-continued
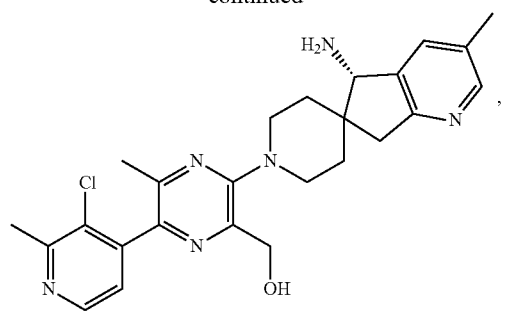
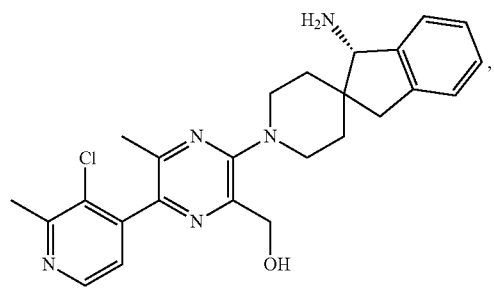
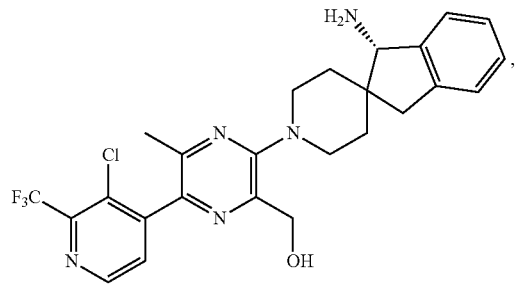
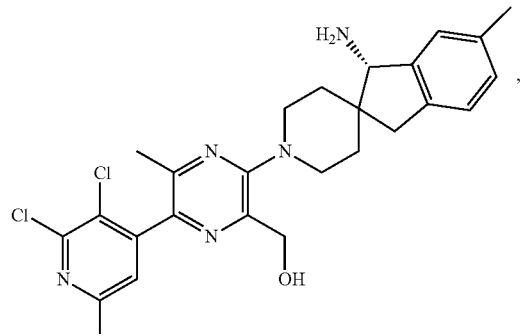
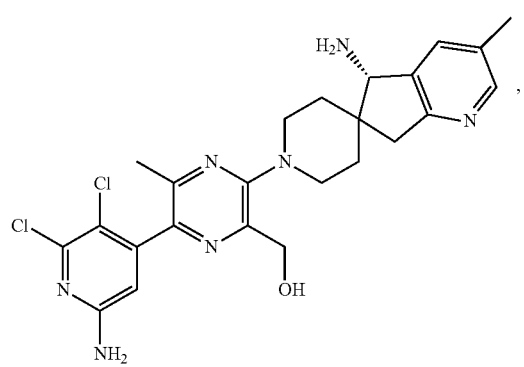
114
-continued
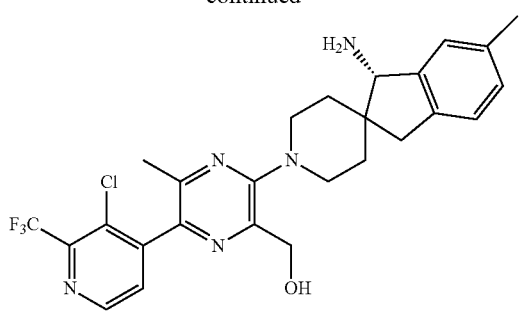
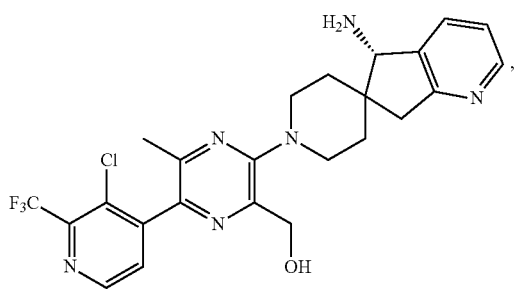
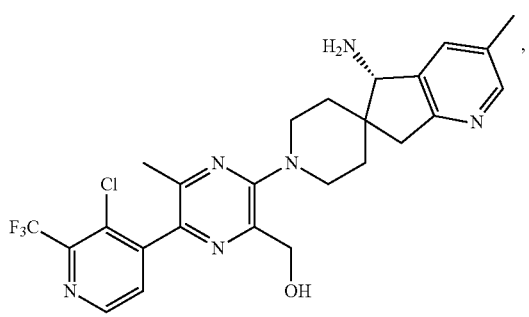
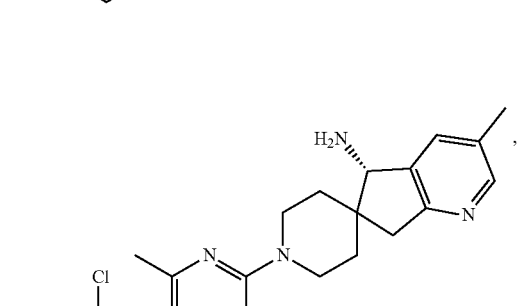
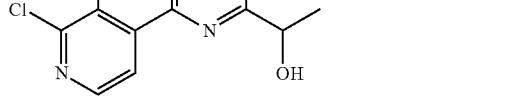
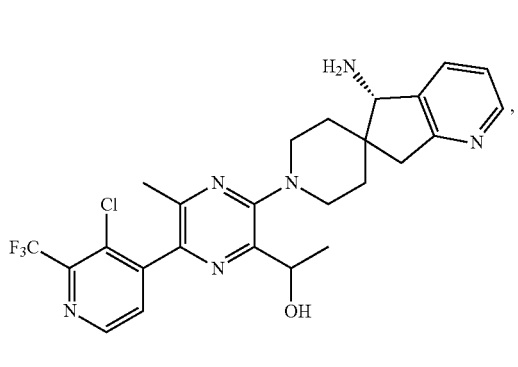

115
-continued
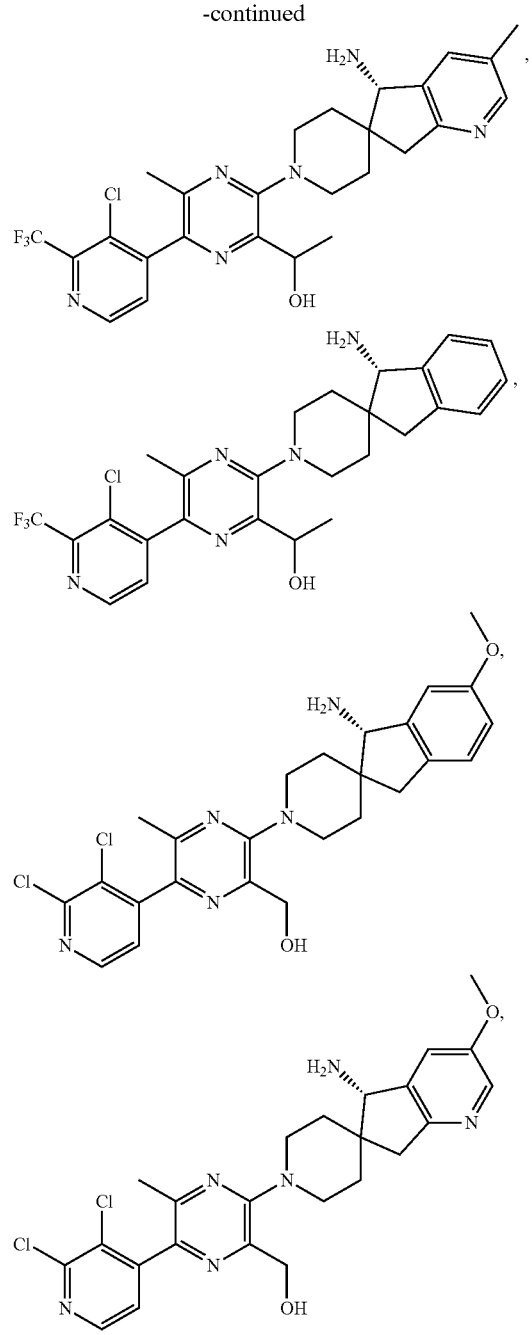
116
-continued
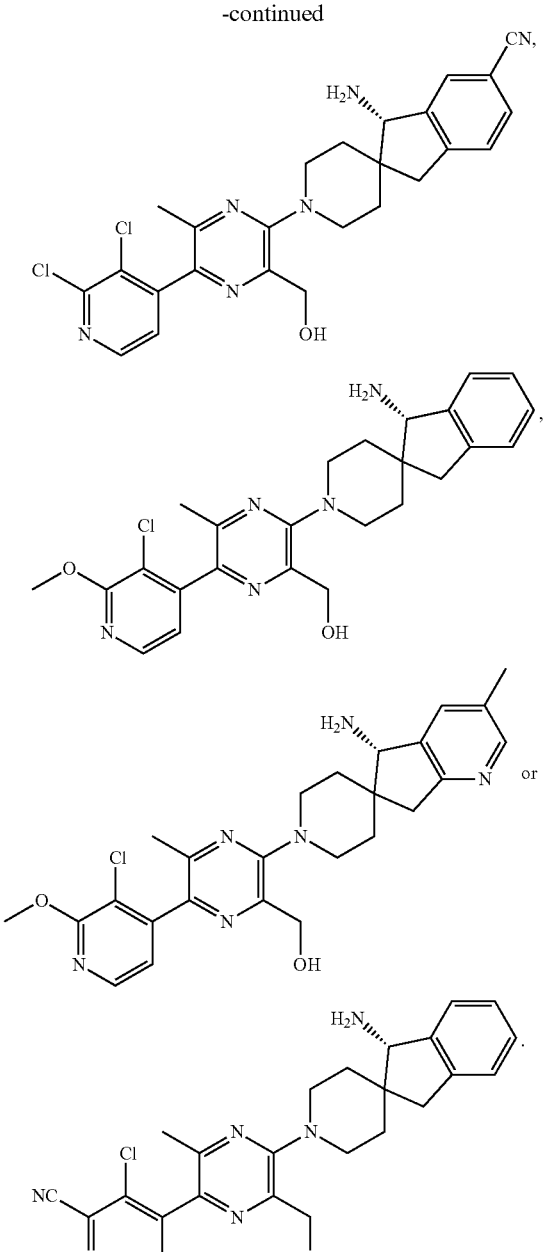
* * * * *